(12) United States Patent
Domkowski et al.

(10) Patent No.: US 7,569,036 B2
(45) Date of Patent: *Aug. 4, 2009

(54) INJECTION DEVICE AND METHOD OF ASSEMBLY AND ACTIVATION

(75) Inventors: John A. Domkowski, Kenosha, WI (US); Robert J. Oshgan, Lake Zurich, IL (US)

(73) Assignee: Hospira, Inc., Lake Forest, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/935,885

(22) Filed: Nov. 6, 2007

(65) Prior Publication Data

US 2008/0103455 A1 May 1, 2008

Related U.S. Application Data

(63) Continuation-in-part of application No. 11/749,446, filed on May 16, 2007.

(60) Provisional application No. 60/800,769, filed on May 16, 2006.

(51) Int. Cl.
*A61M 5/00* (2006.01)
(52) U.S. Cl. .................................... 604/232
(58) Field of Classification Search ......... 604/232–235, 604/208, 201, 198, 197, 110
See application file for complete search history.

(56) References Cited

U.S. PATENT DOCUMENTS

| 4,581,023 A | * | 4/1986 | Kuntz | 604/234 |
| 5,451,214 A | * | 9/1995 | Hajishoreh | 604/235 |
| 5,700,246 A | * | 12/1997 | Stiehl et al. | 604/198 |
| 2004/0249351 A1 | * | 12/2004 | Hongo et al. | 604/263 |

* cited by examiner

*Primary Examiner*—Kevin C Sirmons
*Assistant Examiner*—Catherine N Witczak
(74) *Attorney, Agent, or Firm*—Brian R. Woodworth

(57) ABSTRACT

An injector device for a pharmaceutical cartridge. The injector device includes a body defining a space for receiving a pharmaceutical cartridge. One or more retention members are disposed on the outer surface of the body. The injector device further includes a plunger rod having a connection member constructed for connection to a piston associated with a cartridge. The plunger rod has one or more receiving members. constructed to cooperatively retain the plunger rod on the body in a first position, and to release the plunger rod from the body when the plunger rod is moved to a second position. The plunger rod further includes a surface for engaging a pharmaceutical cartridge positioned within the body of said injector and for moving a pharmaceutical cartridge distally as the plunger rod is moved from its first position to its second position. A tamper evident band is secured to plunger rod and injector body.

18 Claims, 44 Drawing Sheets

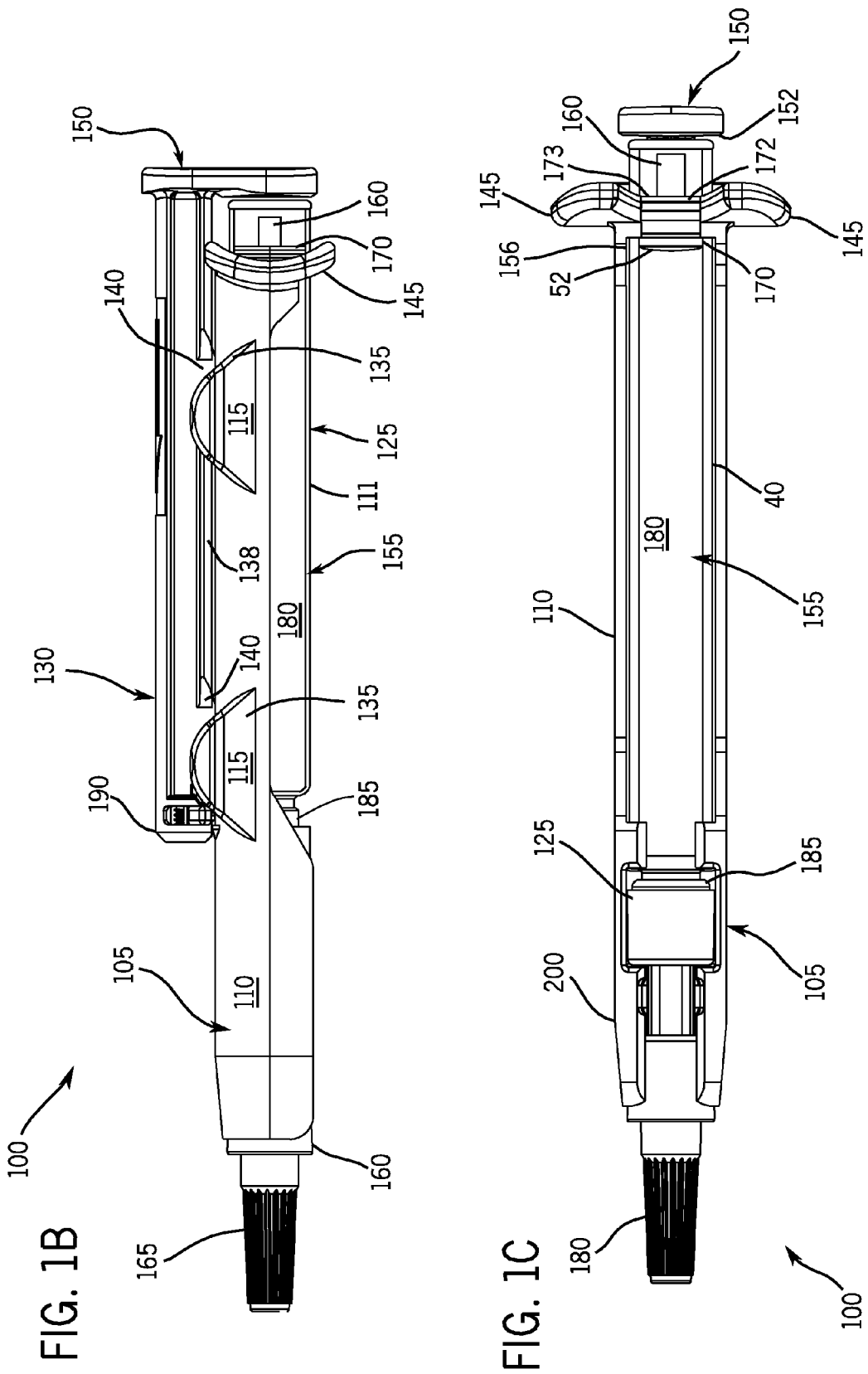

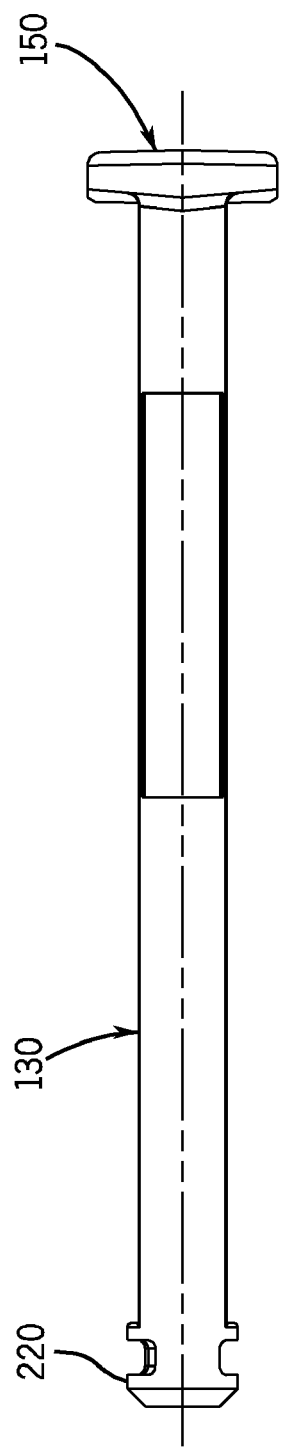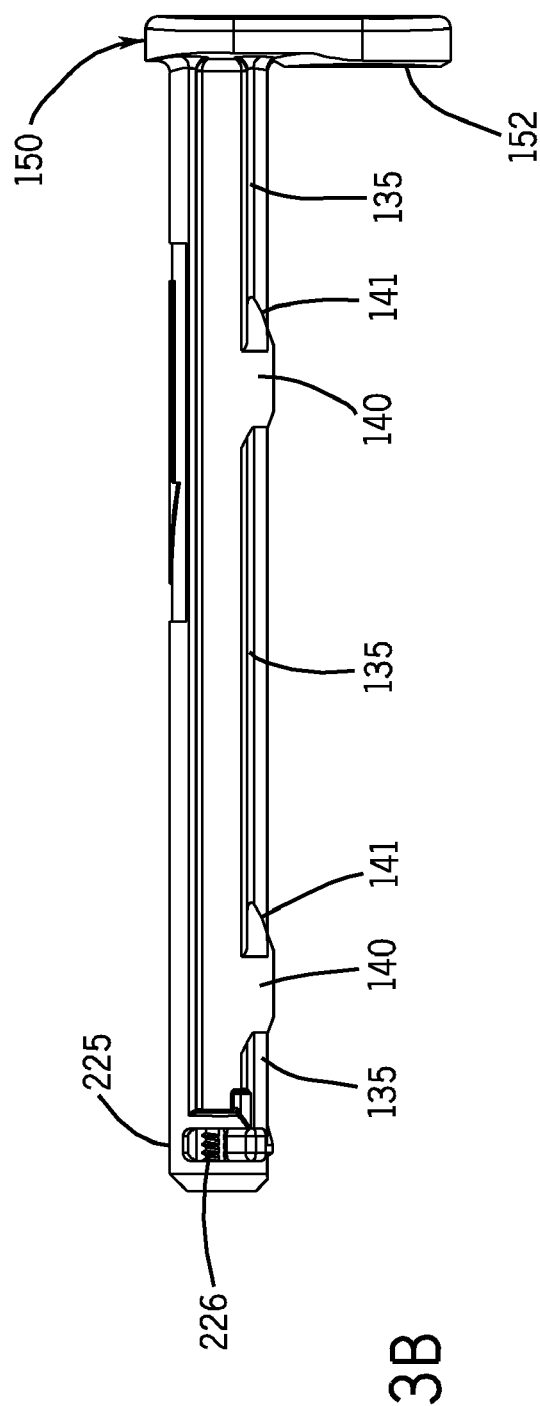

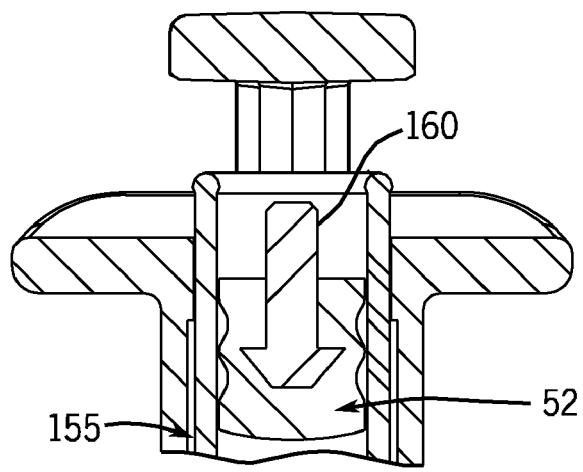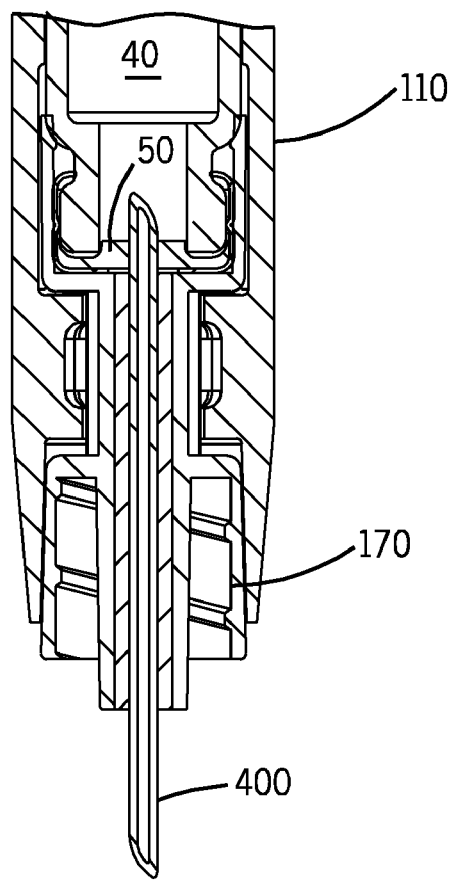
FIG. 4B

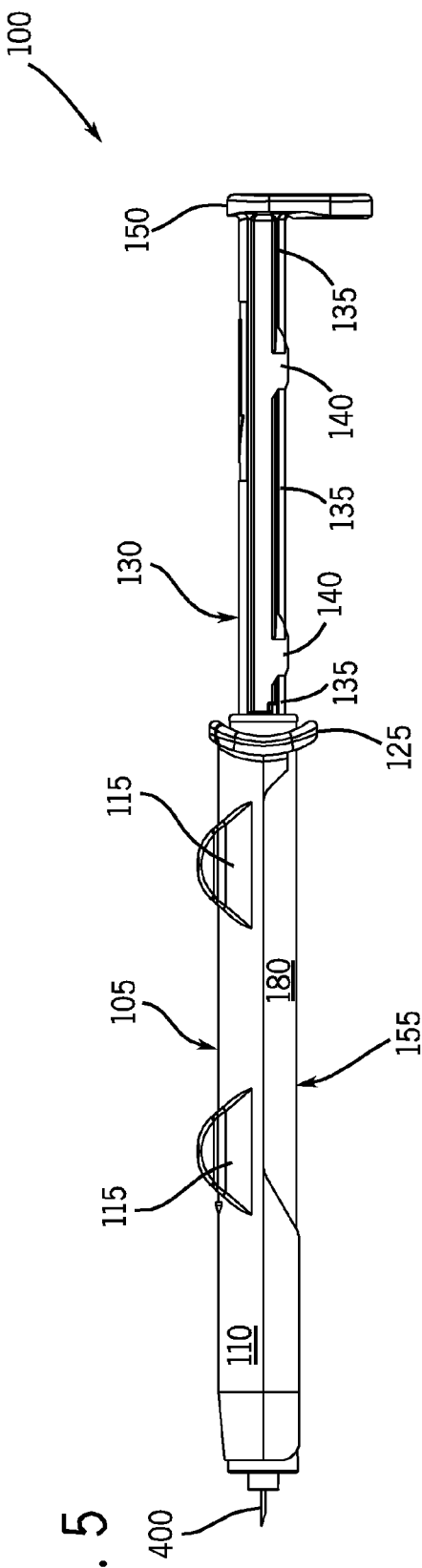

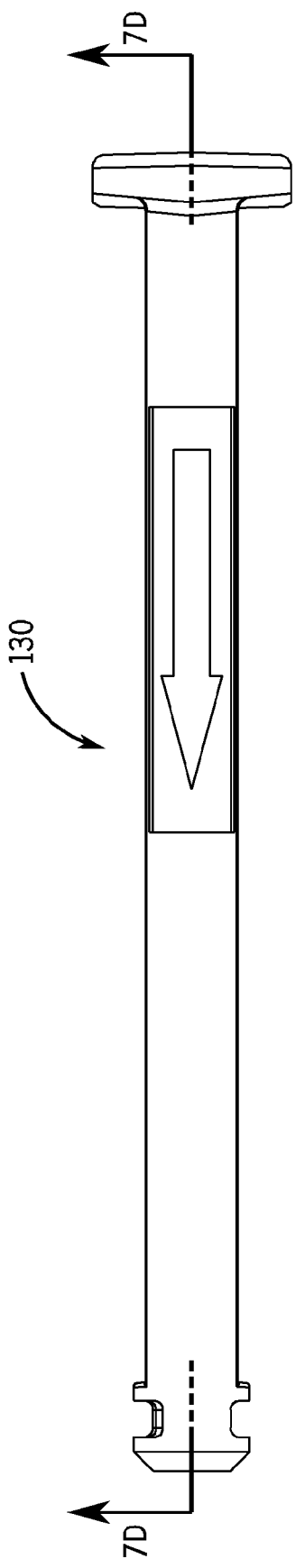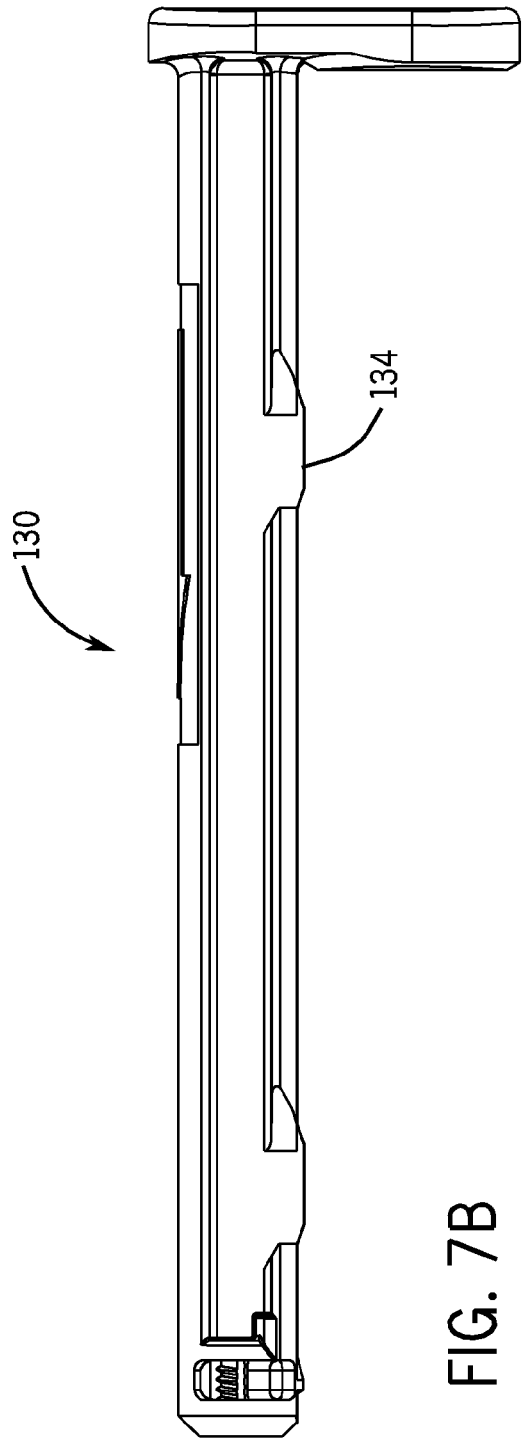

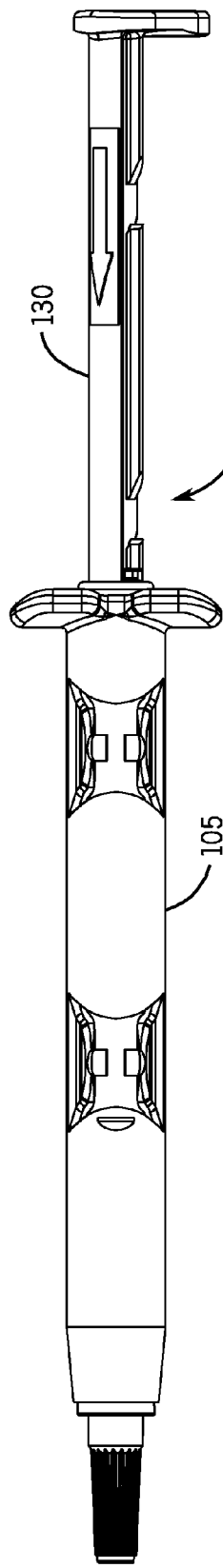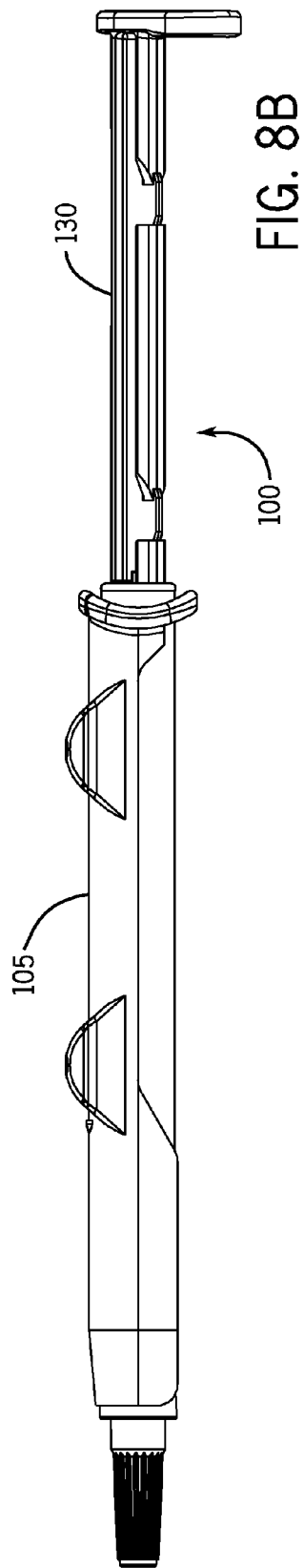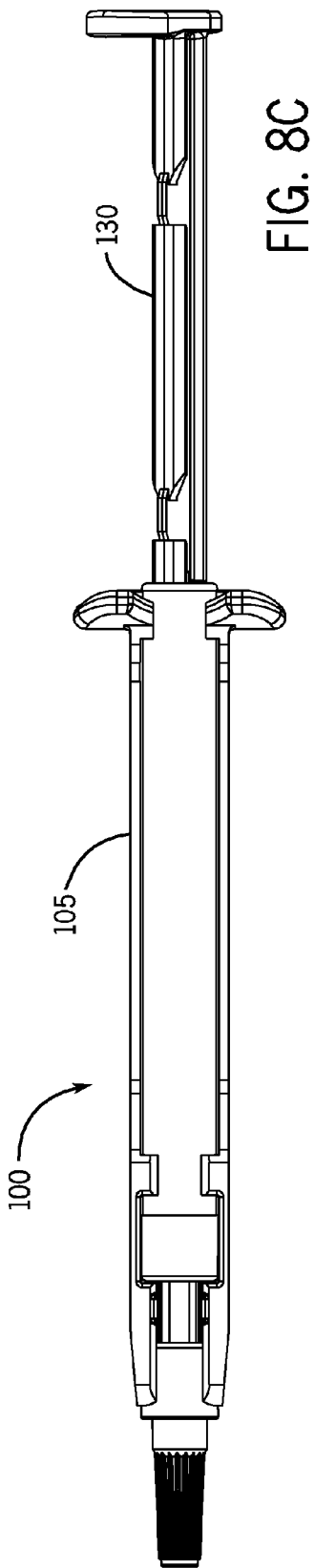

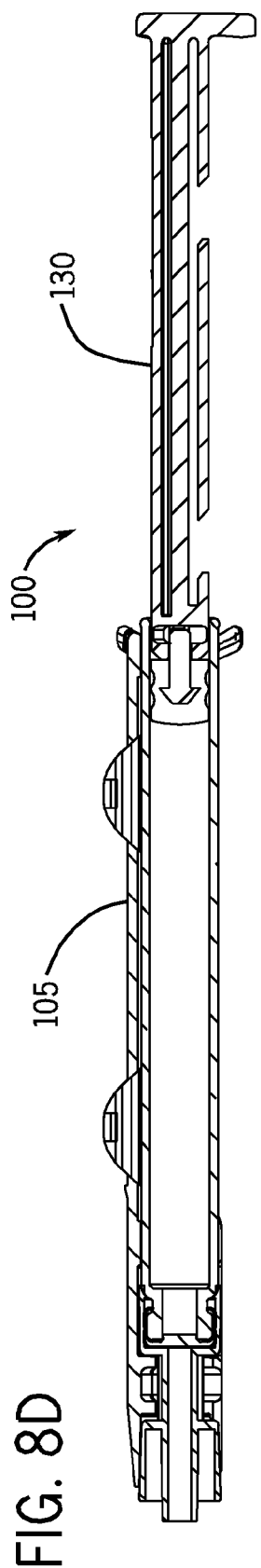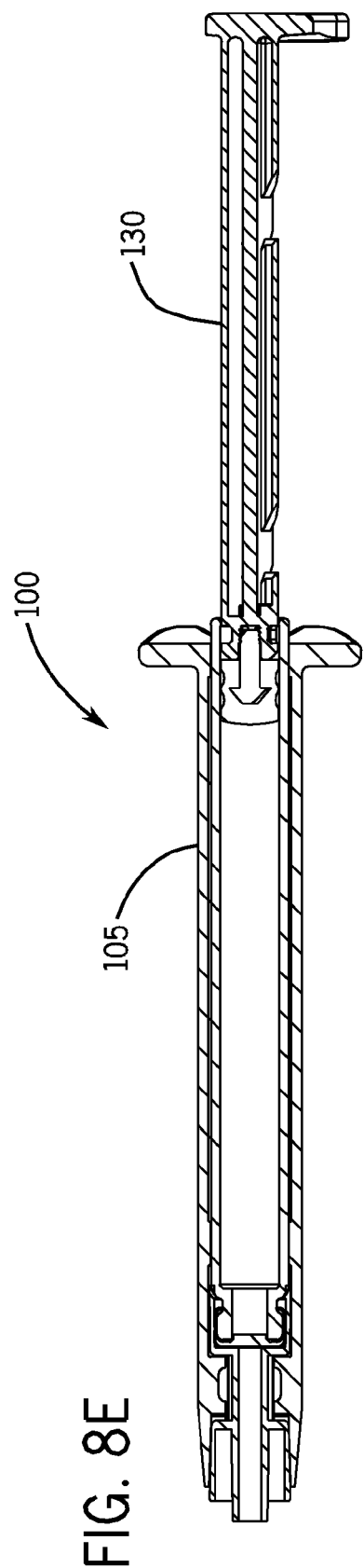

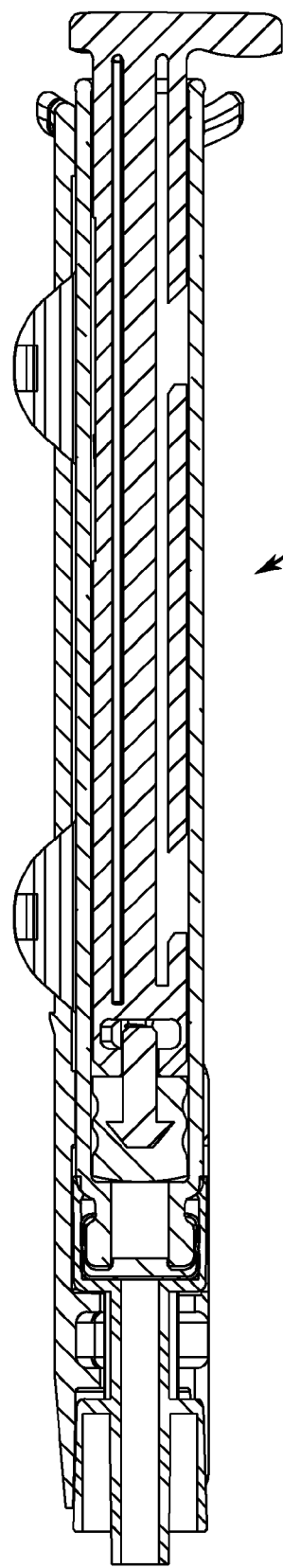
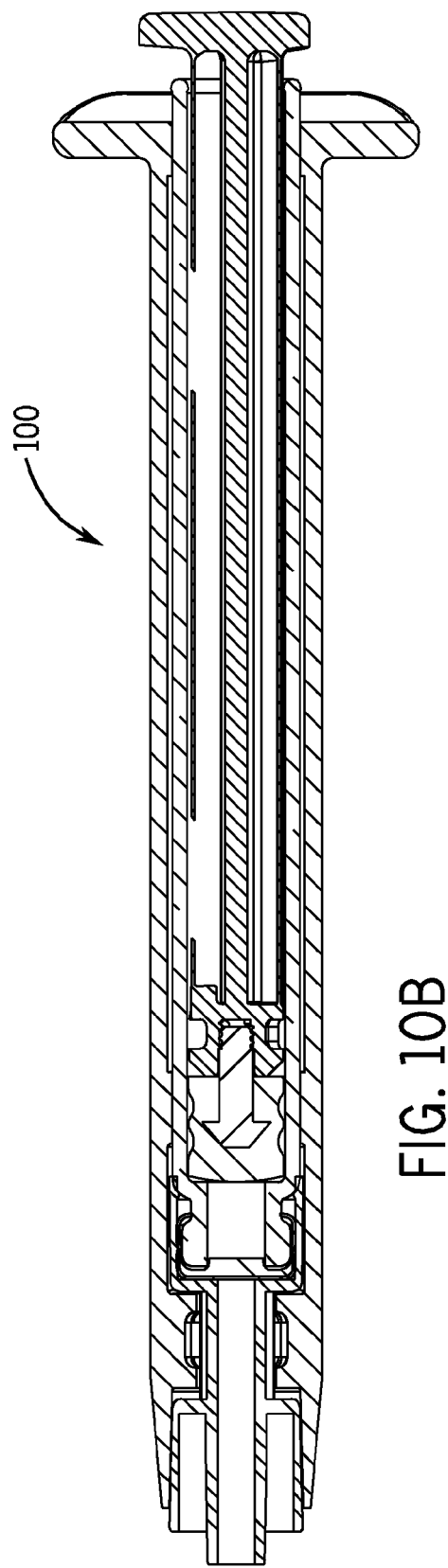
FIG. 10A
FIG. 10B

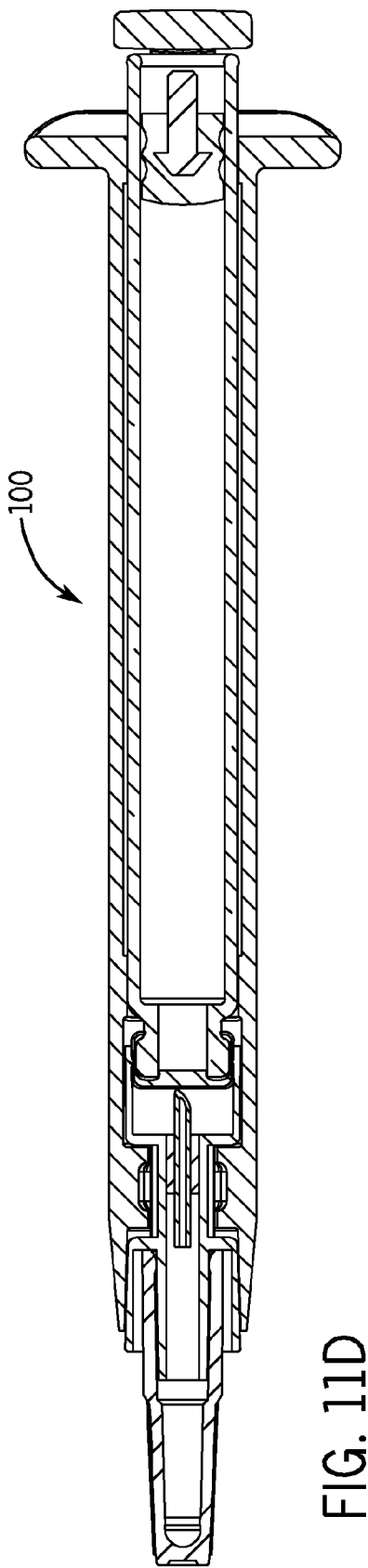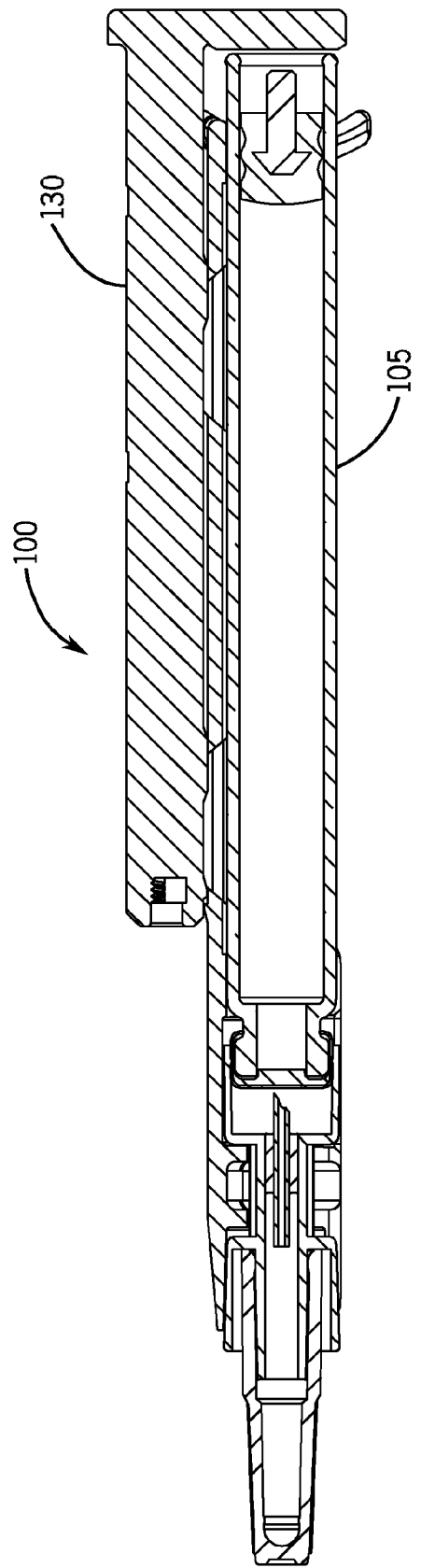
FIG. 11D
FIG. 11E

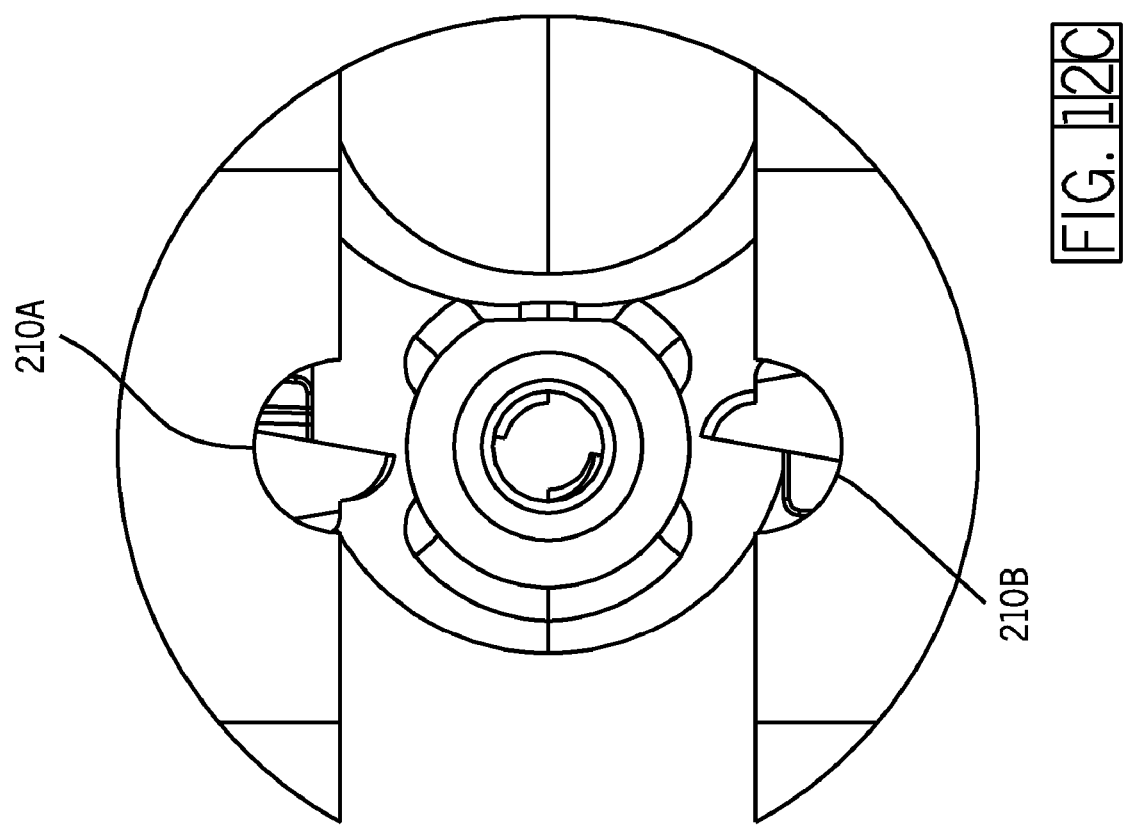

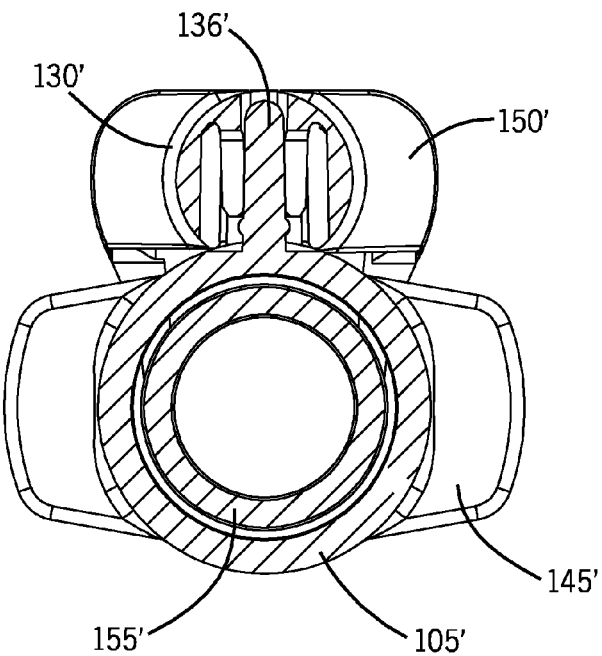
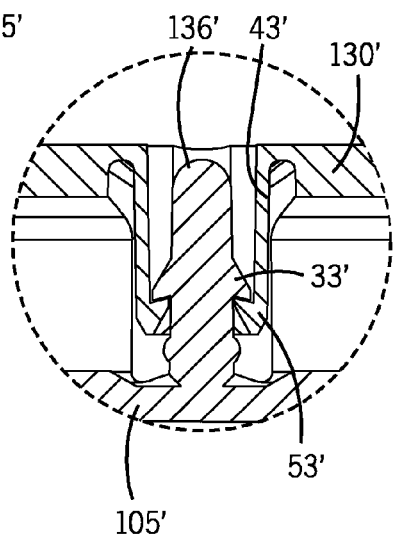
FIG. 20
FIG. 21
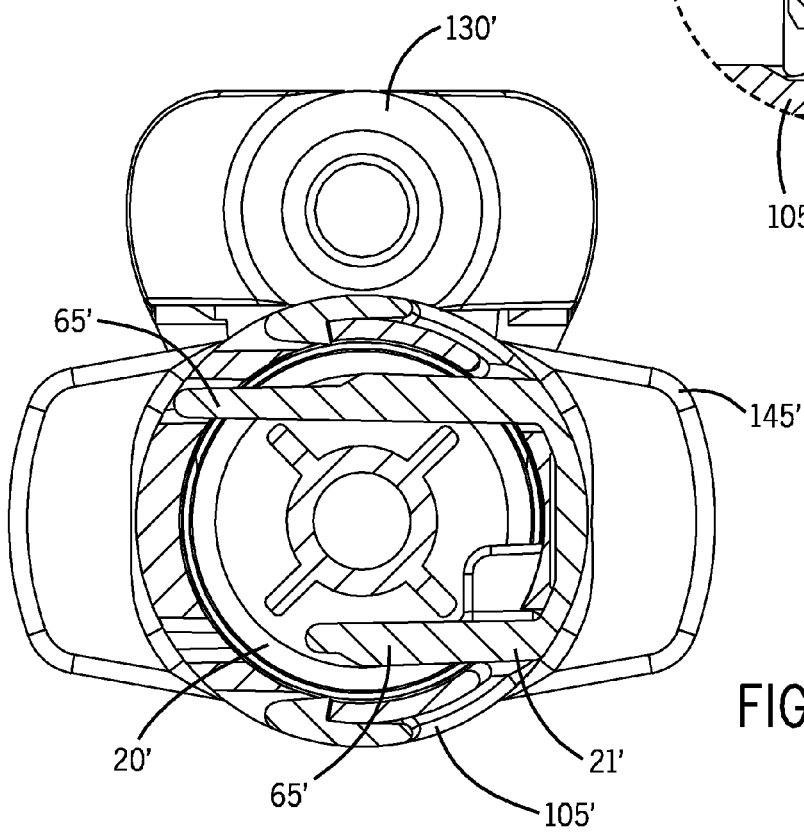
FIG. 22

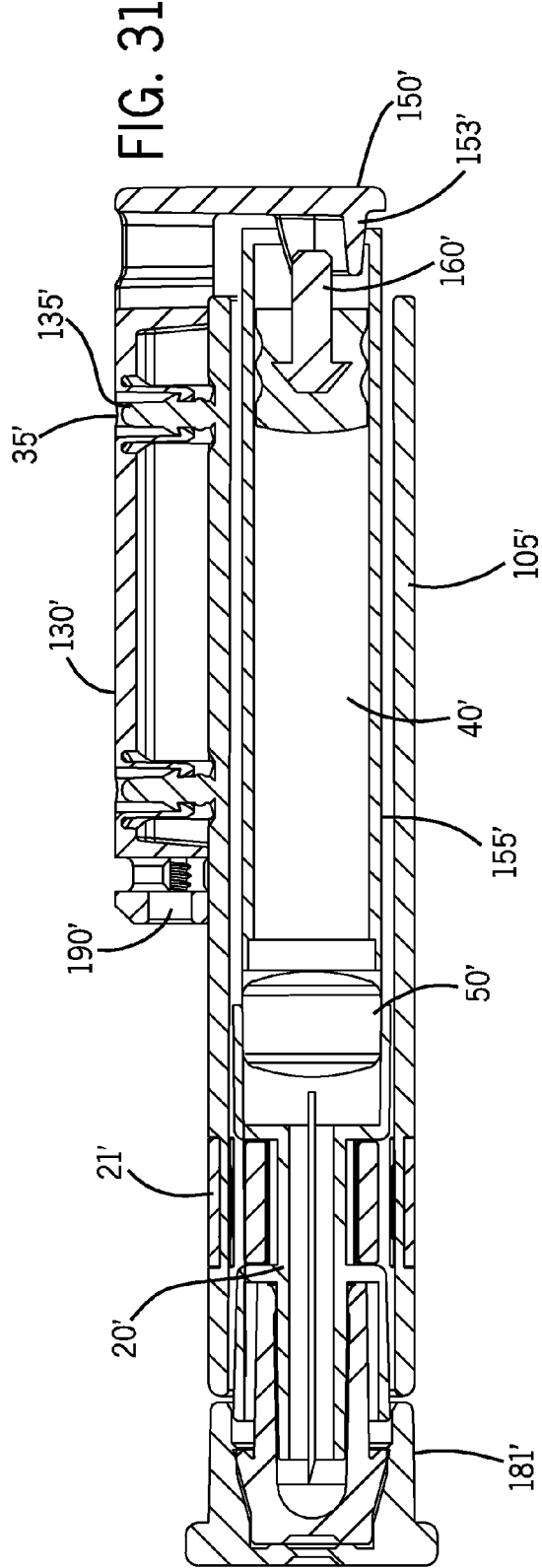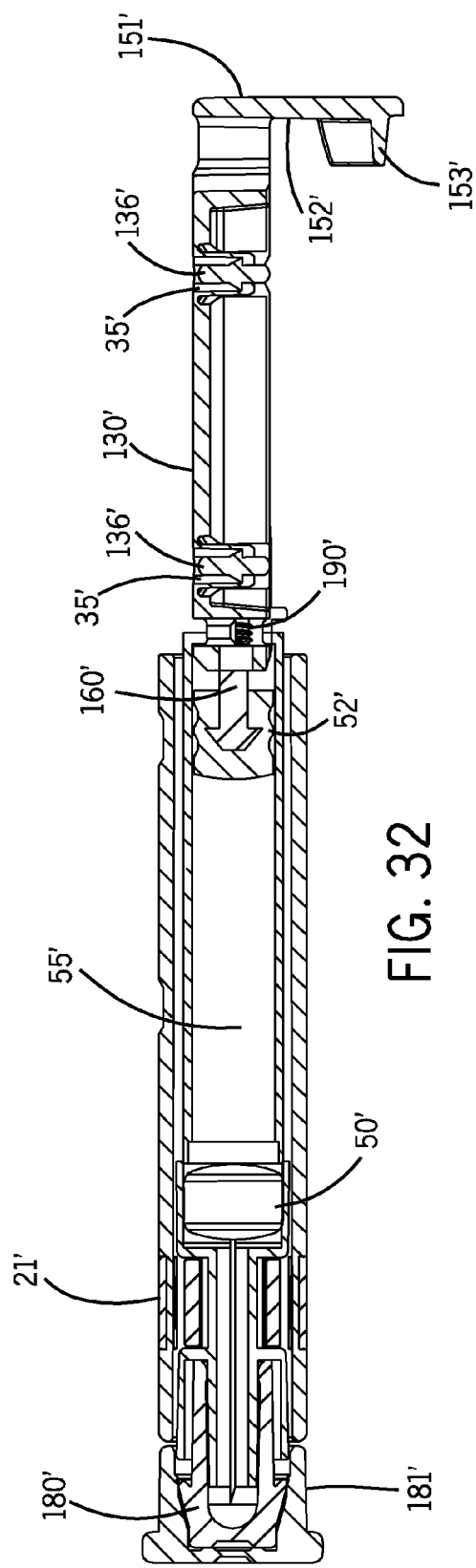

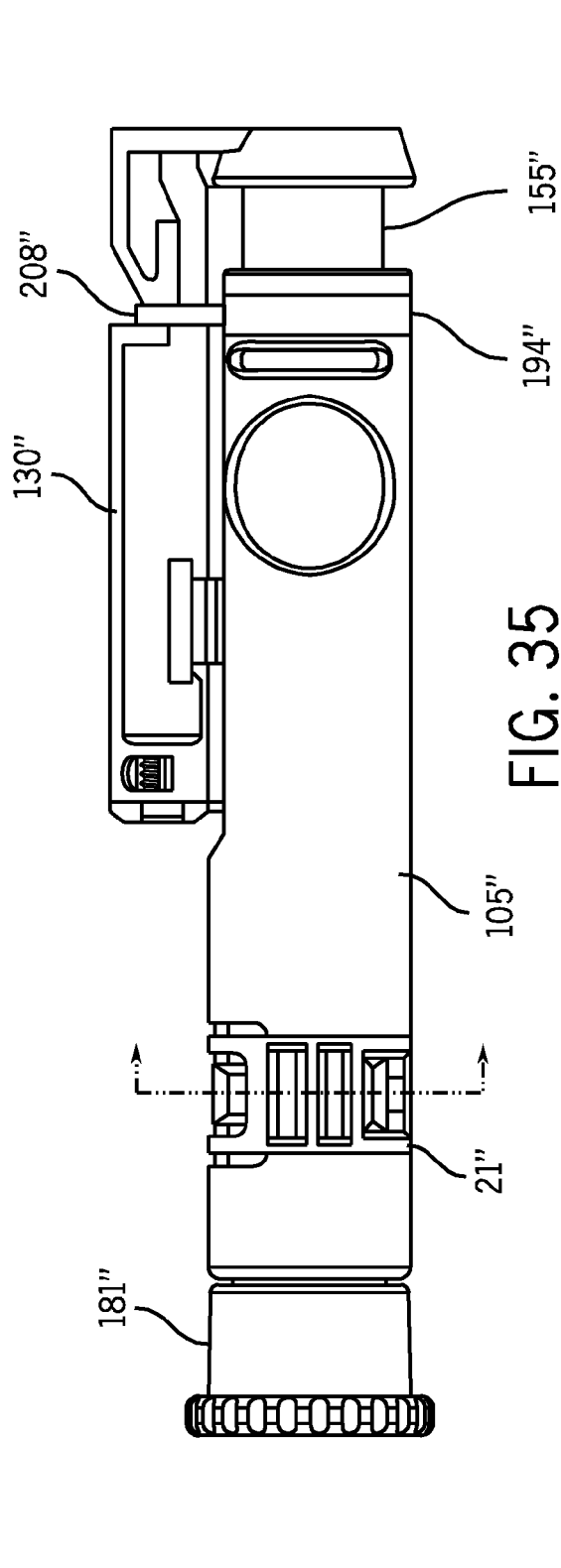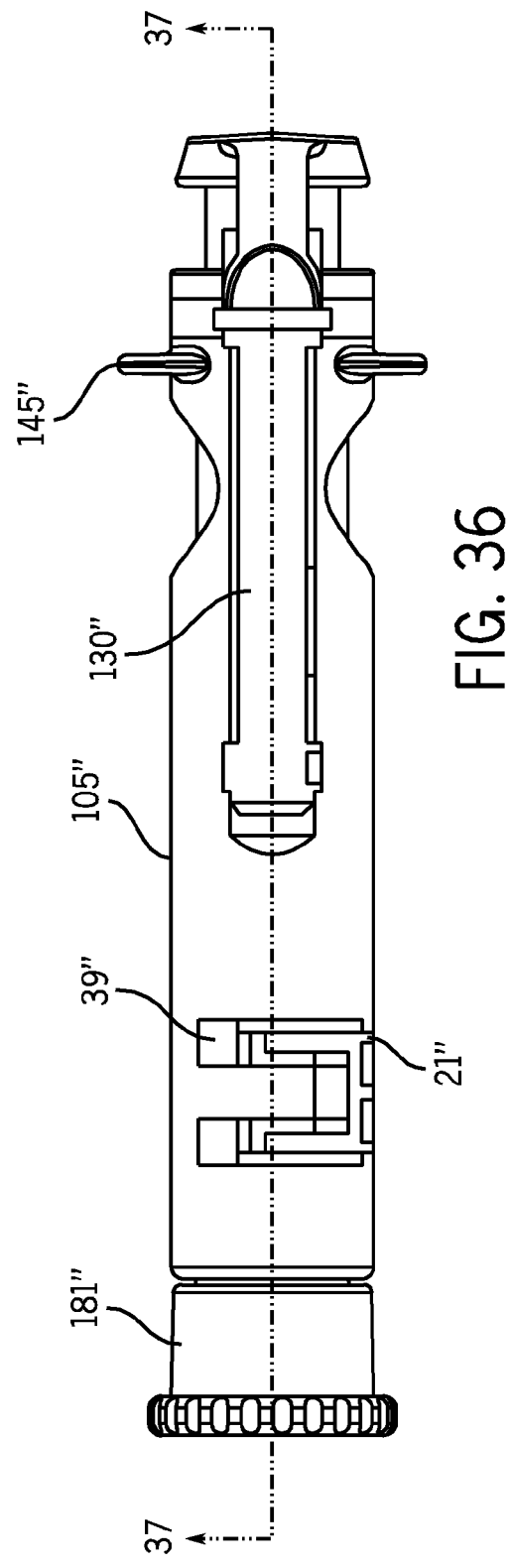

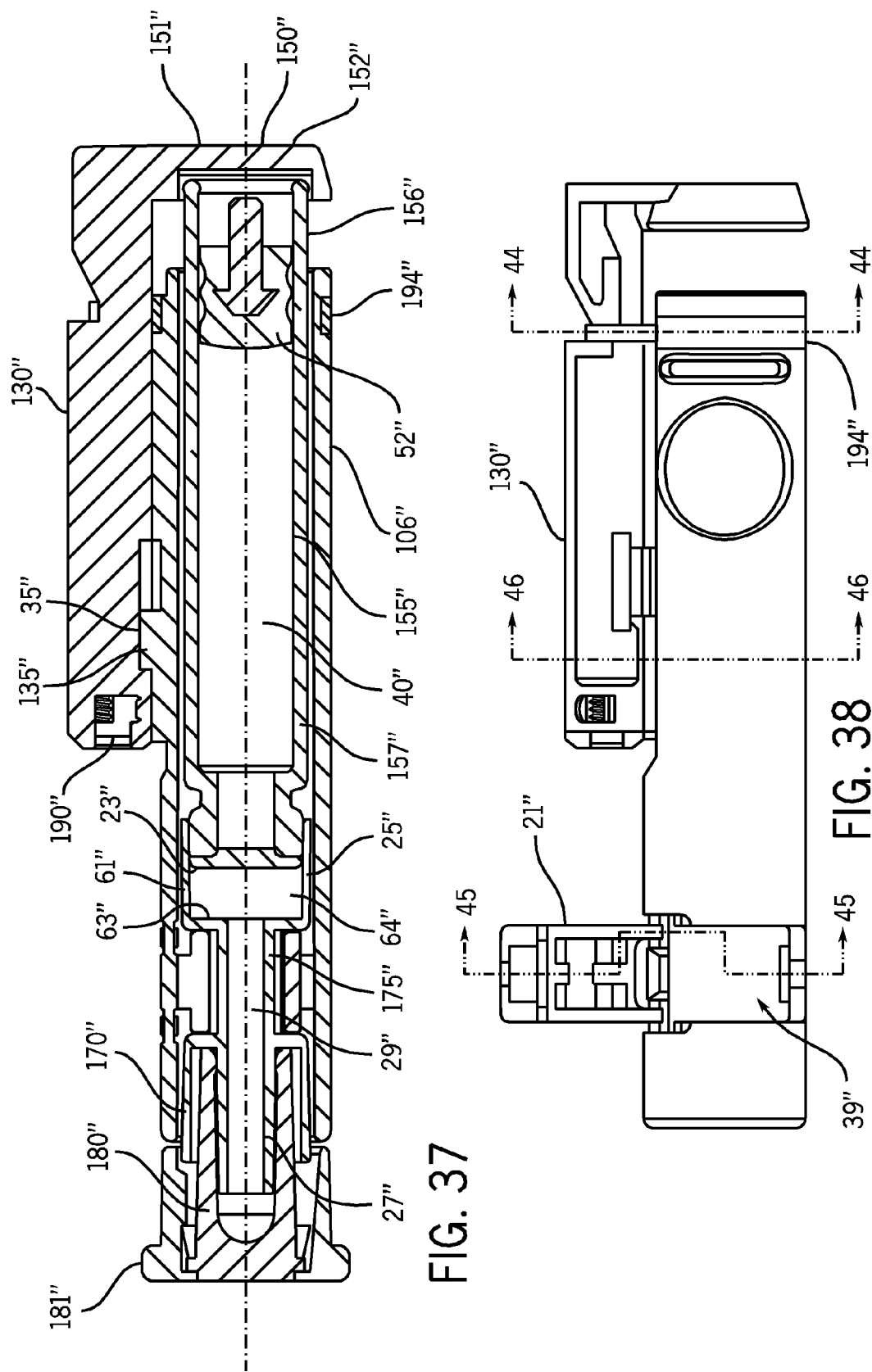

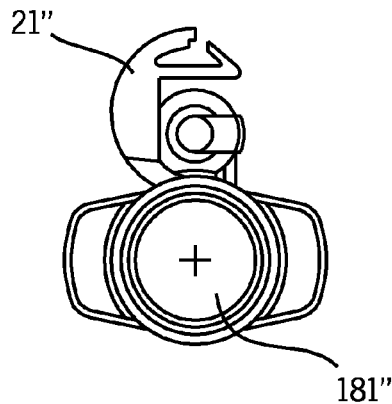
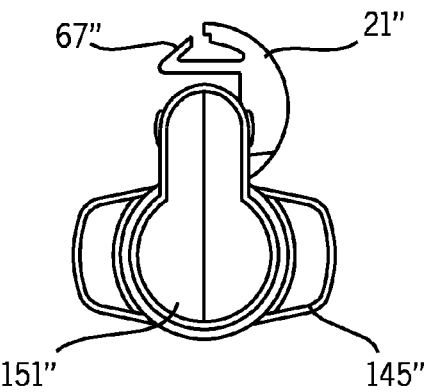
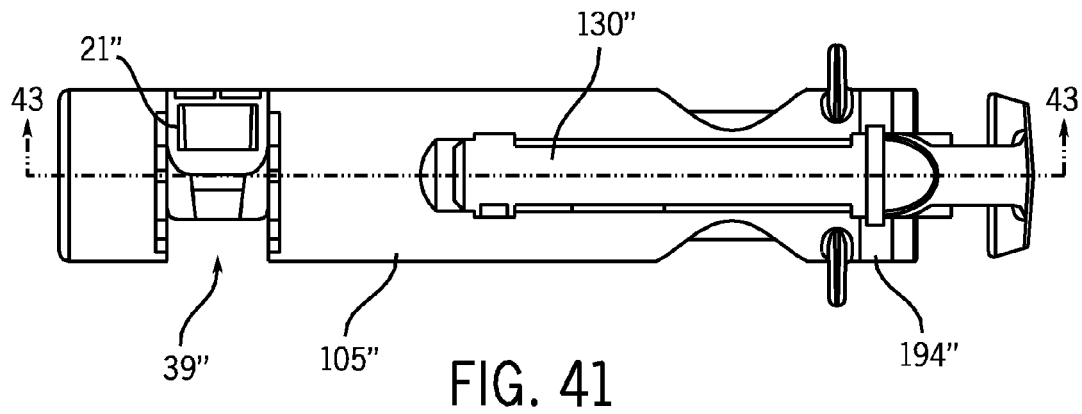
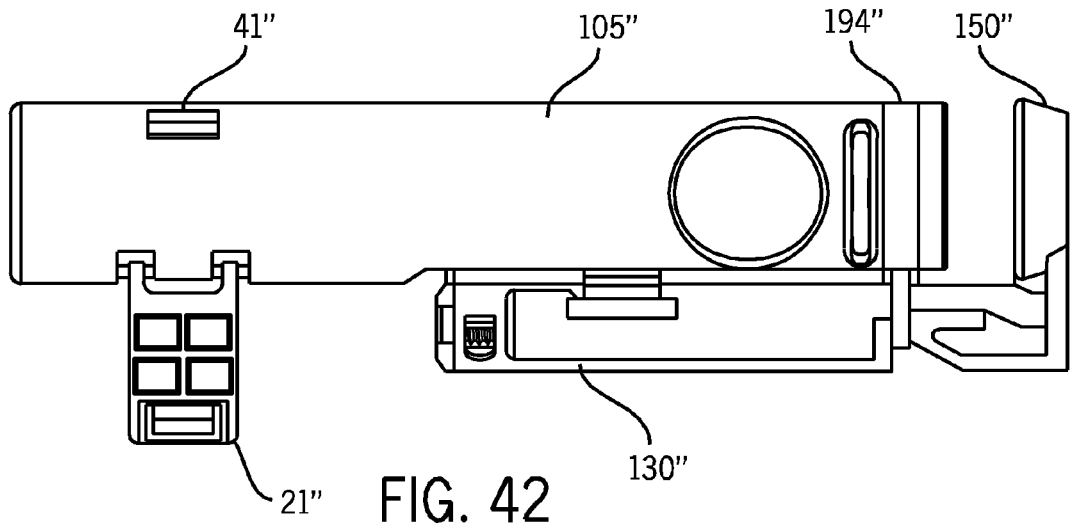

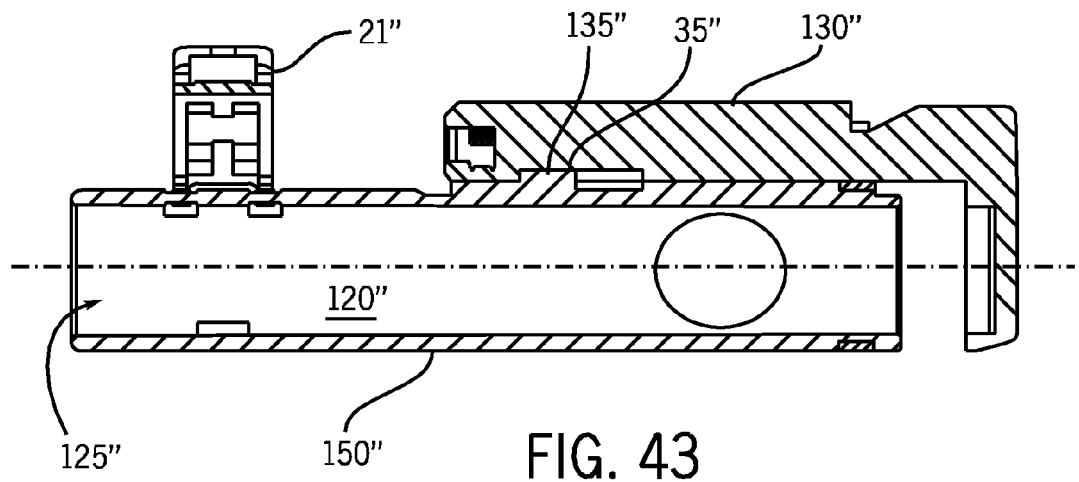
FIG. 43
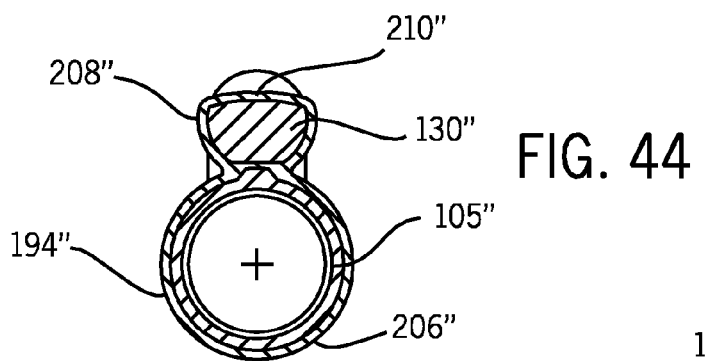
FIG. 44
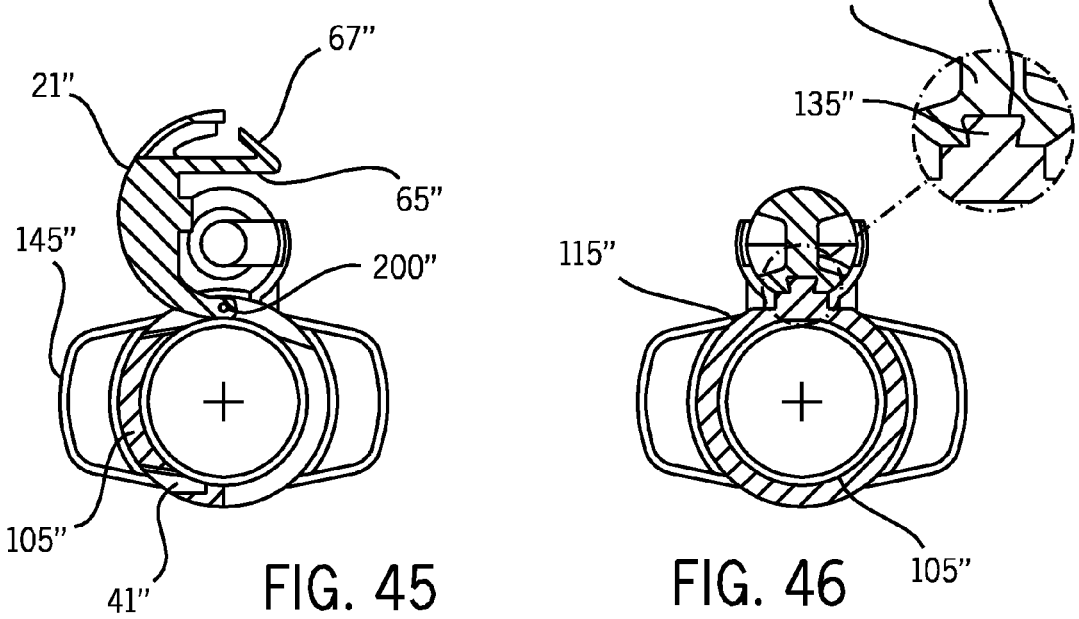
FIG. 45
FIG. 46

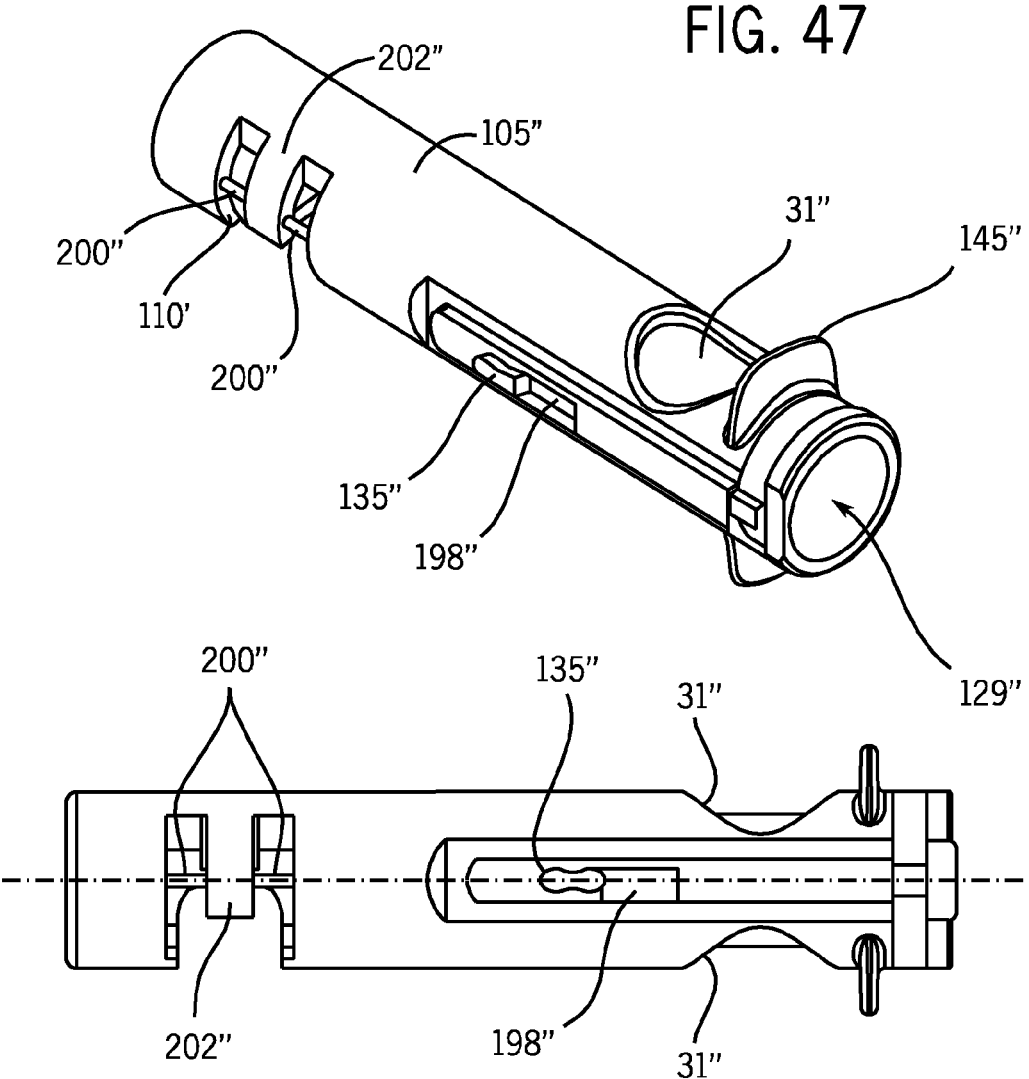
FIG. 47
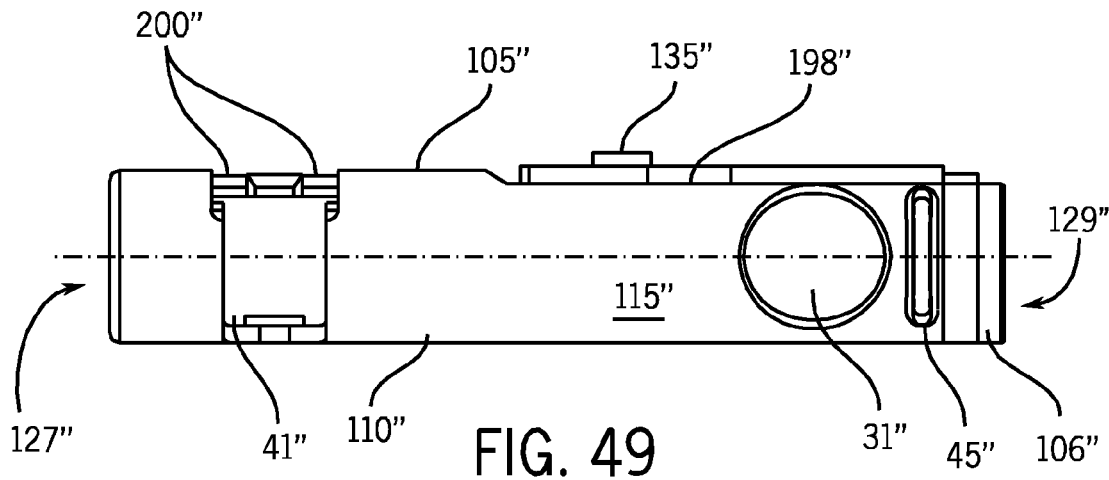
FIG. 48
FIG. 49

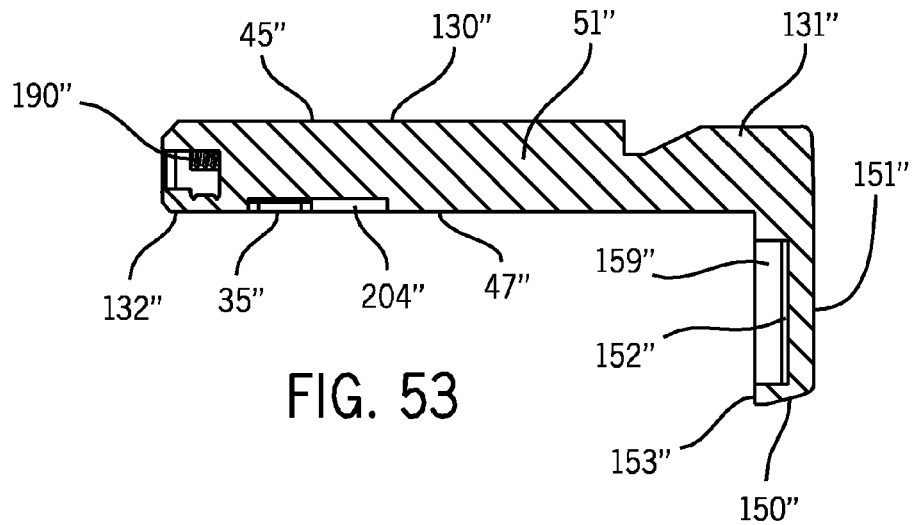
FIG. 53
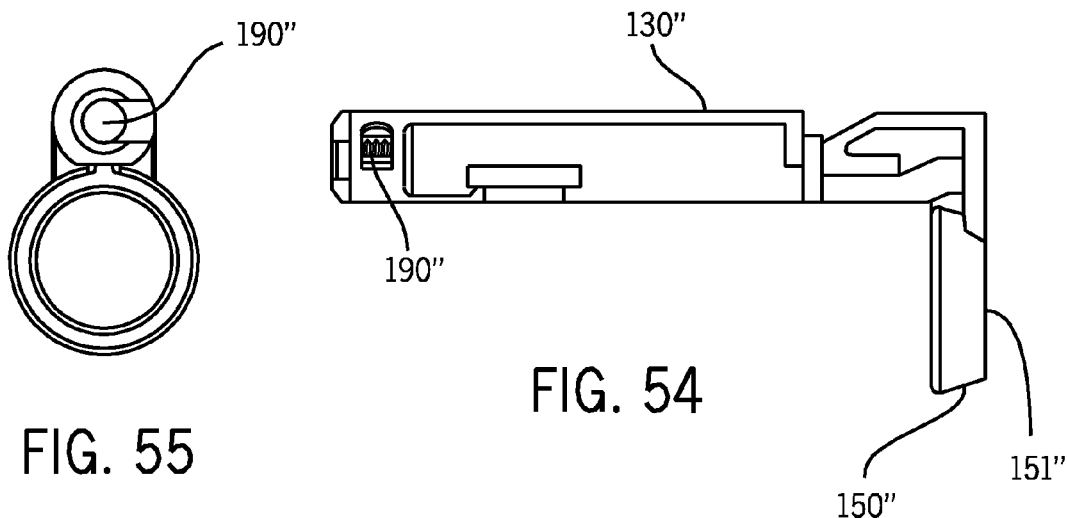
FIG. 55
FIG. 54
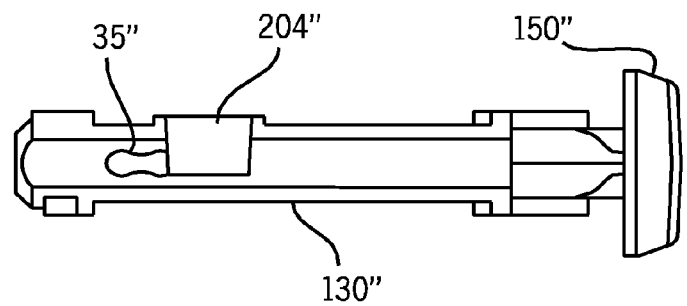
FIG. 56

INJECTION DEVICE AND METHOD OF ASSEMBLY AND ACTIVATION

CROSS-REFERENCE TO RELATED APPLICATIONS

This application is a continuation-in-part of U.S. patent application Ser. No. 11/749,446 filed on May 16, 2007, which claims priority of U.S. Provisional Patent Application Ser. No. 60/800,769 filed on May 16, 2006, both of which are expressly incorporated herein by reference and made a part hereof.

FEDERALLY SPONSORED RESEARCH OR DEVELOPMENT

Not Applicable.

TECHNICAL FIELD

The present invention relates generally to injection systems for delivering a pharmaceutical product to a patient, and more particularly to a system for expelling a pharmaceutical product from a cartridge and a method for manufacturing an injection device.

BACKGROUND OF THE INVENTION

Pharmaceutical products are often delivered or transferred through the use of a syringe or a syringe system. Syringe systems can include a needle of known construction, thereby enabling direct delivery of the pharmaceutical product directly into a patient, e.g., through intravenous injection, or through a septum that fluidly seals a port associated with a tube set that is, or can be, fluidly connected to a patient. Alternatively, the syringe system can be provided with a blunt needle that is constructed to be inserted through a pre-pierced septum of a tube set. The syringe system can also include a luer fitment (male or female, locking or not-locking) configured to mate with a complementary luer fitment for transfer of the pharmaceutical product from the syringe system into another medical system, e.g., transfer from the syringe to a luer-activated valve associated with a tube set.

Many pharmaceutical products in the market today are provided in an ampule or cartridge. These ampules or cartridges can be configured for use with an injection device or system that is designed to be connected to the ampules or cartridges such that a medical professional can expel the pharmaceutical product from the ampule or cartridge for delivery to the patient or transfer to another medical system. One example of an ampule or cartridge is the CARPULE® system sold by Hospira, Inc., the Assignee of this application and the inventions disclosed herein.

U.S. Pat. No. 5,653,698, which is incorporated herein by reference in its entirety, provides detailed insight into the structure and operation of a pharmaceutical cartridge of the type to be used in the present invention. The cartridge system disclosed in U.S. Pat. No. 5,653,698 includes a cartridge 40 configured to retain a pharmaceutical product therein. A piston 52 is positioned within the cartridge and fluidly seals a first, open end of the cylindrical wall 44 of cartridge 40. Piston 52 is movable within cartridge 40 such that it causes the pharmaceutical product contained in the cartridge 40 to be ejected from the cartridge as piston 52 is moved toward the second end of the cartridge. A threaded rod 54 is attached to piston 52, the threaded rod 54 being constructed to threadably attach to a piston stem 62 which can be used to facilitate movement of piston 52 within cartridge 40. The second end of cartridge 40 is fluidly sealed by a pierceable diaphragm 50 which precludes the ejection of the pharmaceutical product from the cartridge so long as the pierceable diaphragm is intact.

The cartridge system disclosed in U.S. Pat. No. 5,653,698 further includes a hub 20 portion mounted on the second end of cartridge 40. Hub 20 includes a snapping sleeve portion 22 that is movably disposed over the second end of cartridge 40. Hub 20 further includes a needle cannula 18 which, when hub 20 and cartridge 40 are moved toward one another, pierces pierceable diaphragm 50 in order to provide for an egress pathway for the pharmaceutical product contained in cartridge 40.

In use, cartridge 40 of the cartridge system disclosed in U.S. Pat. No. 5,653,698 is placed into a reusable syringe holder 56 such that ampule/cartridge 40 and snapping sleeve portion 22 of hub 20 are positioned within the holder 56. Piston stem 62 is then rotated clockwise to lock ampule 40 within holder 56 and to simultaneously urge ampule 40 forward. Because hub 20 is prevented from moving forward by holder 56, this forward movement of ampule 40 causes ampule 40 and hub 20 to move toward one another, causing needle cannula 18 to pierce pierceable diaphragm 50, and thereby providing fluid communication between the interior of ampule 40 and the interior of needle cannula 18 such that movement of piston 52 will cause fluid to be drawn into or ejected from the ampule 40, depending upon the direction of movement imparted to piston 52.

Systems of the type disclosed in U.S. Pat. No. 5,653,698 can be provided with a variety of structures for delivery or transfer of the pharmaceutical product, including needles for injecting the pharmaceutical product into a patient or for injecting the pharmaceutical product into an add port associated with a drug delivery tube set of known construction. Alternatively, a male or female luer fitting (including both locking and non-locking luer fittings) can be associated with or attached to the hub for delivery of the pharmaceutical product through a medical device having a complementary luer fitting, e.g., a luer-activated valve. Also, a blunt tube can be associated with the hub for delivery of the pharmaceutical product to a medical device having a septum, e.g., a pre-pierced septum, through which the blunt tube can be urged in order to permit the contents of the cartridge to be ejected into the medical device.

Additional examples of injectors constructed for the delivery of pharmaceutical products from a cartridge can be found in U.S. Pat. Nos. 5,447,500; 5,573,514; and Des. 366,698, each of which is incorporated herein in its entirety. The foregoing examples of the background art are intended to be illustrative and not exclusive.

Accordingly, syringe systems and injectors constructed for the delivery of pharmaceutical products from a cartridge are well known in the art. While such syringe systems and injectors according to the prior art provide a number of advantageous features, they nevertheless have certain limitations. The present invention seeks to overcome certain of these limitations and other drawbacks of the prior art, and to provide new features not heretofore available. A full discussion of the features and advantages of the present invention is deferred to the following detailed description, which proceeds with reference to the accompanying drawings.

SUMMARY OF THE INVENTION

The present invention generally provides an injector device for use with a pharmaceutical cartridge. According to one embodiment, the injector device includes a syringe or injector body, and a plunger rod. The plunger rod is fixedly connected to the injector body in a first position, and is disassociated from the injector body in a second position.

According to another embodiment, the injector device generally comprises an injector body, a plunger rod, a hub clip and a tamper-evident band.

According to another embodiment, the injector device comprising the injector body, plunger rod, hub clip and tamper-evident band are manufactured in a multi-shot mold process.

According to another embodiment the injector body, plunger rod, hinge clip and tamper-evident band are mode of materials that preclude mechanical or chemical bonding between adjoining components.

According to one embodiment, the injector body has a side wall having proximal and distal end portions and inner and outer surfaces. The inner surface of the injector body defines a cavity configured to receive at least a portion of a pharmaceutical cartridge therein. The injector body further includes one or more retention members disposed on the outer surface of the body.

According to another embodiment the retention members comprise a protrusion, such as a tenon, projecting radially outwardly from the outer surface of the injector body. In one embodiment the retention members have a dovetail-type configuration. In such embodiment the portion of the retention member proximal the outer surface of the injector body has a narrower cross-sectional width, generally being perpendicular to the longitudinal axis of the injector body, than the cross-sectional width of the portion of the retention member distal the outer surface of the injector body.

According to another embodiment, the retention members engage receivers on the plunger rod. In one embodiment the receivers comprise a mating dovetail-shaped cavity or mortise in the plunger rod.

According to another embodiment, the retention members are connected to the injector body in the first position of the plunger rod. In a second position of the plunger rod, wherein the plunger rod is axially displaced from the first position, however, the retention members are disassociated from the injector body. In one embodiment, the retention members comprise fracturable posts. In another embodiment the posts have a tab extending transversely therefrom for engagement with the plunger rod.

According to another embodiment, the plunger rod has proximal and distal end portions. The distal end portion of the plunger rod has a connection member constructed for connection to a connecting member associated with a piston positioned within the pharmaceutical cartridge. The plunger rod further has one or more receiving members between the proximal end portion and the distal end portion for cooperation with the retention members on the injector body.

According to another embodiment, the retention members and the receiving members are constructed to cooperatively retain the plunger rod to the injector body adjacent the outer surface of the injector body when the plunger rod is in a first position. Further, the retention members and the receiving members are constructed to cooperatively release the plunger rod from the injector body when the plunger rod is transitioned axially toward the distal end of the injector body to a second position.

According to another embodiment, the receiving members comprise apertures configured to fixedly receive the retention members. In one embodiment the apertures have resilient members with a flange extending therefrom that fixedly engage the tab to prevent reverse movement of the posts.

According to another embodiment, the retention members comprise one or more wing members spatially disposed on the outer surface of the injector body. The wing members each have a retaining tab for engaging the receiving members of the plunger rod. In another embodiment the receiving members on the plunger rod comprise one or more ledges for mating with the wing members.

According to another embodiment, the plunger rod further has a pushing surface for engaging the cartridge positioned within the cavity of the injector body. The pushing surface is constructed to move the cartridge body axially distally as the plunger rod is moved from the first position to the second position. Additionally, in one embodiment movement of the plunger rod from the first position to the second position releases the plunger rod from the injector body, and movement of the plunger rod from the first position to the second position simultaneously activates the pharmaceutical cartridge.

According to another embodiment, the pushing surface has a flange extending therefrom to create a cavity which receives a portion of the pharmaceutical cartridge to preclude access to a grommet at a proximal end of the cartridge.

According to another embodiment the pushing surface has a nub projecting transversely therefrom. The nub precludes access to a grommet at a proximal end of the cartridge. In a preferred embodiment, the nub extends partially into a proximal end portion of the cartridge positioned within the cavity of the injector body.

According to another embodiment, the distal end portion of the plunger rod has a connection member constructed to attach to a connecting member associated with a piston of the pharmaceutical cartridge for transitioning the plunger of the pharmaceutical cartridge. In one embodiment the connection member of the plunger rod has threads formed thereon. In such an embodiment the plunger rod can be threadably secured to a connecting member mounted on a piston associated with the cartridge. In an alternate embodiment the connection member of the plunger rod has a snap-fit member constructed to connect by snap fit to a connecting member mounted on a piston associated with a cartridge.

According to another embodiment, the pharmaceutical cartridge has a body portion defining an interior space. The interior space is fluidly sealed at a first, proximal end by a piston having a connecting member. The pharmaceutical cartridge is further fluidly sealed at a second, distal end by a pierceable diaphragm. The pharmaceutical cartridge further includes a hub slidably mounted on a distal end portion of the body portion. The hub includes a piercing member constructed to pierce the pierceable diaphragm sealing the second, distal end of the cartridge body portion. The cartridge is slidable relative to the hub between a first, inactivated position in which the piercing member is positioned distal to the pierceable diaphragm and in which the pierceable diaphragm fluidly seals the cartridge, and a second, activated position in which the piercing member is disposed through the pierceable diaphragm and wherein a flow channel defined by the piercing member is in fluid communication with the interior space defined by the pharmaceutical cartridge, thereby allowing the contents of the interior space to be ejected from the cartridge through the piercing member by moving the piston toward the distal end portion of the cartridge body.

According to another embodiment, the hub is fixed in place in the cavity of the injector body with a clip. In one embodiment, the clip has projections that extend through openings in the side wall of the injector body to engage the hub to prevent axial and radial movement of the hub.

According to another embodiment, the clip is rotatedly connected to the injector body, and the clip is rotatable from a first position wherein the clip is positioned outside the cavity of the injector body, and a second position wherein a portion of the clip is positioned within the cavity of the injector body to retain the hub of the pharmaceutical cartridge.

According to another embodiment, the injector body further comprises transverse finger grips extending from the proximal end portion of the injector body. Additionally, the injector body also has grip openings in the sidewall of the injector body. The grip openings are positioned on the distal end side of finger grips. The grip openings assist the user in activating the cartridge and dispensing the pharmaceutical product from the cartridge. The grip openings also allow the finger grips to have a decreased size.

According to another embodiment, the injector body is preferably clear or transparent, allowing the cartridge inserted into the cavity of the injector body to be visible through the sidewall of the injector body. In this manner, a bar code on the outer wall of the cartridge may be visible through the sidewall of the injector body and can be scanned through the sidewall when the pharmaceutical cartridge is seated in the injector body.

According to another embodiment, a combination of a pharmaceutical cartridge and an injector is provided. The combination includes a cartridge body defining an interior space for retaining a pharmaceutical product. A piston is positioned within the interior space defined by the cartridge body at a proximal end portion of the cartridge body. The piston fluidly seals a proximal end of the cartridge body portion. The piston has a connecting member associated therewith. The cartridge also has a pierceable diaphragm fluidly sealing a distal end portion of the cartridge body. The cartridge further includes a hub slidably mounted on the distal end portion of the cartridge body, the hub including a piercing member constructed to pierce the pierceable diaphragm. The piercing member defines a flow channel. The cartridge is slidably movable between a first, inactivated position in which the piercing member is disposed external to the interior space defined by the cartridge body portion and a second, activated position in which the piercing member is disposed through the pierceable diaphragm and in which the flow channel defined by the piercing member is in fluid communication with the interior space defined by the cartridge body, such that a pharmaceutical product disposed in the interior space defined by the cartridge body can be ejected through the flow channel defined by the piercing member by moving the piston toward the distal end portion of the pharmaceutical cartridge. The injector of the combination includes an injector body having a side wall having a proximal end portion and a distal end portion. The side wall has an inner surface and an outer surface, the inner surface of the side wall defining a space for receiving at least a portion of the cartridge body of the pharmaceutical cartridge therein. Preferably, though not necessary, either a clip or a portion of the injector body is constructed to prevent movement of the hub of the pharmaceutical cartridge in a distal direction when the pharmaceutical cartridge is disposed within the injector body. The injector also has one or more retention members disposed on the outer surface of the injector body. The plunger comprises a plunger rod having a proximal end portion and a distal end portion. The distal end portion of the plunger rod has a connection member constructed to attach to the connecting member associated with the piston of the pharmaceutical cartridge. The plunger rod has one or more engagement members formed along its length. In various embodiments the engagement members comprise surfaces, projections or receivers. The one or more engagement members and the one or more retention members are constructed to cooperatively retain the plunger rod on the injector body when the plunger rod is in a first position, and the one or more engagement members and the one or more retention members are constructed to cooperatively release the plunger rod from the body when the plunger rod is moved toward the distal end of the injector body to a second position. In another embodiment the plunger rod further includes a surface for engaging the proximal end portion of the cartridge body positioned within the injector body. The surface of the plunger rod is configured to move the proximal end portion of the cartridge body distally as the plunger rod is moved from the first position to its second position, whereby movement of the plunger rod from the first position to the second position releases the plunger rod from the injector body, and whereby movement of the plunger rod from the first position to the second position simultaneously activates the pharmaceutical cartridge. In this combination, at least a portion of the cartridge body is disposed within the injector body.

According to another embodiment, the one or more engagement surfaces formed along the length of the plunger rod are defined by a ledge. In one possible configuration of this alternative embodiment, the ledge includes notches spaced apart from each other that correspond to complementary retaining tabs provided on the injector body. To attach the plunger rod to the injector body, the plunger rod is placed over the wings with the notches aligned with the retaining tabs. The plunger rod is then moved proximally along the injector body so as to engage the ledge with the retaining tabs. To release the injector rod, the injector rod is moved distally relative to the injector body so as to place the notches in position opposite the retaining tabs on the wings. The injector rod can then be lifted from the injector body and the distal end of the plunger rod attached to a connecting member on a piston positioned with the pharmaceutical cartridge. The distal movement of the injector rod relative to the injector body also causes an engagement surface of the injector rod to move a proximal end portion of a pharmaceutical cartridge distally, thereby simultaneously activating the pharmaceutical cartridge.

According to another embodiment, the injector system has a visual indicator to indicate when the plunger rod has been manipulated to potentially compromise the integrity of the injector system. In one embodiment the visual indicator comprises a tamper-evident band.

According to another embodiment, the tamper-evident band has a first annular portion secured to the injector body, and a second portion secured to the plunger rod. The second portion secured to the plunger rod has a notched area to provide a fracture zone. Upon movement of the plunger rod with respect to the injector body the band will fracture at the fracture zone to provide a visual indication that the integrity of the system has been compromised.

Other features and advantages of the invention will be apparent from the following specification taken in conjunction with the following drawings.

BRIEF DESCRIPTION OF THE DRAWINGS

Example embodiments are illustrated in referenced figures of the drawings. It is intended that the embodiments and figures disclosed herein are to be considered illustrative rather than restrictive.

FIG. 1B is a side view of the injection device of FIG. 1A;

FIG. 1C is a bottom view of the injection device of FIG. 1A;

FIG. 3A is a top view of a plunger rod of FIG. 1A;

FIG. 3B is a side view of the plunger rod of FIG. 3A; and

FIG. 4B is a cross-sectional view of the injection device of FIG. 1 after activation of the ampoule;

FIG. 5 is a side view of the injection device of FIG. 1A with the plunger rod attached to the ampoule, the injection device ready for delivery of a pharmaceutical product contained within the ampoule;

FIG. 7A is a top view of one embodiment of a plunger rod;

FIG. 7B is a side view of one embodiment of a plunger rod;

FIG. 8A is a top view of one embodiment of an injector system with the plunger rod attached to the plunger of the pharmaceutical cartridge;

FIG. 8B is a side view of one embodiment of an injector system with the plunger rod attached to the plunger of the pharmaceutical cartridge;

FIG. 8C is a bottom view of one embodiment of an injector system with the plunger rod attached to the plunger of the pharmaceutical cartridge;

FIG. 8D is a side, cross-sectional view of an injector system in accordance with the present invention with the plunger rod attached to the plunger of the pharmaceutical cartridge;

FIG. 8E is a cross-sectional view of one embodiment of an injector system with the plunger rod attached to the plunger of the pharmaceutical cartridge;

FIG. 10A is a cross-sectional side view of one embodiment of an injector system after the plunger rod and plunger have been moved distally in order to eject pharmaceutical product from the pharmaceutical cartridge;

FIG. 10B is a cross-sectional side view of one embodiment of an injector system after the plunger rod and plunger have been moved distally in order to eject pharmaceutical product from the pharmaceutical cartridge;

FIG. 11D is a bottom cross-sectional view of one embodiment of the injector system prior to activation of the pharmaceutical cartridge;

FIG. 11E is a side cross-sectional view of one embodiment of the injector system prior to activation of the pharmaceutical cartridge;

FIG. 12C is an end view of the top and bottom mold cavities used in connection with the injector system;

FIG. 20 is a cross-sectional view about line 20-20 of FIG. 15;

FIG. 21 is a partial enlarged view of the retainer post of the injector system of FIG. 16;

FIG. 22 is a cross-sectional view about line 22-22 of FIG. 15;

FIG. 23b is a partial enlarged view of one embodiment of a retainer post of the injector body of FIG. 23a;

FIG. 24 is a top view of the injector body of FIG. 23a;

FIG. 31 is a cross-sectional view of one embodiment of the injector system in the activated position;

FIG. 32 is a cross-sectional view of one embodiment of the injector system with the plunger rod connected to the plunger;

FIG. 35 is a side elevation view of the injector system of FIG. 33;

FIG. 36 is a top plan view of the injector system of FIG. 33;

FIG. 37 is a cross-sectional view about line 37-37 of FIG. 36;

FIG. 38 is a front elevation view of the injector system without a pharmaceutical cartridge inserted therein, and with the clip rotated away from the injector body;

FIG. 39 is a first end elevation view of the injector system of FIG. 38;

FIG. 40 is a second end elevation view of the injector system of FIG. 38, taken from the plunger end of the injector system;

FIG. 41 is a top view of the injector system of FIG. 38;

FIG. 42 is a side elevation view of the opposing side of the injector system to that of FIG. 38;

FIG. 43 is a cross-sectional view about line 43-43 of FIG. 41;

FIG. 44 is a cross-sectional view about line 44-44 of FIG. 38, illustrating the tamper evident band;

FIG. 45 is a cross-sectional view about line 45-45 of FIG. 38, illustrating the connection of the clip to the injector body;

FIG. 46 is a cross-sectional view about line 46-46 of FIG. 38, illustrating the connection between the plunger rod and the injector body;

FIG. 47 is a perspective view of another embodiment of the injector body for use with the injector system of FIG. 38;

FIG. 48 is a side elevation view of the injector body of FIG. 47;

FIG. 49 is a bottom view of the injector body of FIG. 47;

FIG. 53 is a cross-sectional view about line 53-53 of FIG. 52;

FIG. 54 is a side elevation view of the plunger rod of FIG. 51;

FIG. 55 is an end view of the plunger rod of FIG. 51;

FIG. 56 is a bottom view of the plunger rod of FIG. 51;

DETAILED DESCRIPTION

Figure 1A:
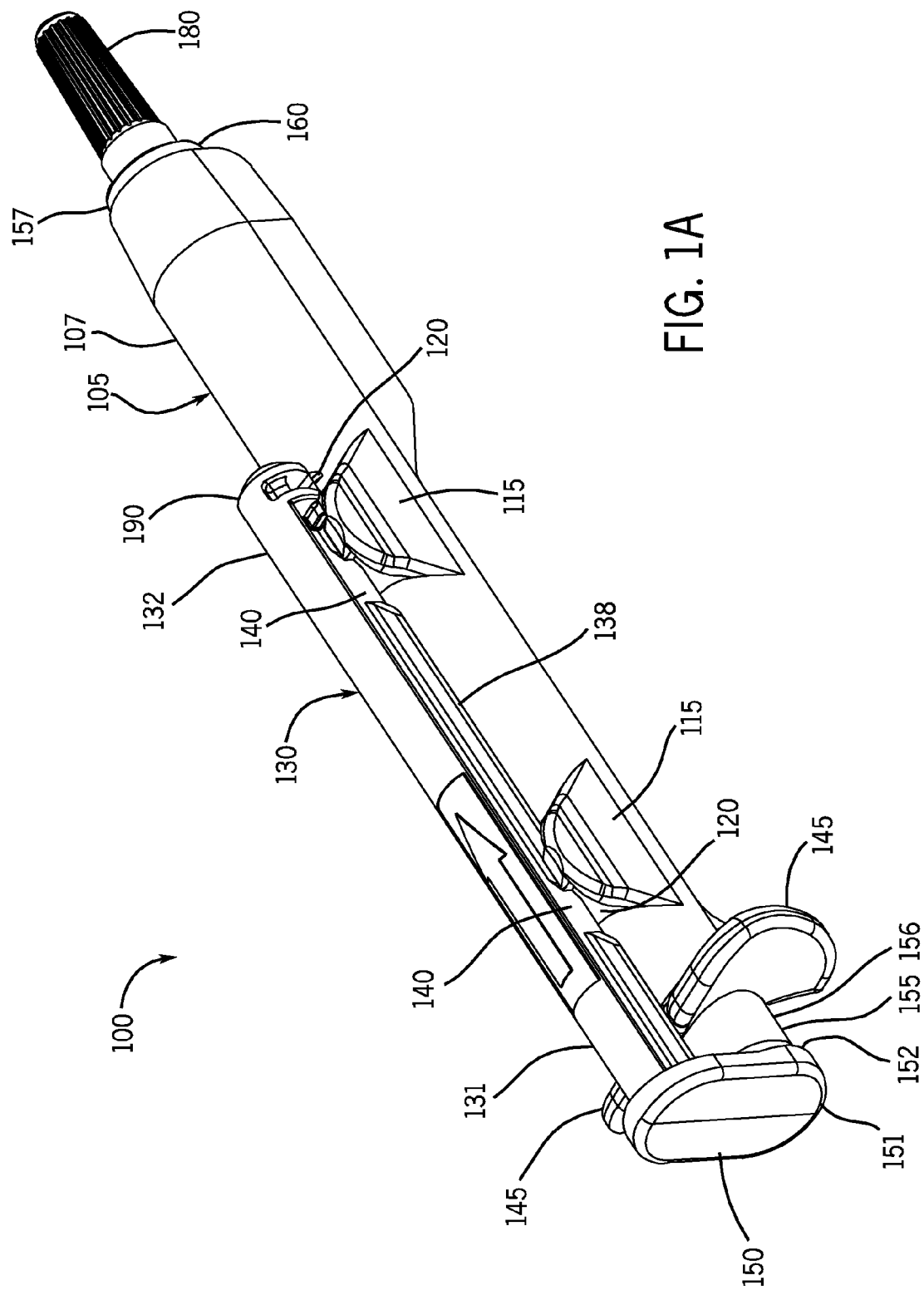
FIG. 1A is an isometric view of an injection device having an ampoule holder body receiving an ampoule and a rod attached to and carried by the body.

Referring now to FIGS. 1A-1C, an injector device 100 is illustrated comprising an injector body 105 for receiving and holding a pharmaceutical cartridge or ampule 155 containing a pharmaceutical product. As depicted in these figures, plunger rod 130 is mounted on injector body 105. As discussed in detail herein, plunger rod 130 is carried on the body 105 prior to activation of pharmaceutical cartridge 155. The body 105 includes a side wall 110 having an outer surface 115 and an inner surface 120. Although side wall 110 is depicted in the accompanying figures as being cylindrical in shape, it will be appreciated that the shape of side wall 110 can be varied based upon the shape of the pharmaceutical cartridge 155 to be used therewith. Inner surface 120 of side wall 110 defines a region or space 125 for receiving at least a portion of cartridge 155 therein. Injector body 105 has a proximal end portion 106 and a distal end portion 107. Plunger rod 130 has a proximal end portion 131 and a distal end portion 132. Cartridge 155 has a proximal end portion 156 and a distal end portion 157.

In one embodiment of the present invention depicted in the accompanying figures, injector body 105 is depicted as having a semi-circular cross-sectional configuration. Side wall 110 of injector body 105 defines a gap 111 along a length thereof. In the depicted embodiment of the present invention, gap 111 is sized such that pharmaceutical cartridge 155 can be inserted into side wall 110 of injector body 105 through gap 111. It will be appreciated that side wall 110 can be constructed of a flexible, resilient material such as plastic or metal such that pharmaceutical cartridge 155 can be inserted into side wall 110 through gap 111 despite the fact that the width of gap 111 is less than the overall diameter of pharmaceutical cartridge. In this way, side wall 110 of injector body 105 can be manufactured as a single piece. In an alternative embodiment, side wall 110 can be formed by two or more pieces connected by a hinge member, or by a living hinge, which enables the two or more pieces to be moved away from each other in order to enable pharmaceutical cartridge 155 to be inserted into side wall 110.

It will be appreciated that other methods for placing pharmaceutical cartridge 155 into side wall 110 can be employed and that side wall 110 need not have a gap 111 for allowing placement of the pharmaceutical cartridge 155 into side wall 110. For example, it is possible to construct side wall 110 such that pharmaceutical cartridge 155 is inserted therein from either the proximal or distal end of side wall 110. In such a configuration, retention portion 185 (discussed in detail below) will need to be configured such that pharmaceutical cartridge 155 can be slid therethrough, for example, by way of diametrically enlarging retention portion 185 or opening retention portion 185 as pharmaceutical cartridge 155 is slid therethrough, and such that retention portion 185 will subsequently interact with pharmaceutical cartridge 155 so as to prevent relative distal movement of hub 20 of pharmaceutical cartridge 155, as discussed in detail below. In one embodiment, gap 111 could be formed only through side wall 110 only adjacent to retention portion 185 of injector body 105, thereby allowing for the required diametrical enlargement of retention portion 185 as pharmaceutical cartridge 155 is positioned within side wall 110 of injector body 105.

Figure 2A:
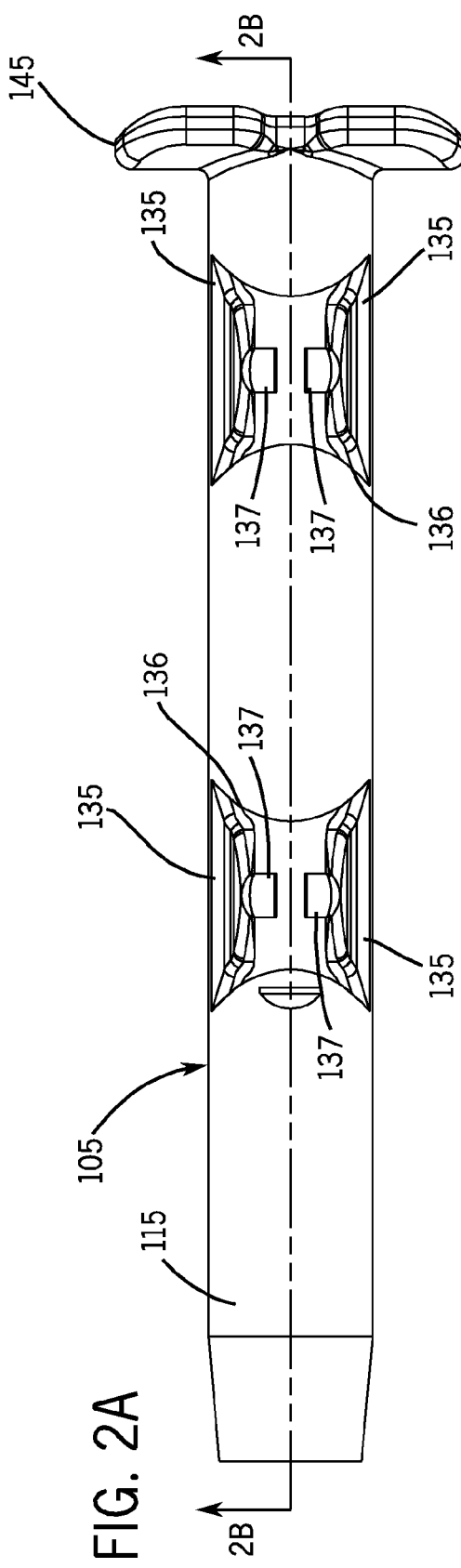
FIG. 2A is a top view of a body of the injection device of FIG. 1A.
Figure 2B:
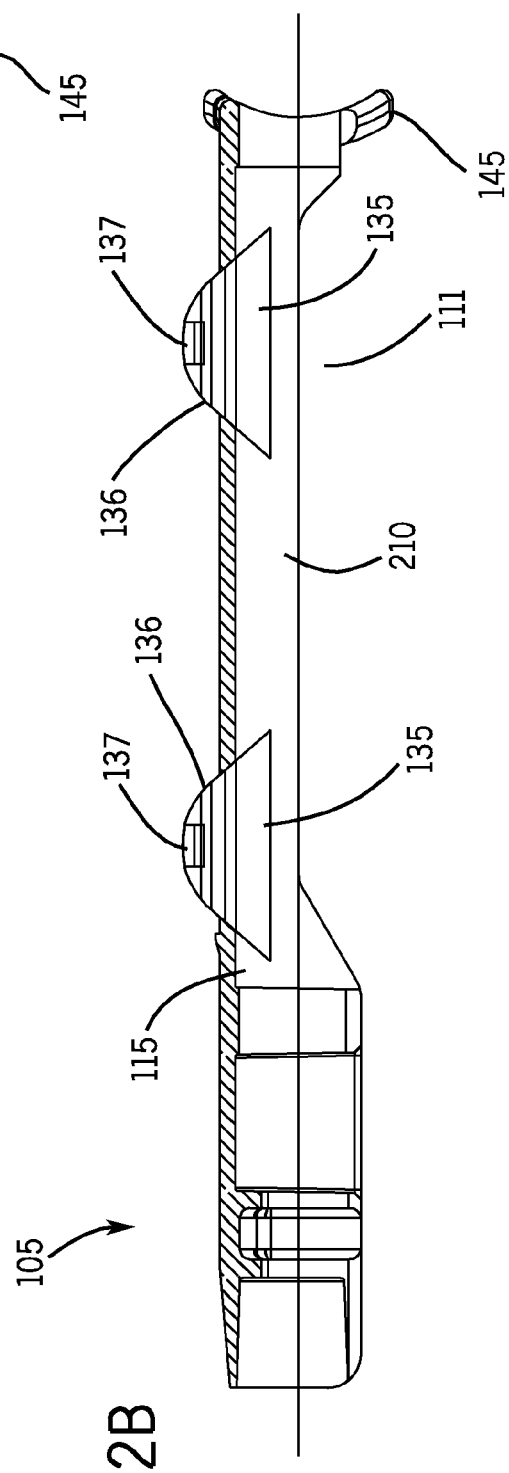
FIG. 2B is a cross-sectional view of the body of FIG. 2A.

As depicted in FIGS. 2A and 2B, injector body 105 includes one or more retention members 135 positioned on outer surface 115 injector body 105. In the embodiment of the present invention depicted in the accompanying drawings, retention members 135 are in the form of retaining wings 136 disposed on and projecting outwardly from outer surface 115 of side wall 110. Each of the wings 136 includes a respective retaining tab 137. Retaining tabs 137 are used to engage one or more complementary engagement surfaces 133 of plunger rod 130 to releasably attach plunger rod 130 to outer surface 115 of injector body 105. Said complementary engagement surfaces 133 are also defined as receiving members herein.

Figure 7C:
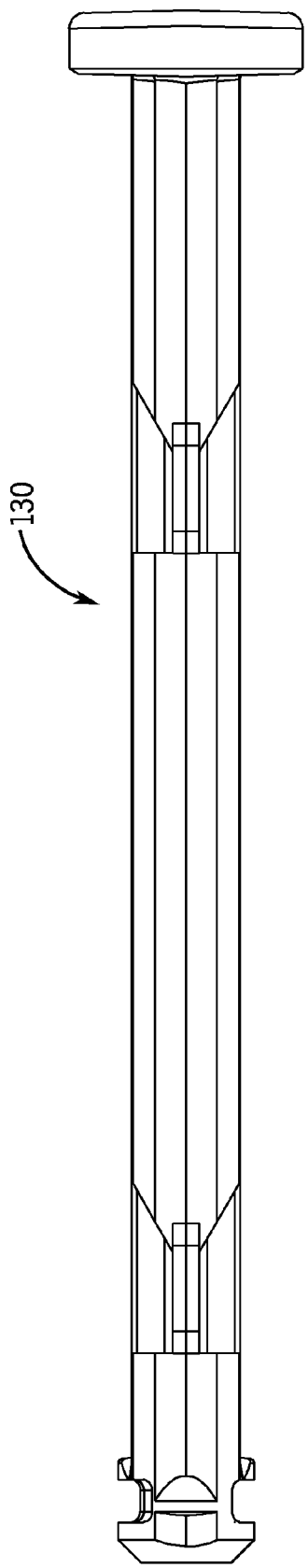
FIG. 7C is a bottom view of one embodiment of a plunger rod.
Figure 7D:
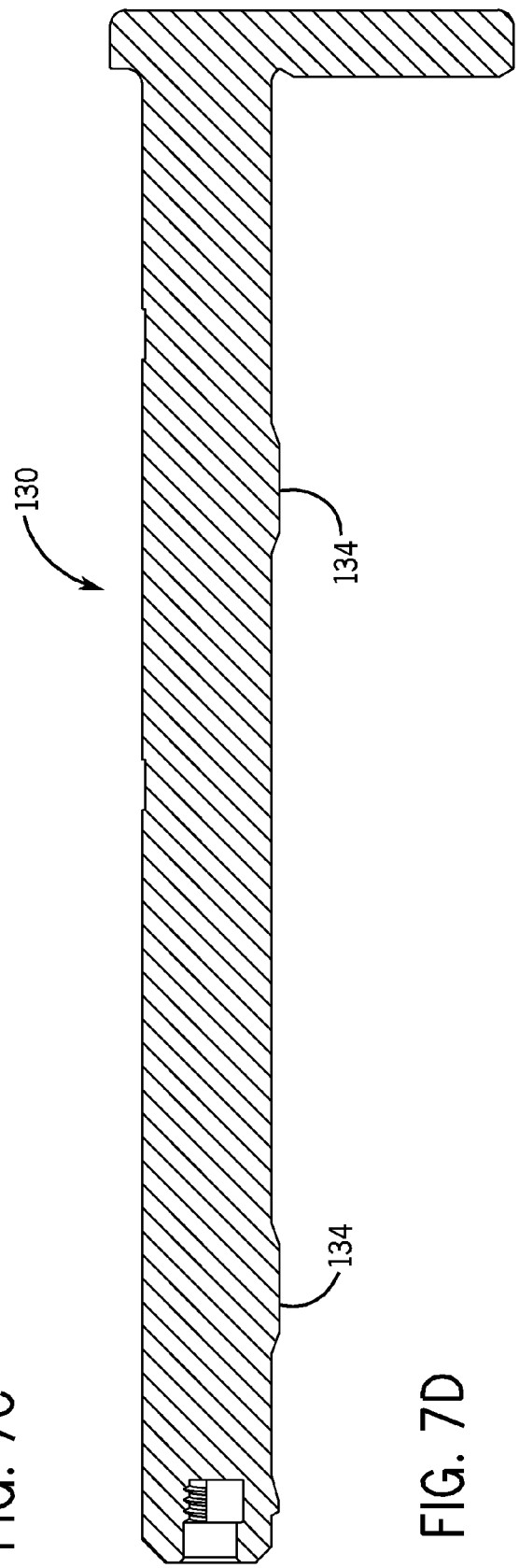
FIG. 7D is a cross-sectional view of one embodiment of a plunger rod.
Figure 7F:
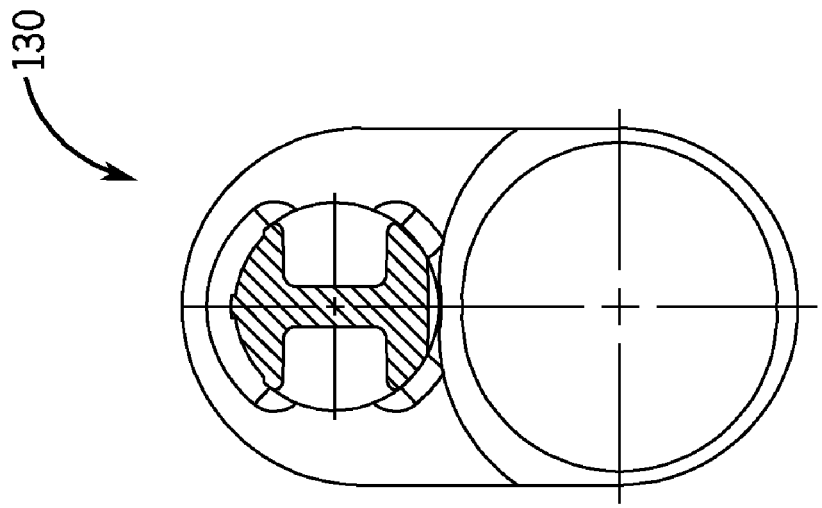
FIG. 7F is a cross-sectional view of one embodiment of a proximal end portion of a plunger rod.
Figure 7E:
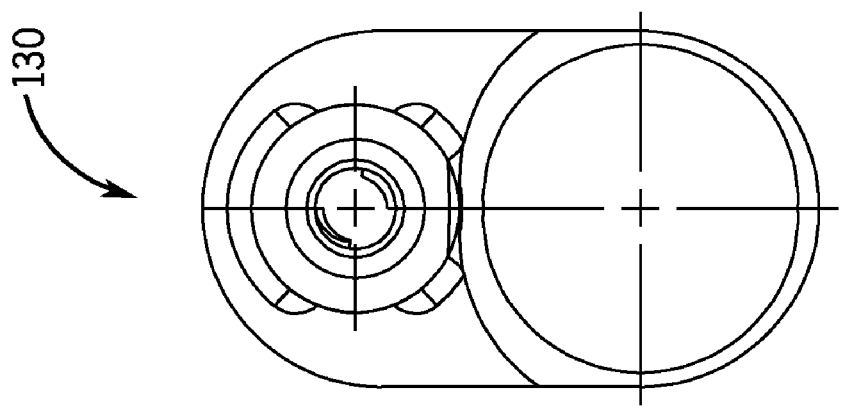
FIG. 7E is a view of a proximal end portion of one embodiment of a plunger rod.

In order to enhance the retention of plunger rod 130 by each of retention members 135, each of engagement surfaces 133 includes a radially enlarged portion 134, as depicted in FIG. 7D. It will be appreciated that the presence of radially enlarged portion 134 will enhance the frictional force with which retention members 135 and plunger rod engagement surfaces 133 interact, thereby improving the retention force with which plunger rod 130 is held on outer surface 115 of injector body 105.

In the embodiments of the present invention depicted in the accompanying figures, injector body 105 and plunger rod 130 are depicted as separate pieces. These pieces can be injection molded or formed using a variety of other known tooling techniques. It will be appreciated that injector body 105 and plunger rod 130 can be unitarily injection molded without departing from the intended spirit and scope of the present invention.

In one embodiment of the present invention, plunger rod 130 includes ledge 138 running along the length thereof. Ledge 138 is constructed to cooperate with retention members 135, particularly retention tabs 137, to releasably attach plunger rod 130 to injector body 105. Ledge 138 includes notches 140 defined therein along its length. When plunger rod 130 is positioned axially relative to injector body 105 such that notches 140 are aligned with retaining tabs 137 on wings 136 of retention members 135, plunger rod 130 can be moved radially relative to injector body 105 without physical contact between ledge 138 and retention tabs 137. That is, when notches 140 are aligned with retaining tabs 137, plunger rod 130 can be removed from injector body 105 or plunger rod 130 can be placed in a position for attachment to injector body 105 because the width of ledge 138 at notches 140 is less than the spacing between tabs 137. When plunger rod 130 is positioned axially relative to injector body 105 such that notches 140 are not aligned with retaining tabs 137 on wings 136 of retention members 135, plunger rod 130 cannot be moved radially relative to injector body because the width of ledge 138 is greater than the spacing between tabs 137.

As depicted in FIG. 3B, ramp portions 141 provide a gradual transition between the width of ledge 138 at notches 140 and the width of ledge 138 at its broadest along the length of ledge 138. It will be appreciated that ramp portions 141 facilitate the attachment and release of plunger rod 130 from injector body 105. Although ramp portions 141 are depicted in the accompanying figures as having a constantly changing diameter along their length, it will be appreciated that ramp portions 141 can have other forms so long as they facilitate attachment and release of plunger rod 130. Ramp portions 141 can also be eliminated, if desired.

Plunger rod 130 is attached to injector body 105 by placing plunger rod 130 over injector body 105 and aligning notches 140 with retaining tabs 137 on wings 136 and passing retaining tabs 137 through notches 140. In this position, radially enlarged portion 134 of plunger rod 130, which is located adjacent to notch 140, is positioned between wings 136 and does not engage injector body 105. Plunger rod 130 is next moved proximally relative to injector body 105, thereby causing ledge 138 to be positioned radially inwardly (beneath) retention tabs 137. As ledge 138 moves beneath retention tabs 137, radially enlarged portion 134 of plunger rod 130 comes into engagement with outer surface 115 of injector body 105, thereby causing plunger rod 130 to move radially outwardly by a distance substantially equal to the thickness of radially enlarged portion 134. This radially outward movement causes ledge 138 to be brought into contact with the underside of retention tabs 137, thereby providing a frictional fit between retention tabs 137 and ledge 138.

Although the injector device 100 of the present invention is depicted in the accompanying figures as including two retention members 135, e.g., two wings 136 having retention tabs 137, it will be appreciated that a single retention member 135 can be used to secure plunger rod 130 to outer surface 115 of side wall 110 of injector body 105. Further, it will be appreciated that more than two retention members 135 can be used to secure plunger rod 130 to outer surface 115 of side wall 110 of injector body 105. Similarly, the details of the construction of retention members 135 set forth herein are not intended to be limited to the wing and retention tab depicted in the accompanying drawings. One of ordinary skill in the art will recognize that various modifications can be made to the number and configuration of retention members 135 without departing from the spirit and scope of the present invention. In short, the accompanying figures are intended to be illustrative, not limiting, with respect to the configuration and number of retention member 135 of the present invention.

As depicted in FIGS. 1A-1C, injector body 105 includes finger grips 145. Finger grips 145 are configured such that a medical professional using injector device 100 of the present invention will engage them with his/her index and middle fingers during normal use. In the embodiment of the present invention depicted in the accompanying figures, finger grips 145 are convex on a distal side of finger grips 145 and concave on a proximal side of finger grips 145. It will be appreciated that the size and shape of finger grips 145 can be modified without departing from the scope of the present invention.

Pushing member 150 is provided on proximal end portion 131 of plunger rod 130. Pushing member 150 includes a proximal surface 151 that is constructed for engagement with a medical professional's thumb. In use, a medical professional will grasp injector body 105 such that his/her index and middle fingers are in contact with a distal surface of finger grips 145 and such that his/her thumb is in contact with proximal surface 151 of pushing member 150.

Pushing member 150 also includes a surface for pushing 152 which is constructed to engage proximal end portion 156 of pharmaceutical cartridge 155 and to urge proximal end portion 156 of pharmaceutical cartridge distally as a medical professional squeezes his/her index and middle fingers towards his/her thumb. The importance of surface for pushing 152 will be described in greater detail later in this specification.

Injector body 105 can be provided separately from pharmaceutical cartridge 155 such that a medical professional, e.g., a pharmacist, inserts pharmaceutical cartridge 155 into injector body 105 immediately prior to use. Alternatively, injector body 105 and pharmaceutical cartridge 155 can be pre-assembled by a manufacturer or assembler and supplied in combination to medical professionals.

Pharmaceutical cartridge 155 used in conjunction with the present invention can have a variety of configurations. In one embodiment, pharmaceutical cartridge 155 is constructed in the manner described in U.S. Pat. No. 5,653,698 which has been incorporated herein by reference. Using many of the lead numbers set forth in U.S. Pat. No. 5,653,698, FIG. 1C depicts the details of pharmaceutical cartridge 155. Cartridge 155 is constructed to retain a pharmaceutical product within an interior space 40 defined by cartridge 155. Piston/plunger 52 is slidably positioned within the interior space 40 at proximal end portion 156 of pharmaceutical cartridge 155. Piston/plunger 52 fluidly seals proximal end portion 156 of pharmaceutical cartridge 155. A connection member 160, e.g., threaded rod, is attached to piston/plunger 52 such that it is accessible from the exterior of cartridge 155. Connection member 160 can have a variety of configurations, including that of a threaded rod constructed to engage a plunger rod having complementary threads formed thereon. Alternatively, connection member 160 can be a member constructed to provide a snap fit with a complementary connecting member formed on a plunger rod. Other configurations providing locking or frictional connections between connection member 160 and a complementary member on a plunger rod can also be used.

Figure 4A:
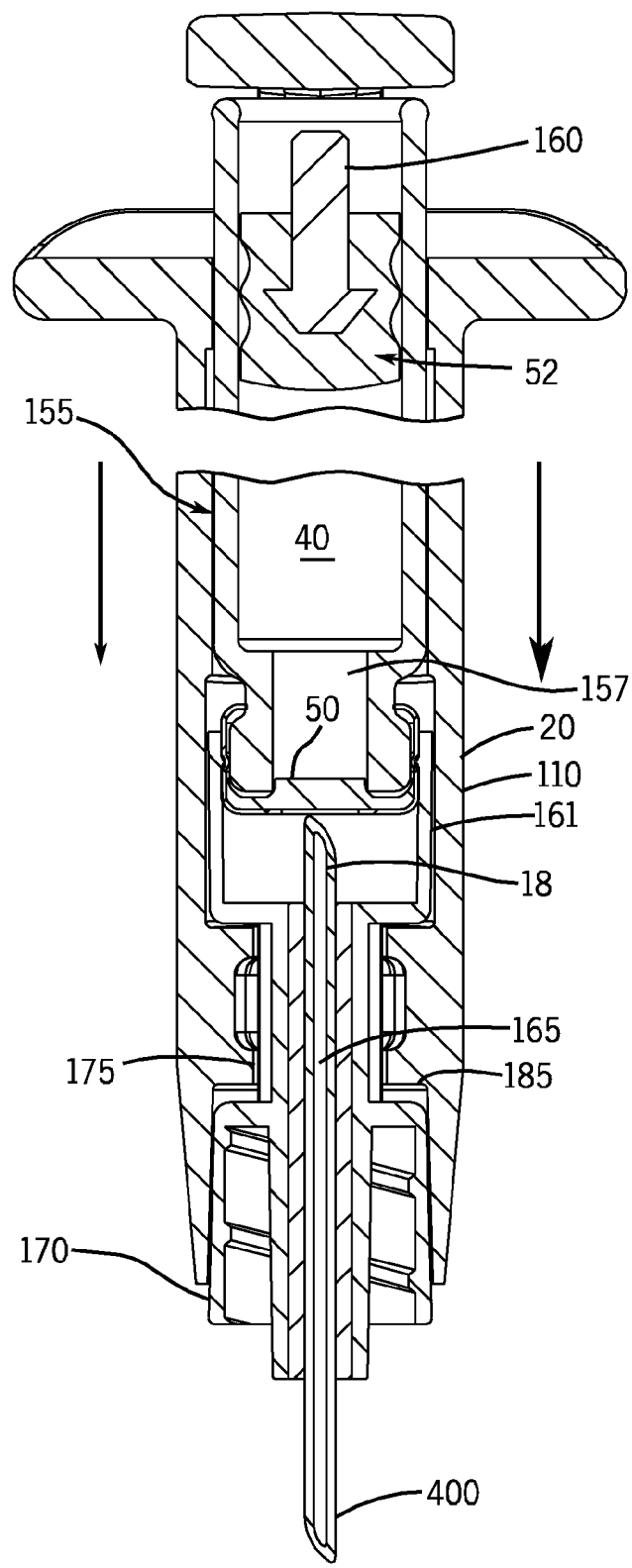
FIG. 4A is a cross-sectional view of the injection device of FIG. 1A prior to activation of the ampoule.

Distal end portion 157 of the cavity 40 of the cartridge 155 is fluidly sealed by pierceable diaphragm 50, as depicted in FIG. 4A. Pierceable diaphragm 50 can be constructed of a variety of known materials, including elastomeric materials that do not core when a piercing member is passed therethrough. Hub 20 is slidably mounted on cartridge 40 at distal end portion 157 of pharmaceutical cartridge 155. Hub 20 includes a piercing member (or needle cannula) 18 which is constructed to pierce pierceable diaphragm 50. Hub 20 is slidable between a first, inactivated position in which piercing member 18 is positioned outside of cartridge 155 and distally of pierceable diaphragm 50, and a second, activated position in which piercing member is disposed through pierceable diaphragm 50 and in which interior lumen 165 defined by piercing member 18 is in fluid contact with the contents in the cavity 40 of cartridge 155, thereby providing a pathway for the egress of fluids from cartridge 155 through piercing member 18 in response to pressure applied when piston/plunger 52 is moved distally.

Hub 20 includes a connecting portion 170 which is configured to deliver the pharmaceutical product contained in pharmaceutical cartridge 155 to a patient or to another medical apparatus, e.g., a tube set configured to deliver pharmaceutical products to a patient. As depicted in FIG. 4A, connection portion 170 is a threaded luer member constructed to connect with a complementary luer member. It will be appreciated that connection portion 170 can have a variety of configurations, including: (i) a hypodermic needle for delivery of pharmaceutical products directly to a patient or for delivery through a pierceable septum, e.g., a pierceable septum associated with an add port of a tube set or an add port of a flexible pharmaceutical container; (ii) a blunt needle for delivery of pharmaceutical products from pharmaceutical cartridge 155 to a medical device having the capability of receiving a pharmaceutical product from a blunt needle, e.g., a pre-slit elastomeric seal on a tube set or a flexible pharmaceutical container; (iii) threaded luer; and/or (iv) an unthreaded luer. Cap member 180 can be provided in order to cover connector 170 when injector device 100 of the present invention is not in use.

Figure 8F:
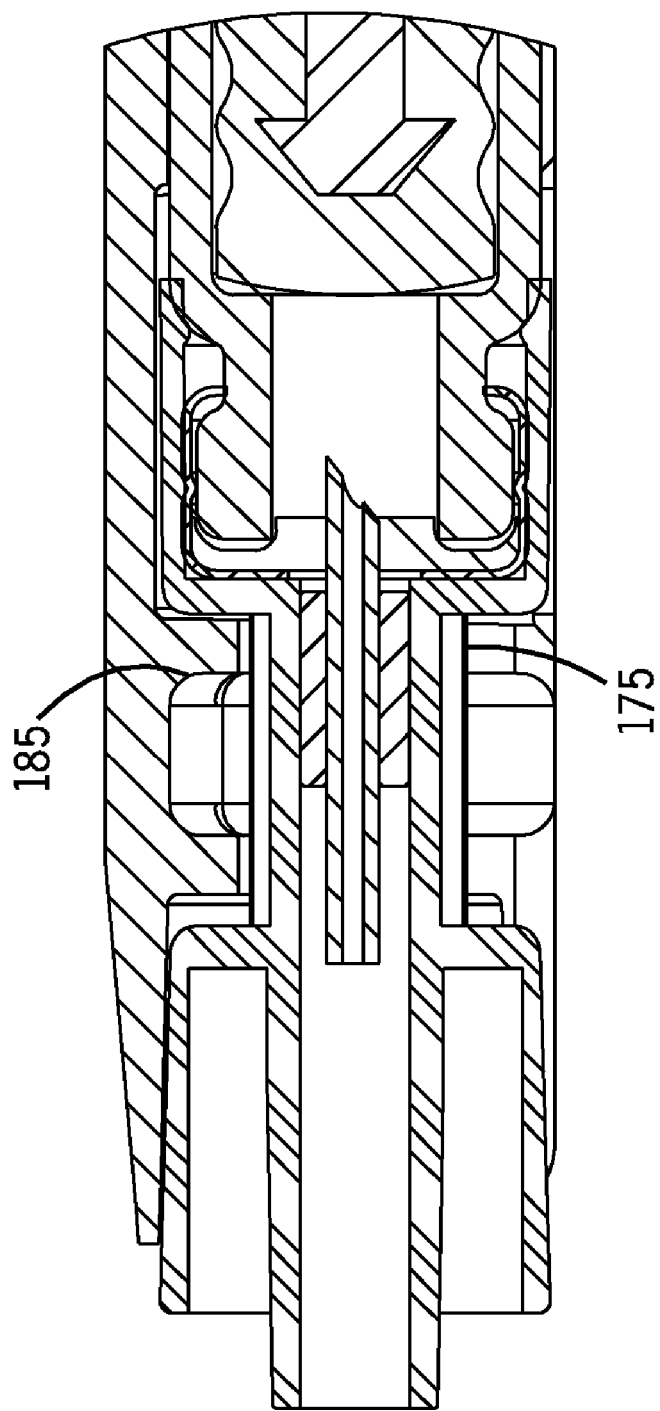
FIG. 8F is a cross-sectional view of one embodiment of a cartridge body and a hub of a pharmaceutical cartridge.
Figure 9A:
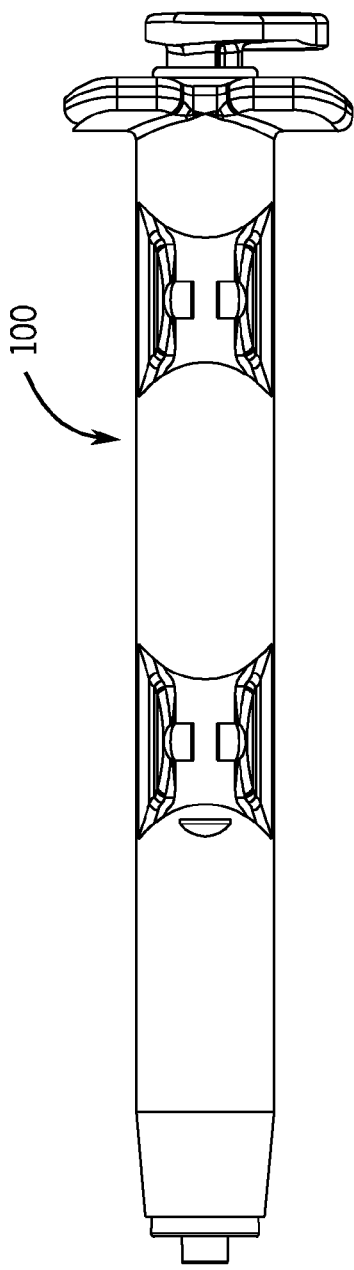
FIG. 9A is a top view of one embodiment of an injector system after the plunger rod and plunger have been moved distally in order to eject pharmaceutical product from the pharmaceutical cartridge.
Figure 9B:
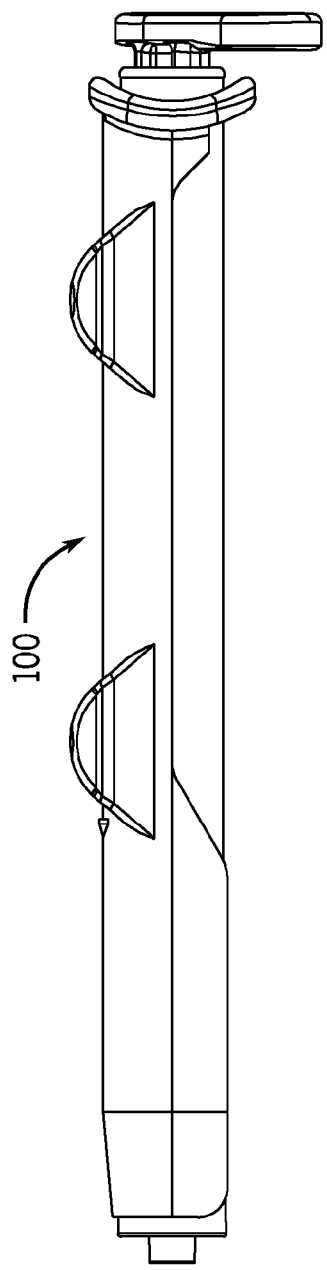
FIG. 9B is a side view of one embodiment of an injector system after the plunger rod and plunger have been moved distally in order to eject pharmaceutical product from the pharmaceutical cartridge.
Figure 9C:
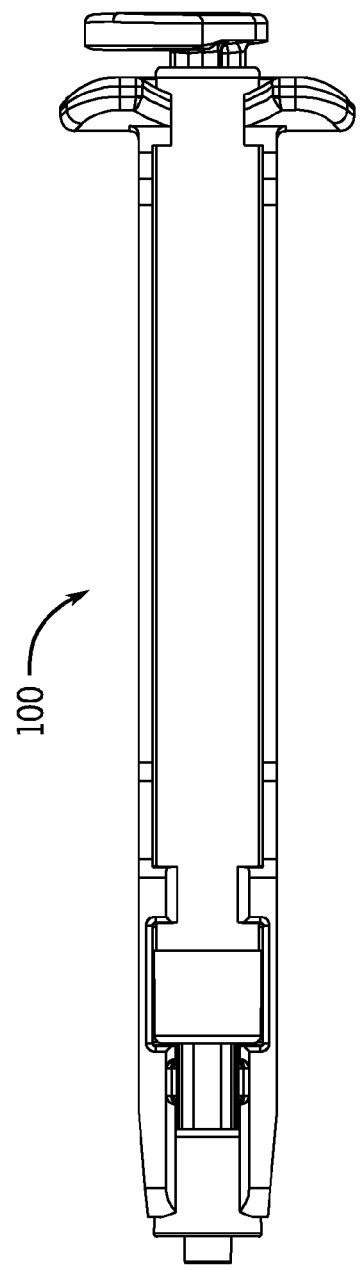
FIG. 9C is a bottom view of one embodiment of an injector system after the plunger rod and plunger have been moved distally in order to eject pharmaceutical product from the pharmaceutical cartridge.
Figure 10C:
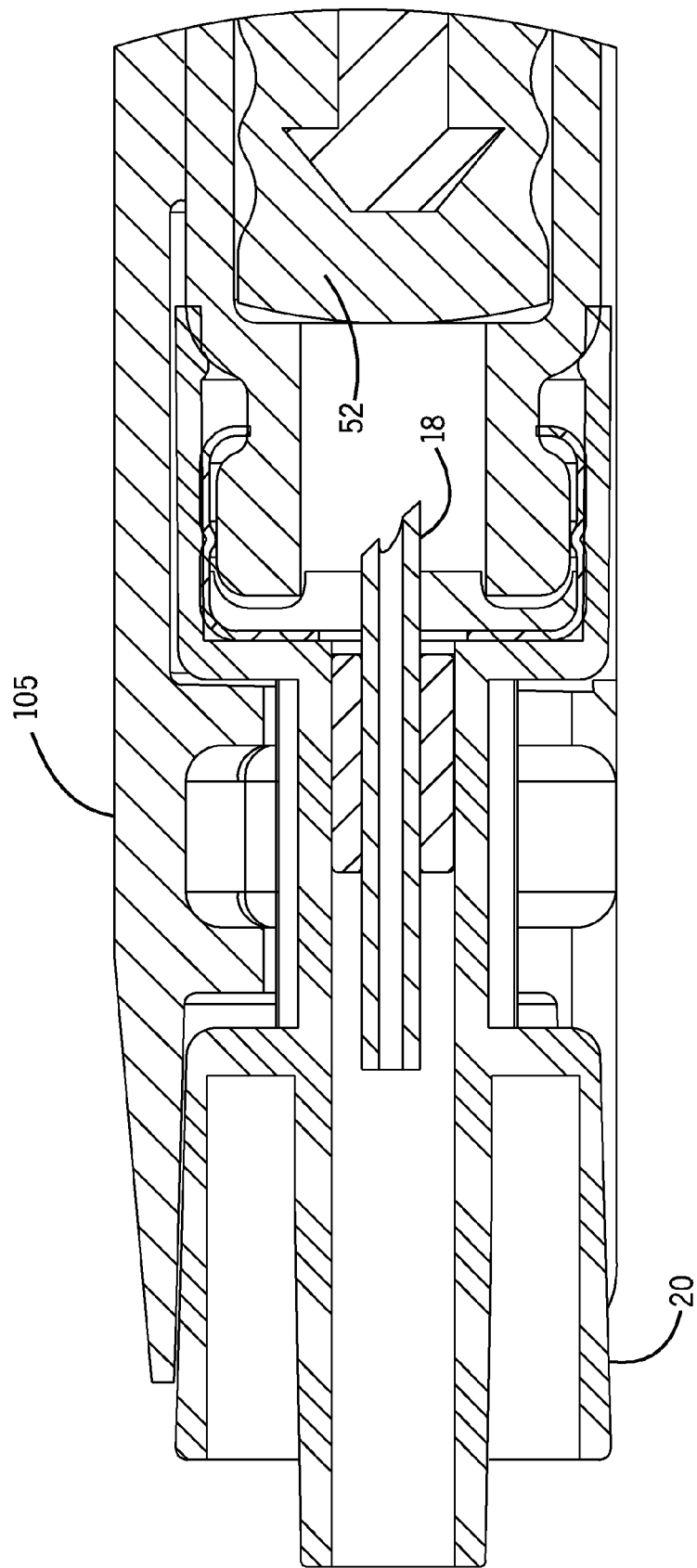
FIG. 10C is an enlarged cross-sectional view of one embodiment of the injector system after the plunger rod and plunger have been moved distally in order to eject pharmaceutical product from the pharmaceutical cartridge.
Figure 10F:
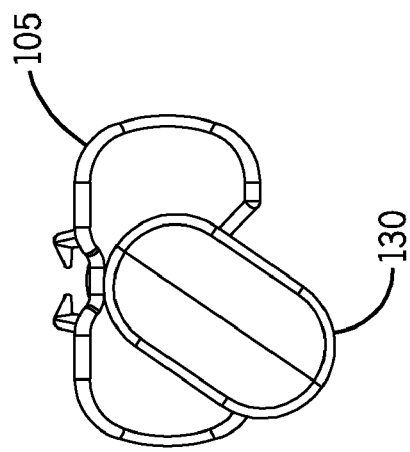
FIG. 10F is a rear end view of the injector system of FIG. 10D.
Figure 10E:
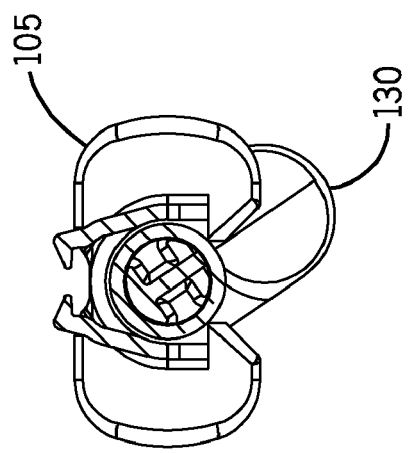
FIG. 10E is a cross-sectional end view an embodiment of the injector system of FIG. 10D.
Figure 10D:
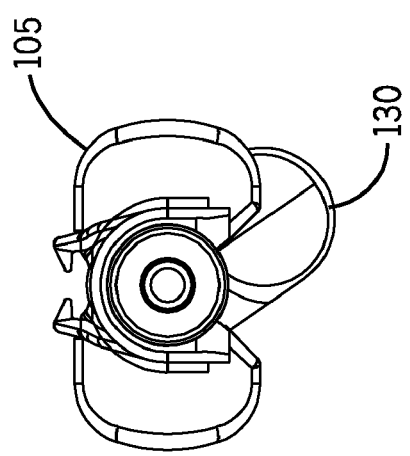
FIG. 10D is a front end view of an embodiment of the injector system without a plunger rod.
Figures 11A, 11B, 11C:
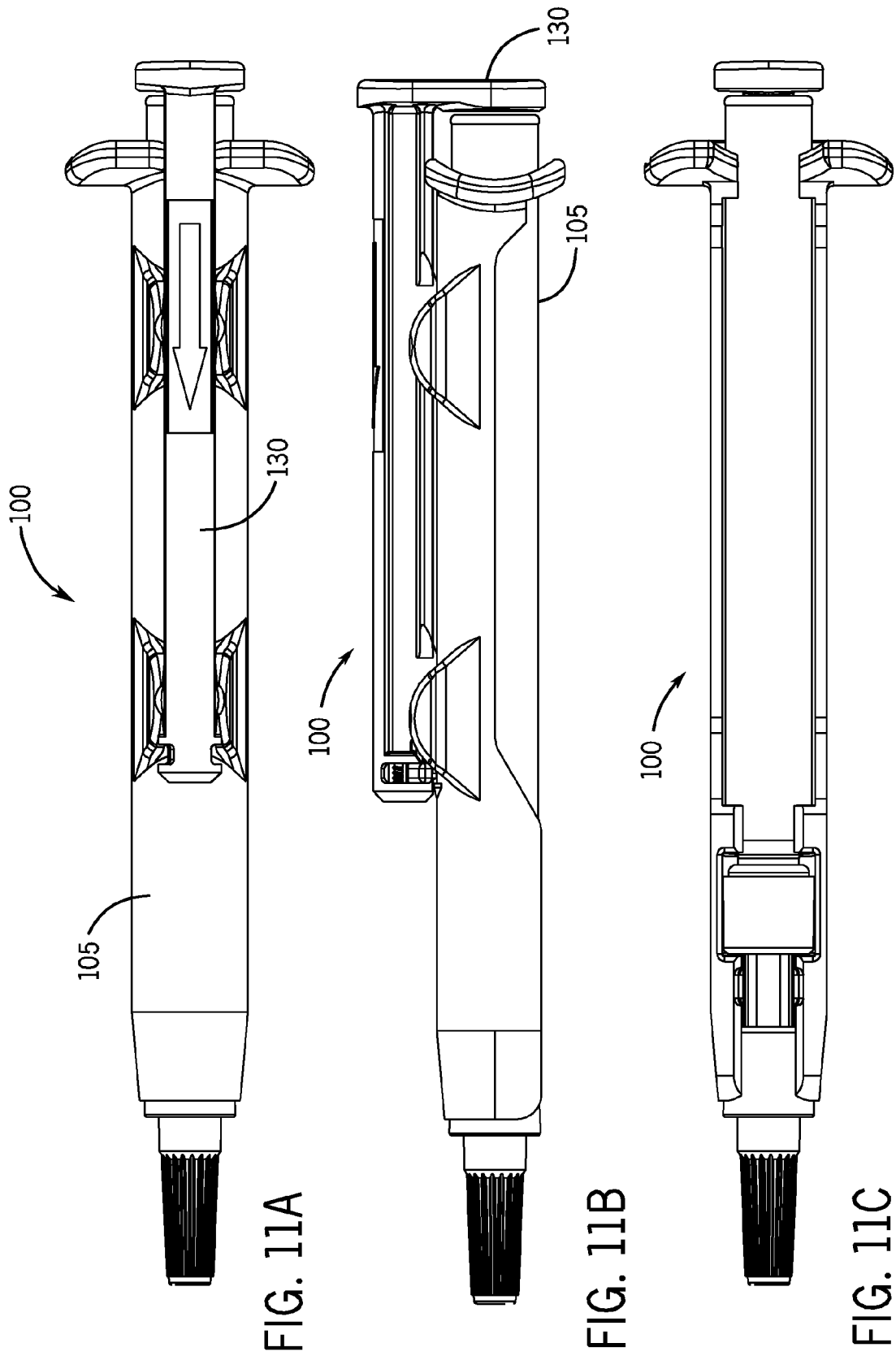
FIG. 11A is a top view of one embodiment of an injector system prior to removal of the plunger rod from the exterior surface of the injector body.
FIG. 11B is a side view of one embodiment of an injector system prior to removal of the plunger rod from the exterior surface of the injector body.
FIG. 11C is a bottom view of one embodiment of an injector system prior to removal of the plunger rod from the exterior surface of the injector body.
Figure 11F:
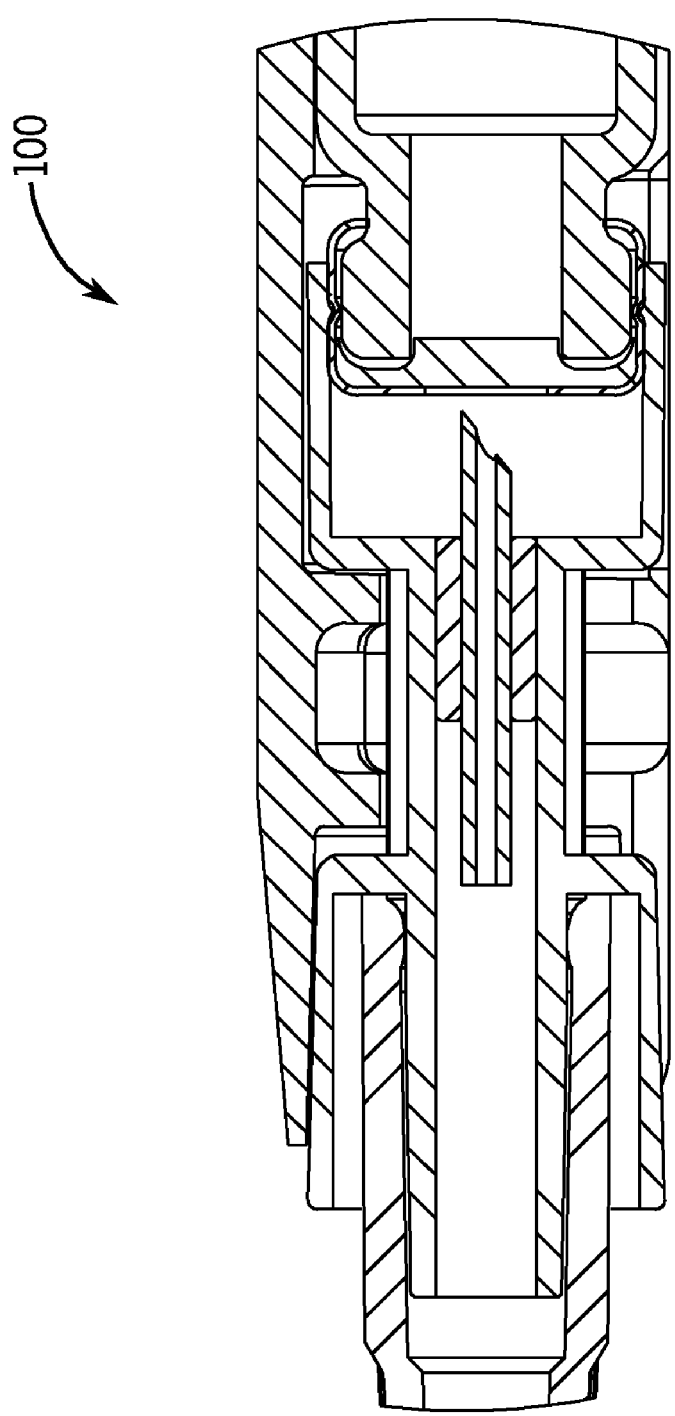
FIG. 11F is an enlarged partial cross-sectional view of one embodiment of the hub of the injector system prior to activation of the pharmaceutical cartridge.
Figure 11I:
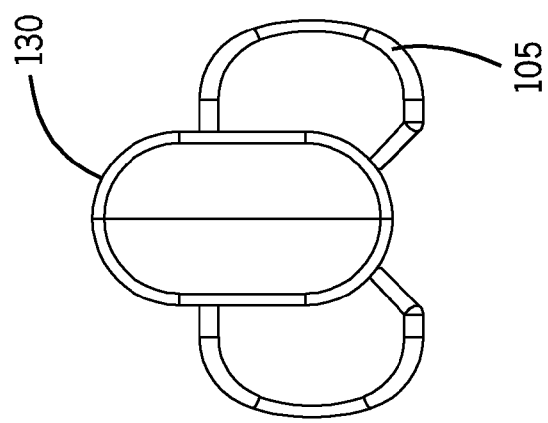
FIG. 11I is a rear end view of the injector system of FIG. 11G.
Figure 11H:
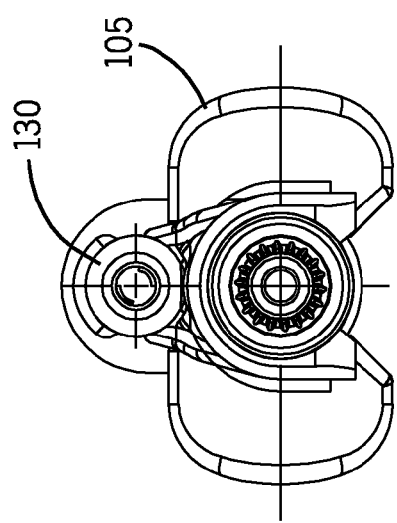
FIG. 11H is a front end view an embodiment of the injector system of FIG. 11G.
Figure 11G:
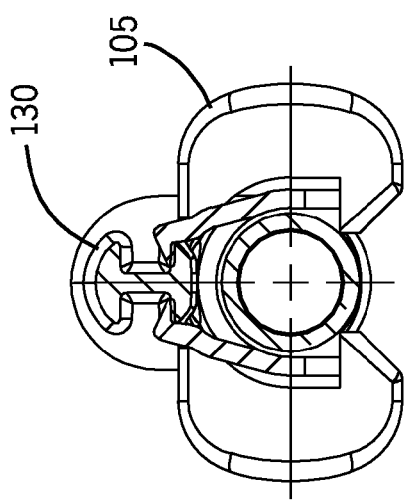
FIG. 11G is a cross-sectional end view of an embodiment of the injector system with a plunger rod.
Figure 12B:
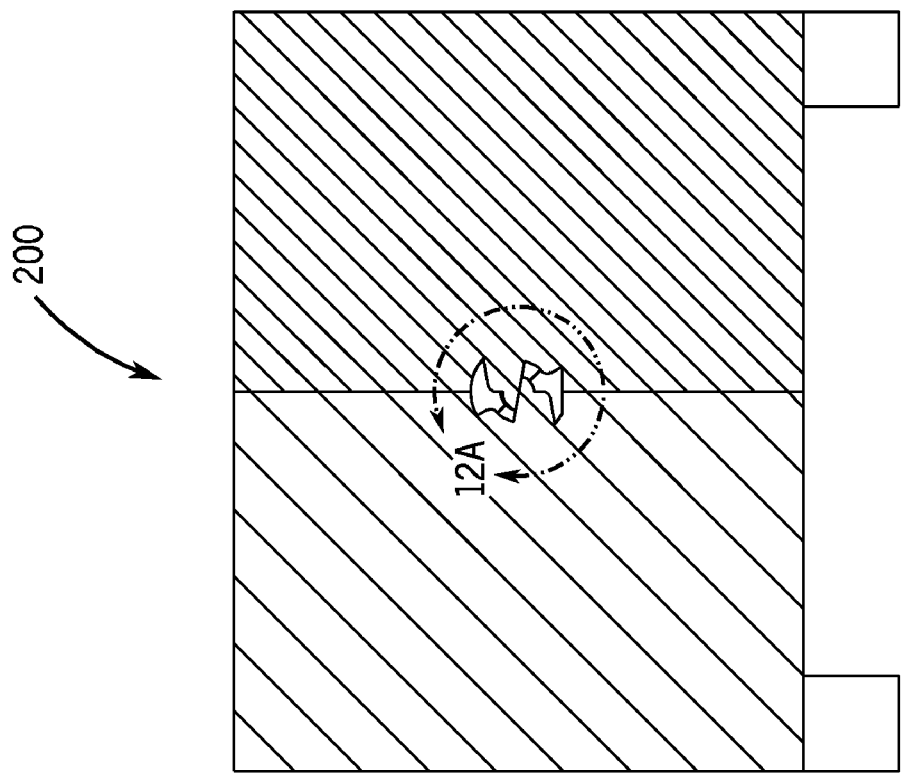
FIG. 12B is a detailed cross-sectional drawing of one embodiment of top and bottom mold cavities used in connection with the injector system.
Figure 12A:
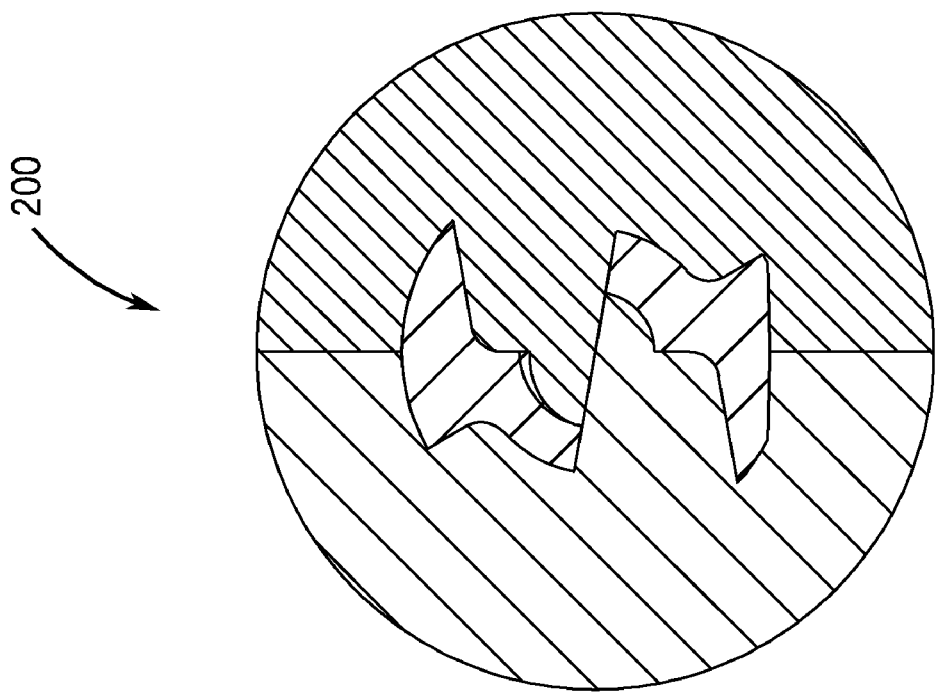
FIG. 12A is a detailed cross-sectional drawing of one embodiment of top and bottom mold cavities used in connection with the injector system.
Figure 12D:
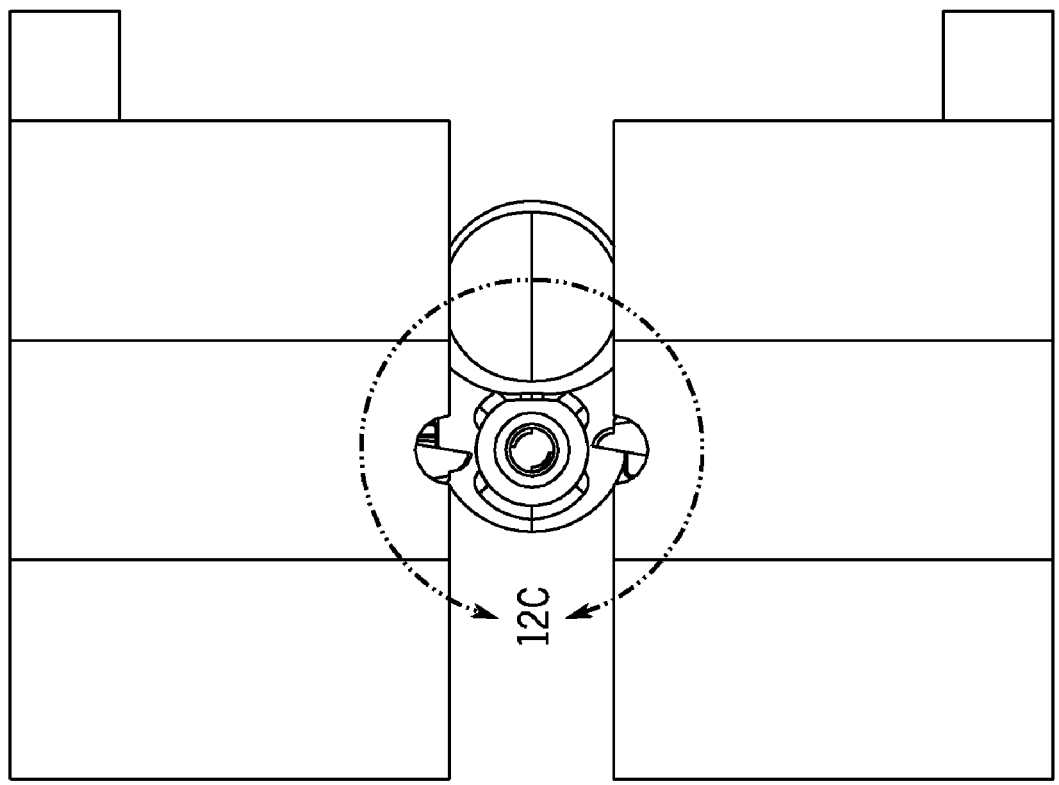
FIG. 12D is an end view of the top and bottom mold cavities used in connection with the injector system.
Figure 12F:
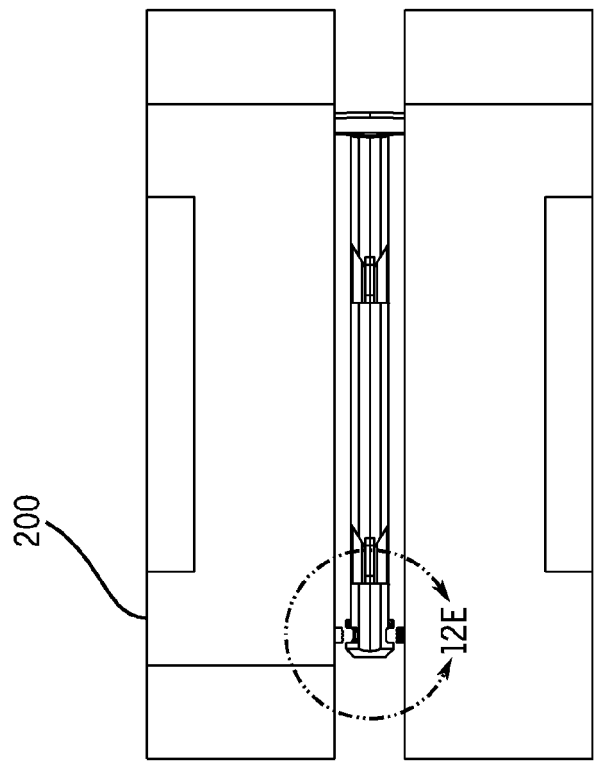
FIG. 12F is an end view of the top and bottom mold cavities used in connection with the injector system.
Figure 12E:
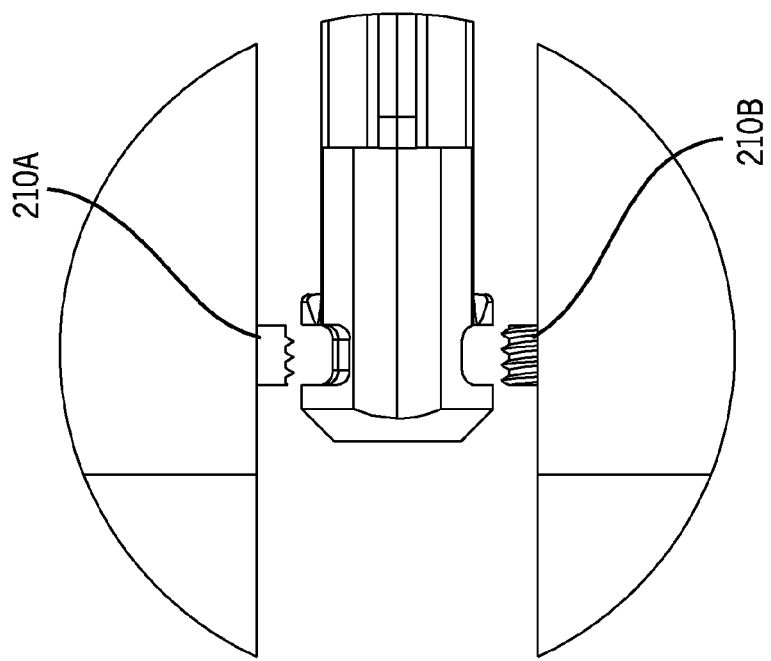
FIG. 12E is a side view of the top and bottom mold cavities used in connection with the injector system.

Hub 20 includes a necked-down portion 175, as depicted in FIG. 4A. As depicted in FIG. 8F, necked-down portion 175 of hub 20 is constructed to be positioned within retention portion 185 of side wall 110 at distal end portion 107 of injector body 105. When pharmaceutical cartridge 155 is positioned within side wall 110, necked-down portion 175 of hub 20 is positioned within retention portion 185. Retention portion 185 of side wall 10 precludes distal movement of hub 20. As depicted in the accompanying figures, a portion of hub 20 extends beyond side wall 110 of injector body 105 such that not all of pharmaceutical cartridge 155 is positioned within side wall 110 of injector body 105.

In order to use injector device 100 of the present invention, a medical professional will engage finger grips 145 with his/her index and middle fingers and will engage proximal surface 151 of plunger push surface 150 with his/her thumb. By squeezing his/her thumb and fingers together, plunger push surface 150 and finger grips 145 are moved closer to one another. Also by squeezing his/her thumb and fingers together, surface for pushing 152 applies a distal force on proximal end portion 156 of pharmaceutical cartridge 155. However, because retention portion 185 of side wall 110 precludes distal movement of hub 20, the application of a distally directed force on proximal end portion 156 of pharmaceutical cartridge 155 causes pharmaceutical cartridge 155 to move from its first, inactivated position toward its second, activated position. The squeezing force also causes plunger rod 130 to move distally relative to injector body 105 from its first, engaged position in which one or more notches 140 in ledge 138 are not aligned with the one or more retention tabs 137 of retention member(s) 135 to its second, released position in which one or more notches 140 in ledge 137 are aligned with the one or more retention tabs 137 of retention member(s) 135. In operation, pharmaceutical cartridge 155 is in its second, activated position when plunger rod 130 is in its second, released position.

Next, plunger rod 130 is removed from the exterior surface 110 of the injector body 105 and is positioned such that distal end portion 132 is adjacent to connection member 160 on piston/plunger 52. Where connection member 160 is a threaded member, a complementary connection member 190 having complementary threads is provided on distal end portion 132 of plunger rod 130 such that plunger rod 130 can be threadably attached to connection member 160 on piston/plunger 52, thereby enabling a user to move piston/plunger 52 proximally and/or distally through the application of proximally and/or distally directed forces to plunger push surface 150 and/or to plunger rod 130. As discussed above, connection members 160 and 190 can have a variety of configurations so long as they provide the desired attachment of plunger rod 130 to piston/plunger 52. For example, connection members 160 and 190 can be constructed to provide a friction or snap fit therebetween. Other configurations of connection members 160 and 190 will be readily appreciated by persons of ordinary skill in the art of the present invention.

After plunger rod 130 has been connected to piston/plunger 52 using complementary connection members 160, 190, a pharmaceutical product contained in pharmaceutical cartridge 155 can be delivered to a patient or transferred to another medical device by the application of a distally-directed force to plunger rod 130, e.g., through the application of a distally directed force to proximal surface 151 of plunger push surface 150. If desired, fluids can be aspirated into pharmaceutical cartridge at any time through the application of a proximally directed force to plunger push surface 150.

In most cases it will be preferable to construct pharmaceutical cartridge 155 from known glass materials due to the relative inactivity between glass and most pharmaceutical products. However, it will be appreciated that in certain cases it may be appropriate or necessary to use non-glass materials due to the possible interaction between the pharmaceutical product to be contained in pharmaceutical cartridge 155 and the material from which pharmaceutical cartridge 155 is constructed.

Injector body 105, including side wall 110, and plunger rod 130 can be constructed from a variety of known materials, including metals, plastics, and various known composites. In order to minimize cost, plastic may be preferable. A variety of known plastic materials providing the requisite rigidity and other performance characteristics can be used in conjunction with the present invention. Side wall 110 and plunger rod 130 need not be constructed of the same material.

In one embodiment of the present invention in which plunger rod 130 is constructed of a plastic material, connection member 190 includes a threaded recess formed on distal end portion 132 of plunger rod 130. In this embodiment, plunger rod 130 can be manufactured using a variety of known injection molding techniques. For example, the entirety of plunger rod 130 can be injection molded while a male threaded form is positioned at the distal end of the mold. The male threaded member in the mold will create a complementary female threaded recess in the distal end of the molded part. However, this approach to injection molding plunger rod 130 will require that the male threaded member be removed from the molded part by imparting relative rotational movement between the molded part and the male threaded member. This process can be time-consuming and require complex tooling when large volumes of plunger rods 130 are injection molded at high speeds.

In an alternative technique for forming plunger rods 130 having connection members 190 in the form of threaded recesses, a new injection molding technique has been developed. In this technique, a mold 200, depicted in FIGS. 12A-12G, is provided. Mold 200 defines all of the above-described features of plunger rod 130 (e.g., engagement surfaces 133, radially enlarged portion 134, ledge 138, and plunger push surface 150). The mold also includes complementary thread-forming members 210A and 210B. Thread-forming members 210A and 210B are constructed such that they create an aperture 220 through the diameter of plunger rod 130 at the distal end portion thereof (see FIG. 3A). Because thread-forming members 210A and 210B do not occupy the entire cross-sectional area of plunger rod 130, distal end portion 132 of plunger rod 130 is provided with side walls 225 that define aperture 220 through the distal end portion 132 of plunger rod 130 (see FIG. 3B). Because thread-forming members 210A and 210B have threads formed thereon, side walls 225 defining aperture 220 through plunger rod 130 have threads 226 molded therein. Core pin 230 also is included in the injection molding process in order to define an axial channel 235 through distal end portion 132 of plunger rod 130, axial channel 235 extending from the extreme distal end of plunger rod 130 to aperture 220. In use, a male threaded member, e.g., connection member 160 formed on piston/plunger 52, can be inserted into axial channel 235 defined in plunger rod 130 until the threads on the male threaded member come into contact with threads 226 defined on side walls 225 adjacent to aperture 220. The male threaded member can then be threadably secured to threads 226. As above-discussed, the use of complementary threaded members is merely illustrative of connection members 160, 190 that can be used in connection with the present invention. Other known approaches for providing the desired mechanical connection between plunger rod 130 and piston/plunger 52 will be understood and appreciated by those of ordinary skill in the relevant art.

One of the significant benefits from using mold 200 having thread-forming members 210A and 210 and core pin 230 arises in that plunger rod 130 does not need to be rotationally released from the molds after it has been formed. Instead, mold 200 is simply moved radially outwardly relative to the injection molded plunger rod 130 and core pin 230 is moved axially and distally relative to the injection molded plunger rod 130 in order to release plunger rod 130 from mold 200 and core pin 230. The elimination of the need to rotationally remove plunger rod 130 from mold 200 and/or core pin 230 is significant in high speed, high quantity manufacturing.

Figure 6A:
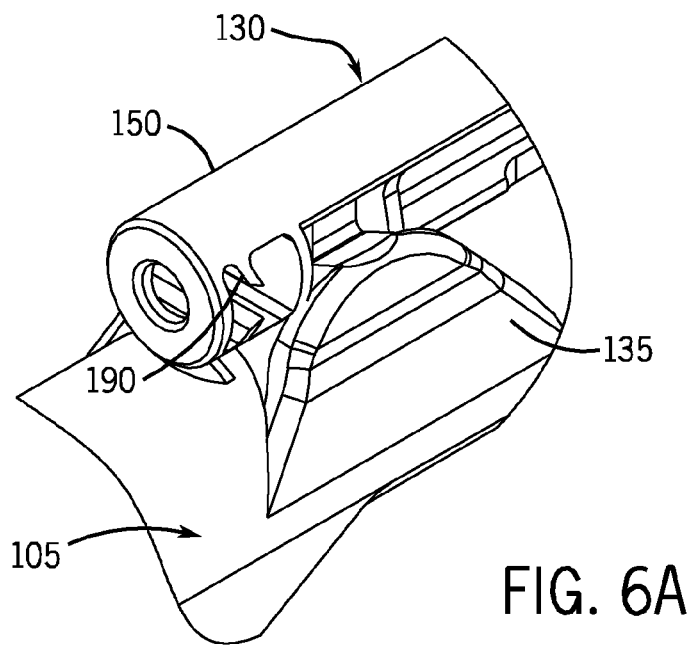
FIG. 6A is an isometric view of a second embodiment of the plunger rod in which the plunger rod has a different attachment mechanism for attaching the plunger rod to the ampoule plunger.
Figure 6B:
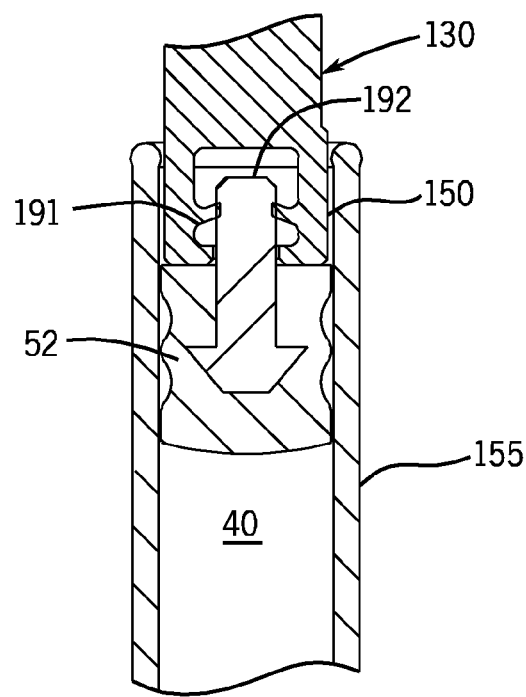
FIG. 6B is a cross-sectional view of the ampoule plunger attached to the plunger rod of FIG. 6A.

FIGS. 6A and 6B illustrate an alternative structure on the distal end of the rod 130 for attaching plunger rod 130 to piston/plunger 52. As shown in FIG. 6A, distal end portion 132 of plunger rod 130 includes a connection member 190 in the form of a pair of resilient flaps 191. Flaps 191 are constructed to engage a complementary barbed post 192 projecting from piston/plunger 52, as is illustrated in FIG. 6B. Those skilled in the art will appreciate that the configuration shown in FIG. 6 is offered by way of example and not limitation and that any number of other alternatives for attaching plunger rod 130 to piston/plunger 52 are possible.

Another embodiment of the injector device 100' is shown in FIGS. 13-32. This embodiment of the injector device 100' is adapted to receive and hold a pharmaceutical cartridge or ampule 155' containing a pharmaceutical product. The injector device 100' generally comprises a syringe or injector body 105', a plunger rod 130', a cartridge 155', a hub 20', a hub clip 21', a first hub cap 180' and a second cap 181'.

Figure 13:
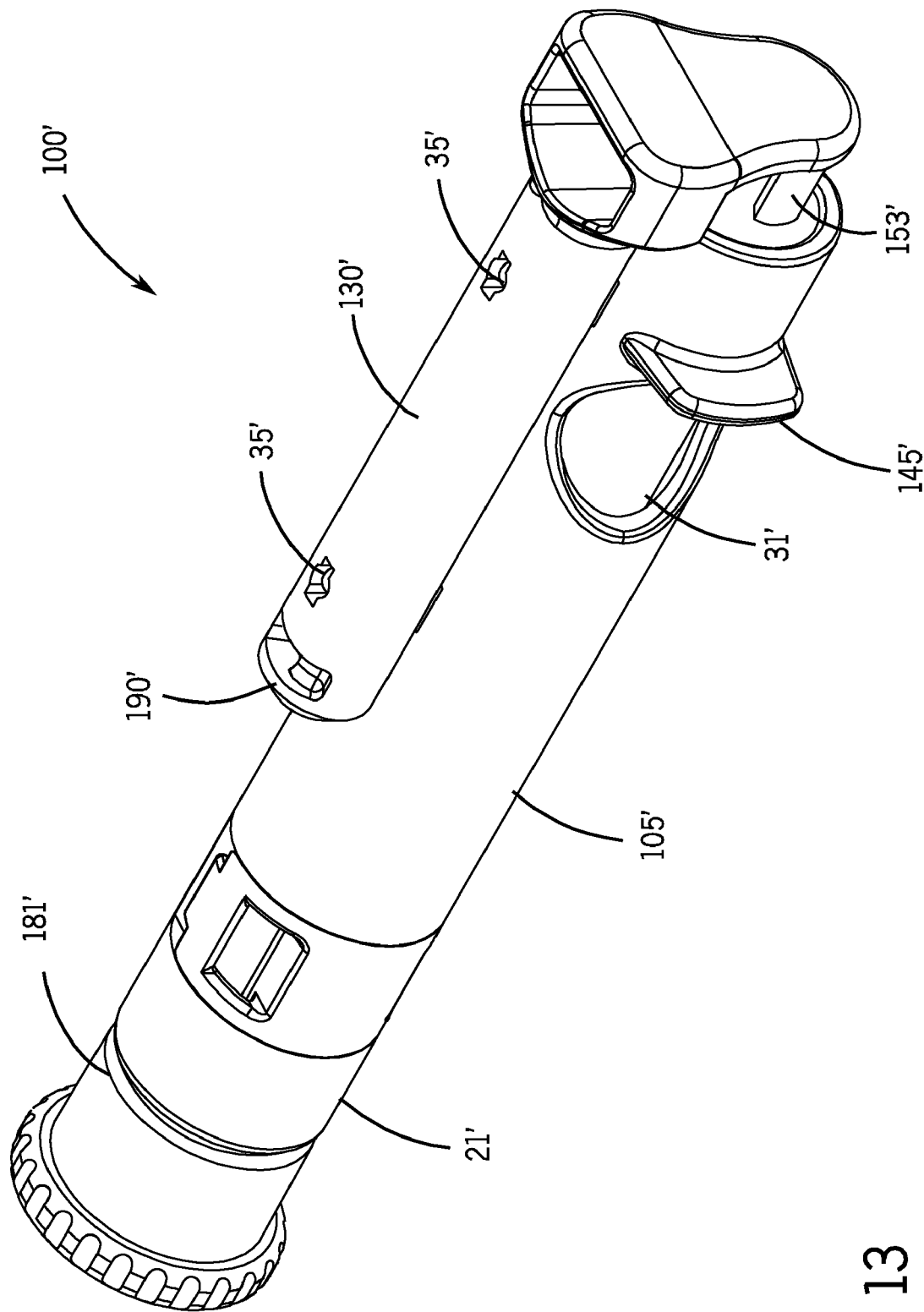
FIG. 13 is a perspective view of another embodiment of the injector system.

As shown in FIG. 13, the plunger rod 130' is mounted on injector body 105' in a first position. In this embodiment the injector body 105' has a sidewall 110' with an outer surface 115' and an inner surface 120'. In a preferred embodiment, the injector body 105' is preferably tubular in geometry. However, while the sidewall 110' is illustrated in the accompanying figures as being tubular or cylindrical in shape, it will be appreciated that the shape of side wall 110' can be varied for different purposes and to accept various shaped cartridges 155'. The inner surface 120' of side wall 110' defines a cavity or region 125' for receiving at least a portion of cartridge 155' therein.

The injector body 105' has a proximal end portion 106' and a distal end portion 107'. The injector body 105' further has a first opening 127' to the cavity 125' at the distal end portion 107' of the body 105', and a second opening 129' to the cavity 125' at the proximal end portion 106' thereof. As is shown in FIGS. 14-17, the injector body 105' also has a pair of grip openings 31' extending through the sidewall 110' and into the cavity 125'. As is explained in detail herein, the grip openings 31' assist the user in activating the cartridge 155' and dispensing the pharmaceutical product from the cartridge 155'. The grip openings 31' also allow the finger grips 145' to have a decreased size.

Figure 16:
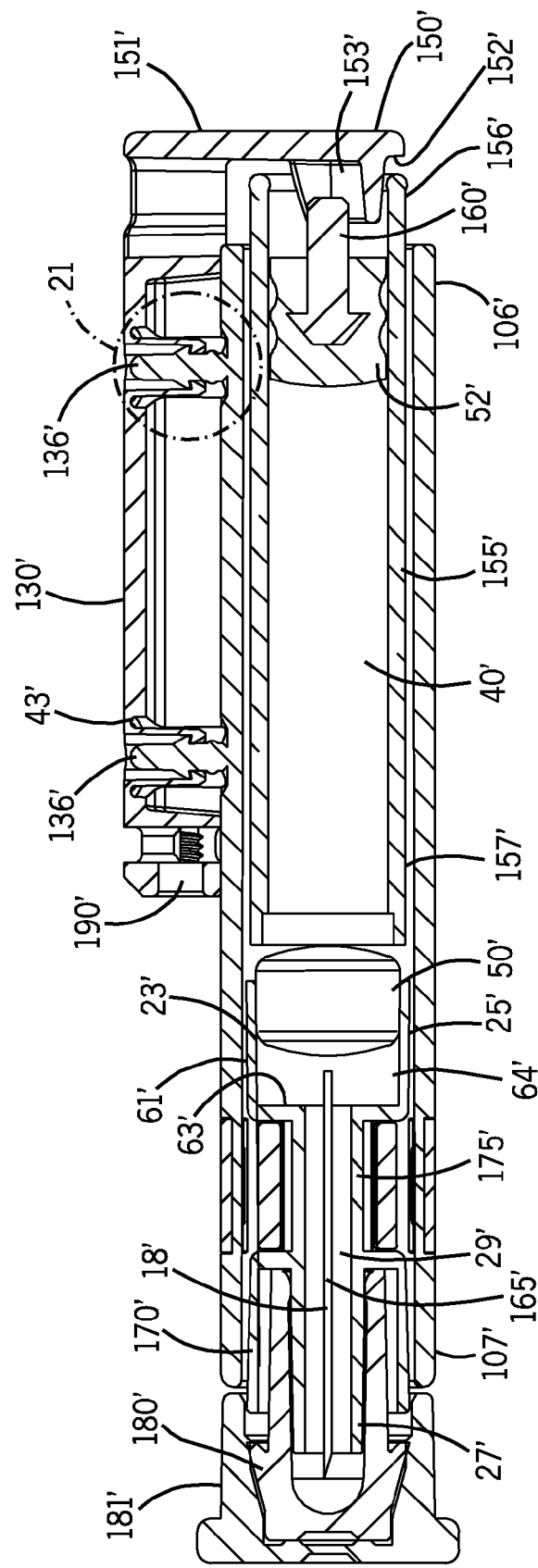
FIG. 16 is a side cross-sectional view about line 16-16 of FIG. 19.

In this embodiment the pharmaceutical cartridge 155' is typically inserted into the cavity 125' of the body 105' through the first opening 127' at the distal end 107' of the body 105'. In the inactivated position, as shown in FIG. 16, the cartridge 155' is fitted into the cavity 125' through the first opening 127', and pushed axially back toward the second opening 129'. As explained herein, the proximal end portion 156' of the cartridge 155' is generally positioned adjacent the pushing surface 152' of the plunger rod 130' in the inactivated position. Alternately, the pharmaceutical cartridge 155' can be inserted through an aperture in the sidewall 110' as described in the prior embodiment, or through the second opening 129' in the body 105'.

In a preferred embodiment the injector body 105' is preferably made of a plastic material, and preferably a generally rigid plastic material, such as acrylic or polystyrene. Additionally, the injector body 105' is preferably clear or transparent, allowing the cartridge 155' inserted into the cavity 125' of the injector body 105' to be visible through the sidewall 110' of the injector body 105'. In this manner, a bar code (not shown) on the outer wall of the cartridge 155' can be visible through the sidewall 110' of the injector body 105' and can be scanned through the sidewall 110' when the pharmaceutical cartridge 155' is seated in the injector body 105'. Alternately, the injector body 105' can be constructed of a flexible, resilient material such as more flexible plastic, or even a metal. In yet another alternative embodiment, injector body 105' can be formed by two or more pieces connected by a hinge member.

Figure 23A:
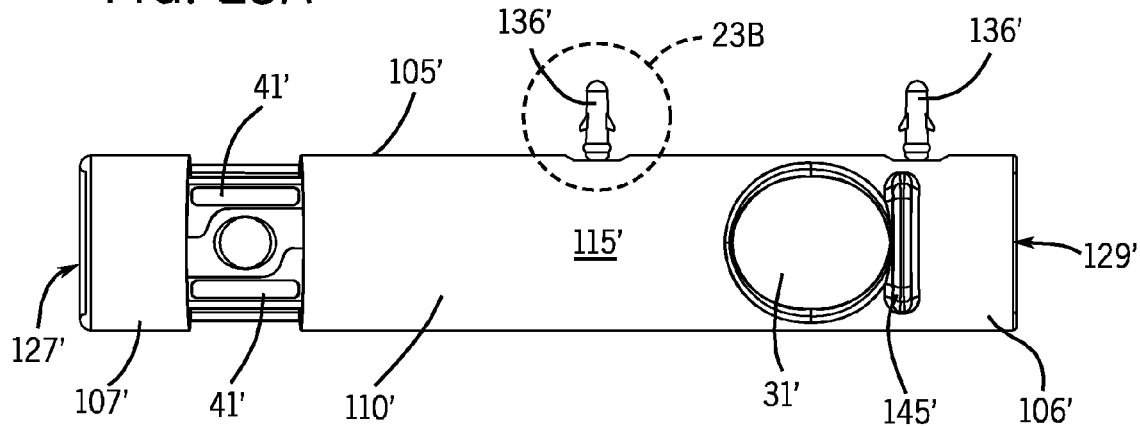
FIG. 23a is a side elevation view of one embodiment of the injector body of the injector system of FIG. 13.
Figure 23B:
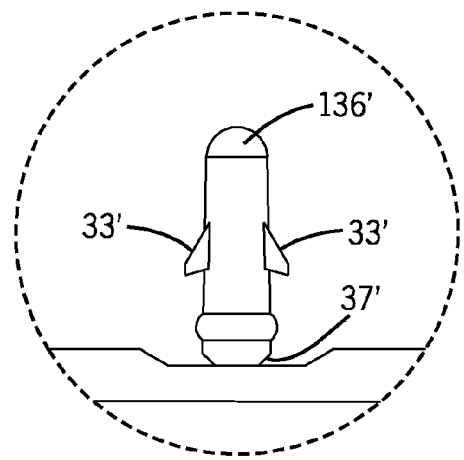
Figure 24:
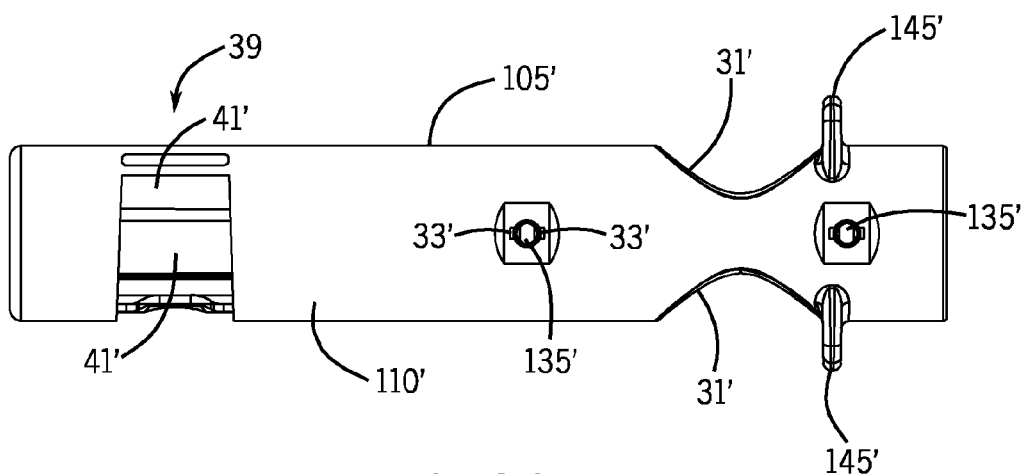
Figure 25:
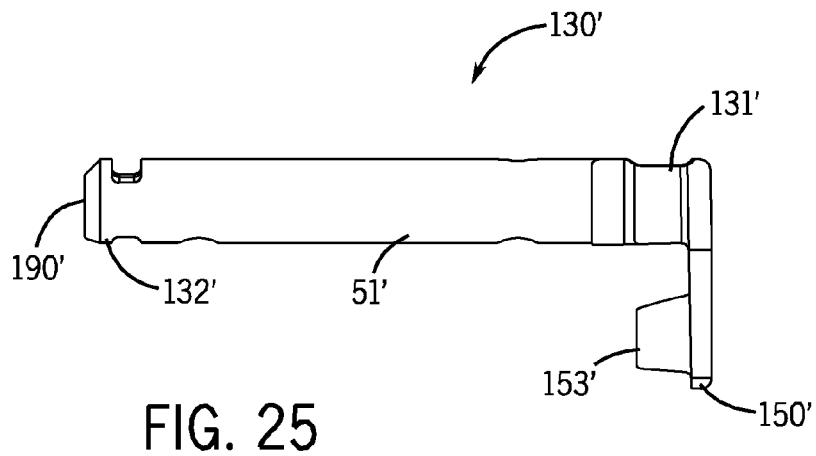
FIG. 25 is a side elevation view of one embodiment of a plunger rod for the injector system of FIG. 13.

As shown in FIGS. 23 and 24, the injector body 105' has one or more retention members 135' positioned on the outer surface 115' of the injector body 105'. In this embodiment the retention members 135' are utilized to fixedly retain the plunger rod 130' to the injector body 105' until usage of the syringe 100' of the cartridge 155'. As explained herein, in a preferred embodiment the plunger rod 130' cannot be removed from the injector body 105' unless the retention members 135' are broken from the injector body 105', thus providing tamper proof evidence of the security of the cartridge 155' for the syringe system 100'.

In a preferred embodiment, the retention members 135' comprise retention posts 136' projecting radially outwardly from the outer surface 115' of the injector body 105'. Further, in a preferred embodiment, two or more posts 136' are utilized, thereby fixedly retaining the plunger rod 130' in position until activation. Each of the posts 136' preferably have at least one tab 33' extending transversely therefrom, and preferably radially outwardly therefrom. As is explained herein, the tabs 33' are utilized to fixedly connect the retention members 135' to the retaining members 35' of the plunger rod 130' to secure the plunger rod 130' to the outer surface 115' of the injector body 105'. The post 136' also has a necked down portion 37' adjacent the outer surface 115' of the sidewall 110' of the injector body 105'. The necked down portion 37' has a smaller cross-sectional area that allows any force, and particularly transverse or axial forces by the plunger rod 130', to be concentrated at the necked down portion 37' such that the force necessary to shear the posts 136' for activation of the system 100' will be reduced.

Although the second embodiment of the injector system 100' is depicted in the accompanying figures as include two retention members 135', e.g., two retention posts 136' having tabs 33', it will be appreciated that a fewer number or greater number of retention members 135' can be used to secure the plunger rod 130' to outer surface 115' of side wall 110' of injector body 105'. Similarly, the details of the construction of retention members 135' and receiving or retaining members 35' set forth herein are not intended to be limited to the post and aperture configuration depicted in the accompanying drawings for the second embodiment of the injector system. One of ordinary skill in the art will recognize that various modifications can be made to the number and configuration of retention members 135' and receiving or retaining members 35' without departing from the spirit and scope of the present invention. In short, the accompanying figures are intended to be illustrative, not limiting, with respect to the configuration and number of retention member 135' and receiving or retaining members 35'.

The injector body 105' preferably includes finger grips 145'. Finger grips 145' are configured such that a medical professional using injector device 100' of the present invention will engage them with his/her index and middle fingers during normal use to push on the pusher member 150' of the plunger rod 130'. In one embodiment shown in FIGS. 23-24, the finger grips 145' are generally planer members extending from the outer surface 115' of the sidewall 110' of the injector body 105'. In this embodiment the finger grips 145' are positioned adjacent the respective grip openings 31' in the sidewall 110' of the injector body 105'. Further, in one embodiment the finger grips 145' are positioned approximately 90° apart from the retention posts 136'. Accordingly, when the user grips the injector body 105' with her fingers to push on the pusher member 150' of the plunger rod 130', the user's fingers do not engage the sidewall 110' of the injector body 105', but rather extend past the sidewall 110' of the injector body 105' and through the grip openings 31' and partially into the cavity 125' of the injector body 105'. Preferably, the cartridge 155' in the cavity 125' of the injector body 150' operates as a stop for the user's fingers. Thus, whereas in the prior embodiment the maximum distance between the end of the finger grips 145 to the radial finger stop is defined by the distance from the end of the finger grips 145 to the outer surface 115' of the sidewall 110' of the injector body 105', in this embodiment the maximum distance is defined by the distance from the end of the finger grips 145' to the outer surface of the cartridge 155'. Since the outer surface of the cartridge 155' is approximately 0.10" radially inward of the outer surface 115' of the sidewall 110' of the injector body 105', to have the same finger grip surface area as the prior embodiment each finger grip 145' can be approximately 0.10" shorter than the prior embodiment. This leads to nearly ¼" of savings in the overall width of the overall injector body 105' having finger grips 145'.

Alternatively, the finger grips may be convex on a distal side of finger grips and concave on a proximal side of finger grips to more closely match the geometry of a user's fingers. It will be appreciated that the size and shape of finger grips can be modified without departing from the scope of the present invention.

The injector body 105' also has a receiver 39' for receiving the hub clip 21'. The receiver 39' comprises a plurality of openings 41' through the sidewall 110' of the injector body 105'. In a preferred embodiment the receiver 39' is located toward the distal end portion 107' of the injector body 105'. The hub clip 21' is described in greater detail herein.

Referring now to FIGS. 25-30, the plunger rod 130' is shown. The plunger rod 130' has a body portion 51' with a proximal end portion 131' and a distal end portion 132'. The retaining members 35' are provided as part of the plunger rod 130'. The retaining members 35' are also referred to as receiving members 35'. In one embodiment, the retaining members 35' comprise retaining apertures 35'. In a preferred embodiment, a plurality of retaining apertures 35' are provided in the body portion 51' of the plunger rod 130', preferably between the proximal end portion 131' and the distal end portion 132' thereof. The retaining apertures 35' are constructed to cooperate with retention members 135', particularly the retention posts 136' having transverse tabs 33', to fixedly retain the plunger rod 130' to the injector body 105' until activation of the pharmaceutical cartridge 155'. In a preferred embodiment, the injector body 105' has two retention posts 136', and the plunger rod 130' has two corresponding retaining or receiving apertures 35'. Additionally, in a preferred embodiment the main body portion 51' of the plunger rod 130' has a generally C-shaped cross-section, with the outer convex surface of the body 51' facing radially outward from the sidewall 110' of the injector body 105'. This configuration makes it more difficult for an individual to grasp the plunger rod 130' to remove it from the injector body 105' utilizing a radial outward force.

Figure 26:
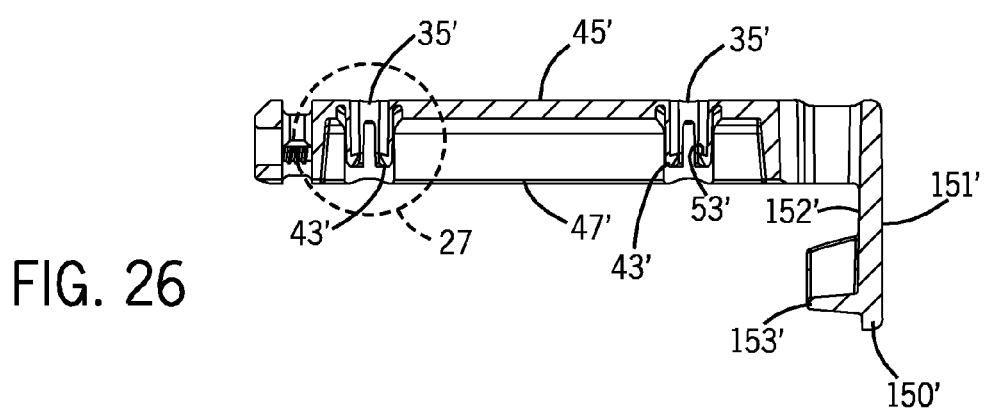
FIG. 26 is a cross-sectional elevation view about line 26-26 of FIG. 28.
Figure 27:
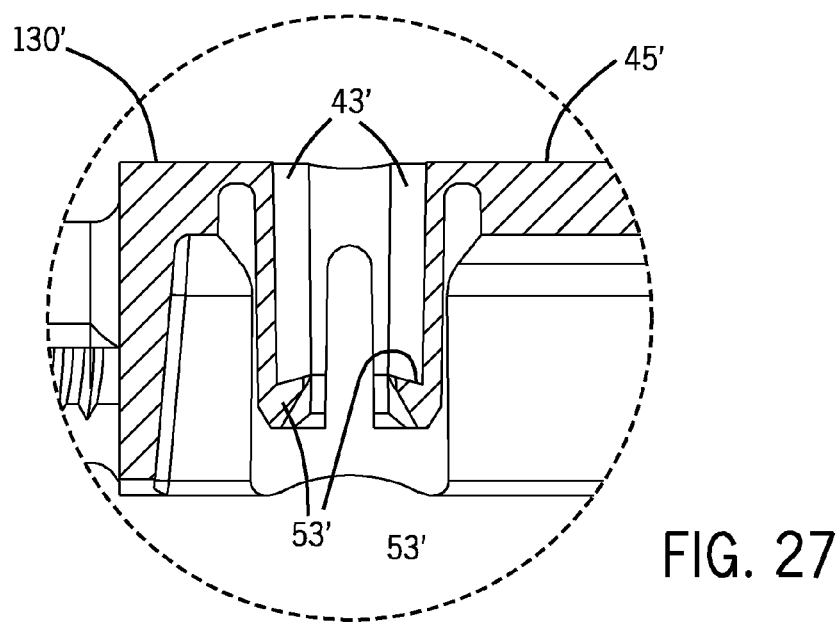
FIG. 27 is a partial enlarged view of one embodiment of a receiver aperture of the plunger rod of FIG. 25.
Figure 28:
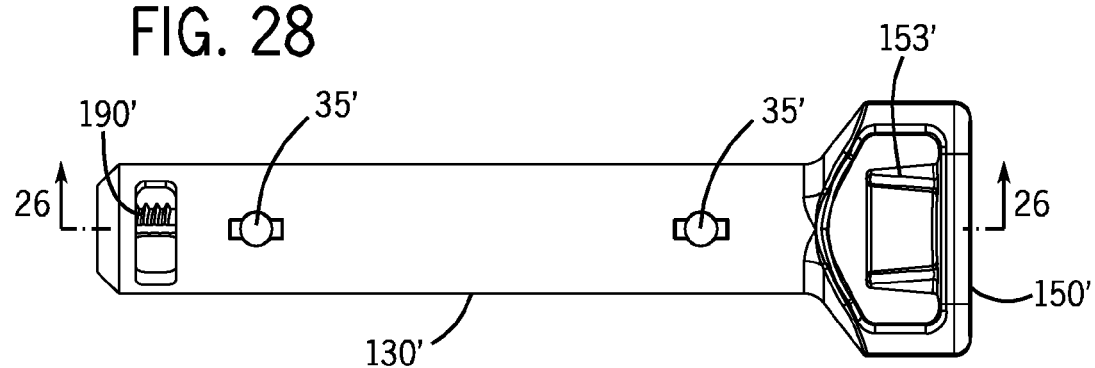
FIG. 28 is a top view of the plunger rod of FIG. 25.
Figure 29:
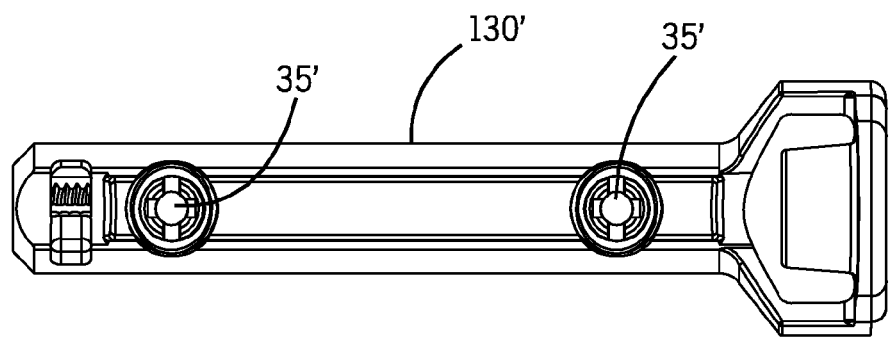
FIG. 29 is a bottom view of the plunger rod of FIG. 25.
Figure 30:
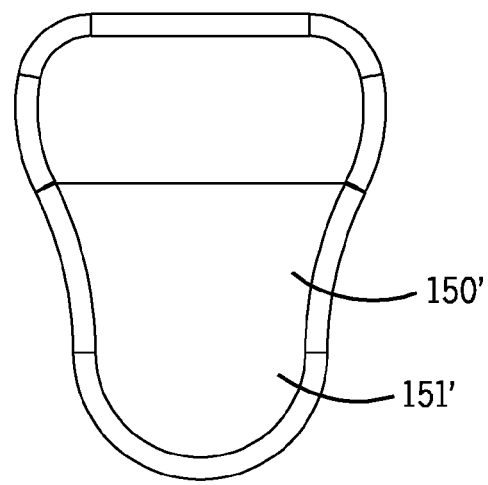
FIG. 30 is an end elevation view of the plunger rod of FIG. 25.

The retaining apertures 35' have a plurality resilient fingers 43' positioned therein. As shown in FIG. 29, in a preferred embodiment there are four resilient fingers 43' in each retaining aperture 35', however, it is readily understood by one of ordinary skill in the art that a fewer or greater number of resilient fingers 43' would suffice. Further, as shown in FIGS. 26 and 27, the resilient fingers 43' are connected to the body of the plunger rod 130' adjacent the top surface 45' of the plunger rod 130', and extend toward the lower surface 47' of the plunger rod 130'. It is understood that the lower surface 47' of the plunger rod 130' contacts or is adjacent the outer surface 115' of the injector body 105' when the plunger rod 130' is secured to the injector body 105'. The top surface 45' of the plunger rod 130', however, faces away from the injector body 105' when the plunger rod 130' is connected to the injector body 105' as shown in FIG. 13. Each of the resilient fingers 43' are hinged or cantilevered from their connection with the plunger rod 130' adjacent the top surface 45' of the plunger rod 130', and the distal end 49' of the resilient fingers 43' extend into a cavity of the injector rod 130' beneath the top surface 45' of the plunger rod 130'. The distal end 49' of each resilient finger 43' also has a flange 53' extending radially inwardly into the cavity of the retaining aperture 35'. The flanges 53' of each resilient finger 43' are utilized to engage the tabs 33' extending from the retention posts 136'.

To connect or attach the plunger rod 130' to the injector body 105', the lower surface 47' of the plunger rod 130' is positioned over the outer surface 115' of the injector body 105', with the retention posts 136' extending from the injector body 105' aligned with the retaining apertures 35'. The plunger rod 130' is then forced toward the injector body 105' such that the retention posts 136' engage the retaining apertures 35'. As the retention posts 136' are inserted into the retaining apertures 35' the retention posts 136' cause the distal end 49' portion of the resilient fingers 43' to flex radially outwardly. Additionally, as the retention posts 136' are inserted further into the retaining apertures 35', the transverse tabs 33' on the retention posts 136' extend past the flanges 53' on the resilient fingers 43' and are captured by the flanges 53'. Once the transverse tabs 33' on the retention posts 136' are captured by the flanges 53' the plunger rod 130' is locked in place on the injector body 105' and the plunger rod 130' cannot be removed from the injector body 105' without fracturing the retention posts 136'. Specifically, the tabs 33' prevent radial movement of the plunger rod 130' off the injector body 105', and the posts 136' prevent axial movement of the plunger rod 130' with respect to the injector body 105'. Accordingly, since the plunger rod 130' is fixedly retained to the injector body 105' by the cooperation between the retention members 135' and the receiving apertures 35', and since the posts 136' are broken from the exterior wall of the injector body 105' upon activation of the system 100', the plunger rod 130' cannot be re-attached to the injector body 105' after the posts 136' are broken, thereby providing a visual safety or tamper-evident indicator as described herein. Further, since the plunger rod 130' is fixedly attached to the injector body 105' prior to activation, the packaging necessary to maintain the system 100' together may be reduced. For example, instead of having to package or overwrap each injector body 105' and associated plunger rod 130' together with separate packaging, a plurality of injector systems 100' (with the associated plunger rod 130' fixedly attached to the injector body 105') may be mass grouped or packaged in larger quantities in a single container.

As shown in FIGS. 16, 18, 25 and 30, the proximal end portion 131' of the plunger rod 130' has a pushing member 150'. In one embodiment the pushing member 150' comprises a flange extending from the main body of the plunger rod 130'. The pushing member 150' includes a proximal surface 151' that is constructed for engagement with a medical professional's thumb. In use, a medical professional will grasp injector body 105' such that his/her index and middle fingers are in contact with a distal surface of finger grips 145' and such that his/her thumb is in contact with proximal surface 151' of pushing member 150'. The pushing member 150' is utilized to assist the user in both activating the pharmaceutical cartridge 155' as well as dispensing the contents of the pharmaceutical cartridge 155'.

Figure 15:
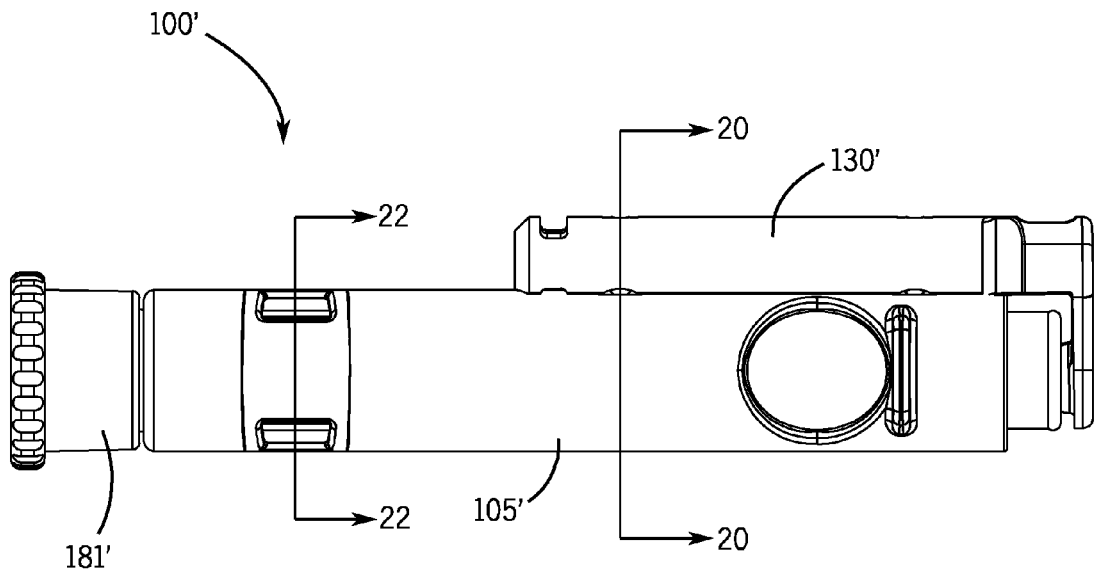
FIG. 15 is a side elevation view of the injector system of FIG. 13.
Figure 17:
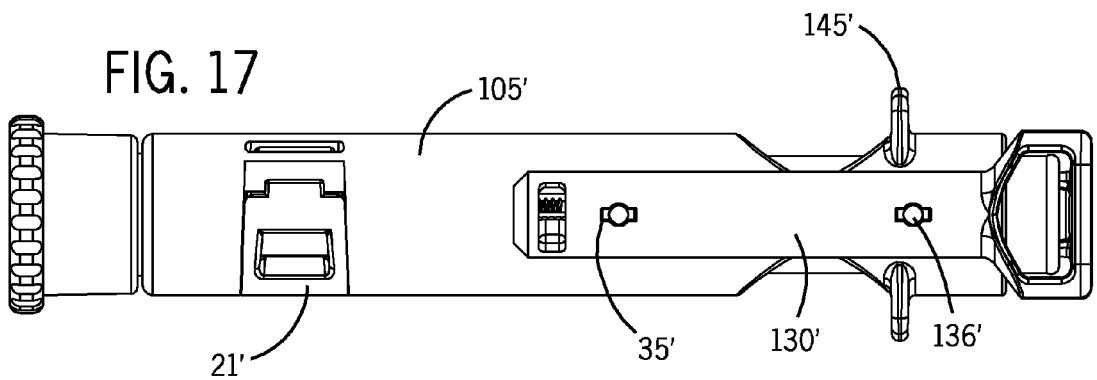
FIG. 17 is a top plan view of the injector system of FIG. 15.
Figure 18:
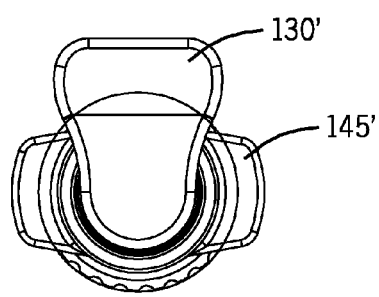
FIG. 18 is an end elevation view of the injector system of FIG. 15.
Figure 19:
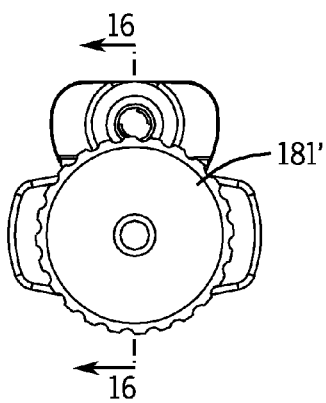
FIG. 19 is a front elevation view of the injector system of FIG. 15.

The pushing member 150' also includes a cartridge pushing surface 152'. The pushing surface 152' is utilized to transition the cartridge 155' from the inactivated position, as shown in FIGS. 15 and 16, to the activated position, as shown in FIG. 31. More specifically, the pushing surface 152' is constructed to engage the proximal end portion 156 of pharmaceutical cartridge 155' and to urge proximal end portion 156' of pharmaceutical cartridge 155' distally into the activated position as a medical professional squeezes his/her index and middle fingers towards his/her thumb. The importance of surface for pushing 152' will be described in greater detail later in this specification. In one embodiment the cartridge pushing surface 152' includes a nub 153' extending axially away from the pushing member 150'. In one embodiment, as best shown in FIG. 16, the nub 153' is configured to engage the pharmaceutical cartridge 155' for activating the pharmaceutical cartridge 155'. Further, in a preferred embodiment, the nub 153' is configured to be positioned partially within a cavity 154' at the proximal end portion 156' of the cartridge 155'. In this manner, the nub 153' operates to substantially block or preclude access to the contents of the pharmaceutical cartridge 155' through the proximal end portion 156', i.e., through the grommet of the pharmaceutical cartridge 155'. Accordingly, in such a preferred embodiment the nub 153' has a geometry that mates with the geometry of the cavity of the cartridge 155'. Since the plunger rod 130' is connected to the injector body 105', and thus the nub 153' is fixed in place in this position, the nub 153' will be positioned within the cavity 154' at the proximal end portion 156 of the cartridge 155' upon the cartridge 155' being inserted into the cavity 125' of the body 105' through the first opening 127' at the distal end 107' of the body 105' and pushed axially back toward the second opening 129'. In an alternative embodiment, nub 153' is substantially cylindrical or conical in shape and has a size that allows it to be positioned within, and to move within, the proximal end portion 156' of pharmaceutical cartridge 155'. In this alternative embodiment, nub 153' prevents access to the contents of the pharmaceutical cartridge 155' through the proximal end portion 156' thereof.

In one embodiment, as shown in FIGS. 25-29, the plunger rod 130' also has a connection member 190' at the distal end portion 132' of the plunger rod 130'. The connection member 190' is utilized to connect the plunger rod 130' to the piston/plunger 52' in the pharmaceutical cartridge 155'. In a preferred embodiment, the piston/plunger 52' in the pharmaceutical cartridge 155' has a connection member 160' extending out the proximal end portion 156' of the cartridge 155'. The connection member 190' of the injector rod 130' is adapted to connect to the connection member 160' of the pharmaceutical cartridge 155'. In a preferred embodiment, the connection member 160' of the pharmaceutical cartridge 155' is a threaded member. In such an embodiment where the connection member 160' is a threaded member, a complementary connection member 190' having complementary threads is provided on distal end portion 132' of plunger rod 130' such that plunger rod 130' can be threadably attached to connection member 160' on piston/plunger 52', thereby enabling a user to move piston/plunger 52' proximally and/or distally through the application of proximally and/or distally directed forces to plunger push surface 150' and/or to plunger rod 130'. As discussed herein, connection members 160' and 190' can have a variety of configurations so long as they provide the desired attachment of plunger rod 130' to piston/plunger 52'. For example, connection members 160' and 190' can be constructed to provide a pressure, friction or snap fit therebetween. Other configurations of connection members 160' and 190' will be readily appreciated by persons of ordinary skill in the art.

In the various embodiments illustrated herein, the injector body 105' and plunger rod 130' are depicted as separate pieces. These pieces can be injection molded or formed using a variety of other known tooling techniques. It will also be appreciated that injector body 105' and plunger rod 130' can be unitarily injection molded without departing from the intended spirit and scope of the present invention. Additionally, the injector body 105' and plunger rod 130' can be provided separately from the pharmaceutical cartridge 155' such that a medical professional, i.e., a pharmacist, inserts pharmaceutical cartridge 155' into the injector body 105' immediately prior to use. Alternatively, the injector body 105' and the pharmaceutical cartridge 155' can be pre-assembled by a manufacturer or assembler and supplied in combination to medical professionals. In a preferred embodiment, the pharmaceutical cartridge 155' is inserted into the injector body 105' and the injector system 100' is fully assembled prior to providing to the medical professional.

Injector body 105' and plunger rod 130' can be constructed from a variety of known materials, including metals, plastics, and various known composites. In order to minimize cost, plastic may be preferable. A variety of known plastic materials providing the requisite rigidity and other performance characteristics can be used in conjunction with the present invention.

The pharmaceutical cartridge 155' used in conjunction with the present invention can have a variety of configurations. Generally, the pharmaceutical cartridge 155' is a thin-walled tubular member constructed to retain a pharmaceutical product within an interior space or cavity 40' of the cartridge 155'. The pharmaceutical cartridge 155' has a cartridge body having a proximal end portion 156' and a distal end portion 157'. The pharmaceutical cartridge 155' also has an interior space or cavity 40' wherein the medicament is housed. As shown in FIG. 16, a piston/plunger 52' is slidably positioned within the interior space 40' at the proximal end portion 156' of pharmaceutical cartridge 155', and fluidly seals the proximal end portion 156' of pharmaceutical cartridge 155', and a pierceable diaphragm 50' fluidly seals the distal end portion 157' of the cavity 40' of the cartridge 155'. In a preferred embodiment a connection member 160', e.g., threaded rod, is attached to piston/plunger 52' such that the connection member 160' is accessible from the exterior of cartridge 155'.

In most cases it will be preferable to construct pharmaceutical cartridge 155' from known glass materials due to the relative inactivity between glass and most pharmaceutical products. However, it will be appreciated that in certain cases it may be appropriate or necessary to use non-glass materials due to the possible interaction between the pharmaceutical product to be contained in pharmaceutical cartridge 155' and the material from which pharmaceutical cartridge 155' is constructed.

Figure 14:
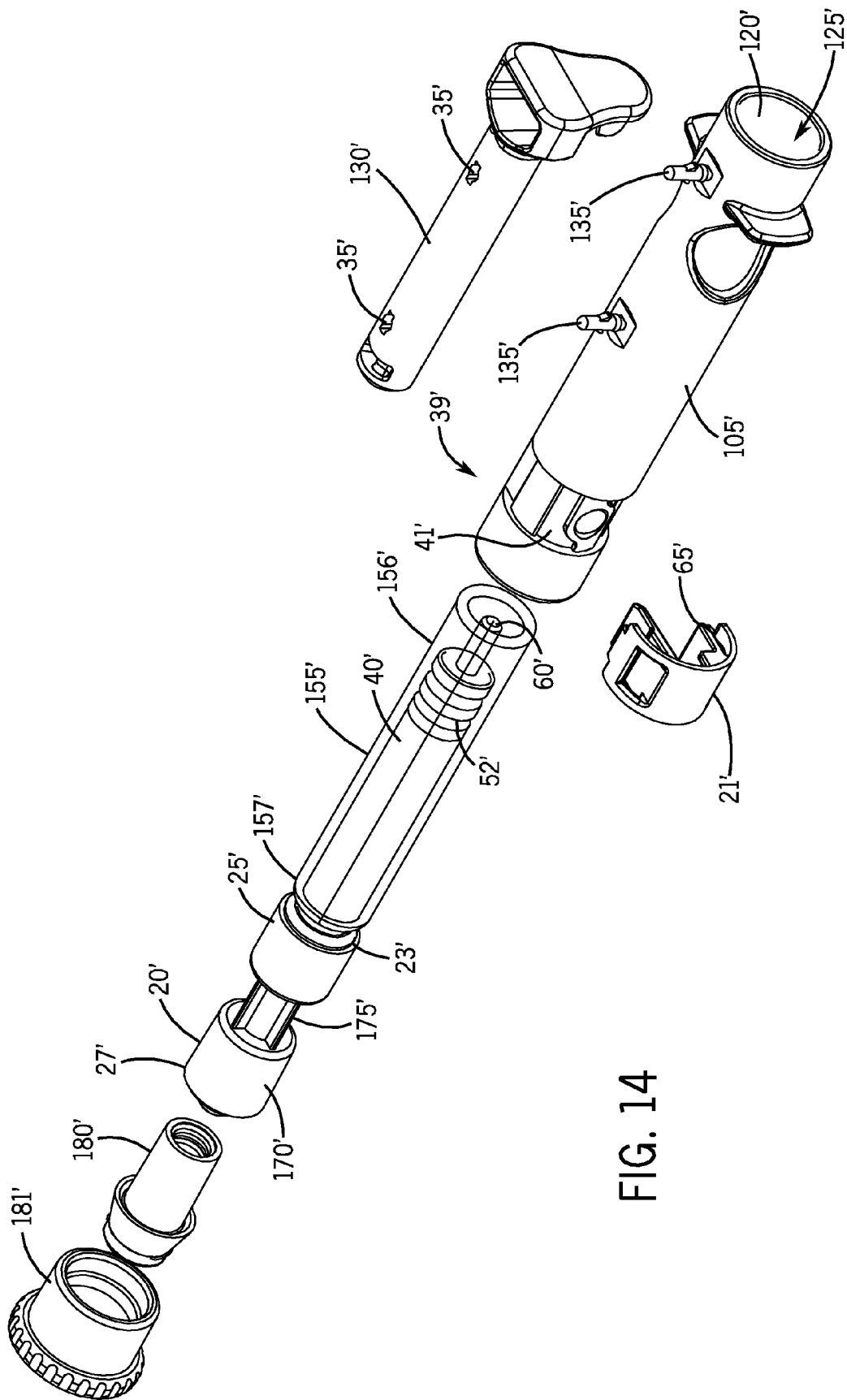
FIG. 14 is an exploded perspective view of the injector system of FIG. 13.

As shown in FIGS. 14, 16 and 22, a hub 20' is slidably mounted on the distal end portion 157' of the pharmaceutical cartridge 155'. In one embodiment the hub 20' comprises a mounting portion 23' at a proximal end 25', a connecting portion 170' at a distal end 27', and a necked down portion 175' between the mounting portion 23' and the connecting portion 170'. Further, the hub 20' has a bore 29' extending from the distal end 27' to the proximal end 25' thereof. A piercing member (or needle cannula) 18' is fixed in place in the bore 29' of the hub 20'. The piercing member 18' is constructed to pierce the pierceable diaphragm 50'. The mounting portion 23' of the hub 20' has a sidewall 61' and a bottom wall 63'. The sidewall 61' of the hub 20' is slidingly secured to the sidewall of the cartridge 155' at the distal end portion 157' of the cartridge 155' in the inactivated position as shown in FIG. 16. In that inactivated position, a gap 64' is provided between the distal end 157' of the cartridge 155' and the bottom wall 63' of the mounting portion 23' of the hub 20'.

As explained herein, the hub 20' is fixed in place (longitudinally and rotationally) in the injector body 105' via the hub clip 21', however, the pharmaceutical cartridge 155' is slidable with respect to the hub 20' between a first, inactivated position in which piercing member 18' is positioned outside of cartridge 155' and distally of pierceable diaphragm 50' (as shown in FIG. 16), and a second, activated position in which piercing member 18' is disposed through pierceable diaphragm 50' and in which interior lumen 165' defined by piercing member 18' is in fluid communication with the contents in the cavity 40' of cartridge 155', thereby providing a pathway for the egress of fluids from cartridge 155' through piercing member 18' in response to pressure applied when piston/plunger 52' is moved distally by the plunger rod 130'. In the inactivated position the gap 64' is provided between the distal end 157' of the cartridge 155' and the bottom wall 63' of the mounting portion 23' of the hub 20'. During activation, however, the hub 20' remains fixed in place and the cartridge 155' is moved axially distally toward the bottom wall 63' of the mounting portion 23' of the hub 20'. In one embodiment, the bottom wall 63' of the mounting portion 23' of the hub 20' operates as a stop for the cartridge 155'.

Referring to FIGS. 14, 16 and 22, the hub clip 21' is used to fix the hub 20' in place in the injector body 105'. As explained above, the injector body 105' has a receiver 39' for receiving the hub clip 21'. In this embodiment the receiver 39' comprises a plurality of openings 41' through the sidewall 110' of the injector body 105'. The receiver 39' is shown in FIGS. 23a and 24. When the pharmaceutical cartridge 155' and hub 20' are inserted into the cavity 125' of the injector body 105' through the first opening 127' at the distal end 107' of the injector body 105', the cartridge 155' is pushed axially back toward the second opening 129' until the proximal end portion 156' of the cartridge 155' contacts the pushing surface 152' of the pusher member 150' of the plunger rod 130'. In this position the necked down portion 175' of the hub 20' will be aligned with the openings 41' in the sidewall 110' of the injector body 105'.

In one embodiment the hub clip 21' has a plurality of projections 65' that extend through the openings 41' in the sidewall 110' of the injector body 105'. The hub clip 21' also has an outer geometric shape similar to the shape of the exterior surface of the sidewall 110' of the injector body 105'. In a preferred embodiment the width of the projections 65' are generally similar to the width of the necked-down portion 175' of the hub 20'. Thus, when the hub 20' is positioned in the injector body 105', and after the clip 21' is inserted through the openings 41' in the sidewall 110 of the injector body 105', the projections 65' preclude any axial movement of the hub 20'. Additionally, the shape of the projections 65' engages fins extending from the body of the hub 20' in the necked-down region 175' such that the hub 20' is also precluded from rotating in the injector body 105'. Finally, the hub clip 21' has resilient tabs 67' that snap into place at various openings 41' in the injector body 105' sidewall 110' to keep the clip 21' fixed in place on the injector body 105'. Further, in order to prevent the clip 21' from being removed from the injector body 105', a label is typically placed around the body 105' and the clip 21'. The label (not shown) may also secure the cap 181' to the injector body 105'. To remove the cap 181' from the body 105', it will be necessary to tear the label, thereby providing visual evidence (i.e., tamper evidence) of such occurrence.

Similar to connecting portion 170' described in the prior embodiment, the connection portion 170' of the hub 20' in this embodiment is configured to deliver the pharmaceutical product contained in pharmaceutical cartridge 155' to a patient or to another medical apparatus, e.g., a tube set configured to deliver pharmaceutical products to a patient. The connection portion 170' may be a threaded luer member constructed to connect with a complementary luer member. It will be appreciated that connection portion can have a variety of configurations, including: (i) a hypodermic needle for delivery of pharmaceutical products directly to a patient or for delivery through a pierceable septum, e.g., a pierceable septum associated with an add port of a tube set or an add port of a flexible pharmaceutical container; (ii) a blunt needle for delivery of pharmaceutical products from pharmaceutical cartridge to a medical device having the capability of receiving a pharmaceutical product from a blunt needle, e.g., a pre-slit elastomeric seal on a tube set or a flexible pharmaceutical container; (iii) threaded luer; and/or (iv) an unthreaded luer.

A first hub cap 180' is provided to mate with the connection portion 170' and cover the exposed end of the needle cannula 18'. A short second hub cap 181' is joined to the first hub cap 180', generally via a press fit, and provides a member for the medical professional to grasp for removing the first and second hub caps 180', 181' from the hub 20' to expose the needle cannula 18'. Cap members 180' and 181' can be provided in order to cover the connector 170' and cannula 18' when the injector device 100' of the present invention is not in use. The cap members 180' and 181' are preferably constructed of a material that will preclude access to the contents of the cartridge 155' through the cap 181'. The end of the cap 181' is flat, thereby reducing the overall length of the system 100'.

The cartridge 155' may be loaded into the cavity of the injector body 105' from either the proximal end 106' or the distal end 107' of the body 105', as long as the plunger rod 130' is not connected to the body 105' first. If the plunger rod 130' is connected to the body 105', then the pushing member precludes access of the cartridge 155' through the second opening 129' at the proximal end 106', and the cartridge 155' must be inserted through the first opening 127' at the distal end 107' of the body 105'.

In order to use injector device 100', a medical professional will engage finger grips 145' with his/her index and middle fingers and will engage proximal surface 151' of plunger push surface 150' with his/her thumb. By squeezing his/her thumb and fingers together, plunger push surface 150' and finger grips 145' are moved closer to one another. Also by squeezing his/her thumb and fingers together, the pushing surface 152' and associated nub 153' apply an axial distal force on proximal end portion 156' of pharmaceutical cartridge 155'. However, because the hub clip 21' precludes axial distal movement of the hub 20', the application of a distally directed axial force on proximal end portion 156' of pharmaceutical cartridge 155' causes pharmaceutical cartridge 155' to move from its first, inactivated position (see FIG. 16) toward its second, activated position (see FIG. 31). The squeezing force also causes plunger rod 130' to move axially distally relative to injector body 105' from its first, engaged position (shown in FIG. 16) in which the retention members 135' are connected to the injector body 105' and retained in the receiving or retaining apertures 35', to its second, released position in which the retention posts 136' are sheared from the injector body 105' at the necked down portion 37' of the posts 136'. The posts 136' are retained in the receiving apertures 35'. After the posts are sheared from the injector body 105', the resilient fingers 43' retain the posts 136' in the receiving apertures 35'. In operation, pharmaceutical cartridge 155' is in its second, activated position when plunger rod 130' is in its second, released position. In the second released position the plunger rod 130' is free from the injector body 105' and can be removed therefrom.

After the posts are sheared from the injector body 105', the plunger rod 130' can be removed from the injector body 105' and positioned such that the distal end portion 132' of the plunger rod 130' is adjacent to connection member 160' on piston/plunger 52'. Where connection member 160' is a threaded member, a complementary connection member 190' having complementary threads is provided on the distal end portion 132' of plunger rod 130' such that plunger rod 130' can be threadably attached to connection member 160' on piston/plunger 52' as shown in FIG. 32, thereby enabling a user to move piston/plunger 52' proximally and/or distally through the application of proximally and/or distally directed forces to plunger push surface 150' and/or to plunger rod 130'. As discussed above, connection members 160' and 190' can have a variety of configurations so long as they provide the desired attachment of plunger rod 130' to piston/plunger 52'. For example, connection members 160' and 190' can be constructed to provide a friction or snap fit therebetween. Other configurations of connection members 160' and 190' will be readily appreciated by persons of ordinary skill in the art of the present invention.

After plunger rod 130' has been connected to piston/plunger 52' using complementary connection members 160', 190', a pharmaceutical product contained in pharmaceutical cartridge 155' can be delivered to a patient or transferred to another medical device by the application of an axial distally-directed force to plunger rod 130', e.g., through the application of a distally directed force to proximal surface 151' of plunger push surface 150'. If desired, fluids can be aspirated into pharmaceutical cartridge at any time through the application of a proximally directed force to plunger push surface 150'.

Another embodiment of the injector device 100" is shown in FIGS. 33-58. This embodiment of the injector device 100" is also adapted to receive and hold a pharmaceutical cartridge or ampule 155" containing a pharmaceutical product, and for dispensing a drug therefrom. This embodiment of the injector device 100" generally comprises a syringe housing or injector body 105", a plunger rod 130", a hub clip 21", and a tamper-evident band 194". In one embodiment the cartridge system generally comprises a cartridge 155", a hub 20", a first or inner hub cap 180" and a second or outer cap 181", however, it is understood that alternate cartridge systems may be utilized with the injector device 100" without departing from the scope of the present invention.

In a preferred embodiment of this injector device 100", the injector body 105", plunger rod 130", hub clip 21" and tamper-evident band 194" are all manufactured in a multi-step, multi-shot molding process, such that assembly of the individual components to create the injector device 100" is not required. It is understood, however, that several features of this embodiment of the injector device 100" retain aspects of components of the prior embodiment injector devices 100 and 100', and thus like numbers are utilized herein. Additionally, since certain features of this embodiment are similar to the prior-described embodiments, those features may not be explained in further detail herein.

Figure 33:
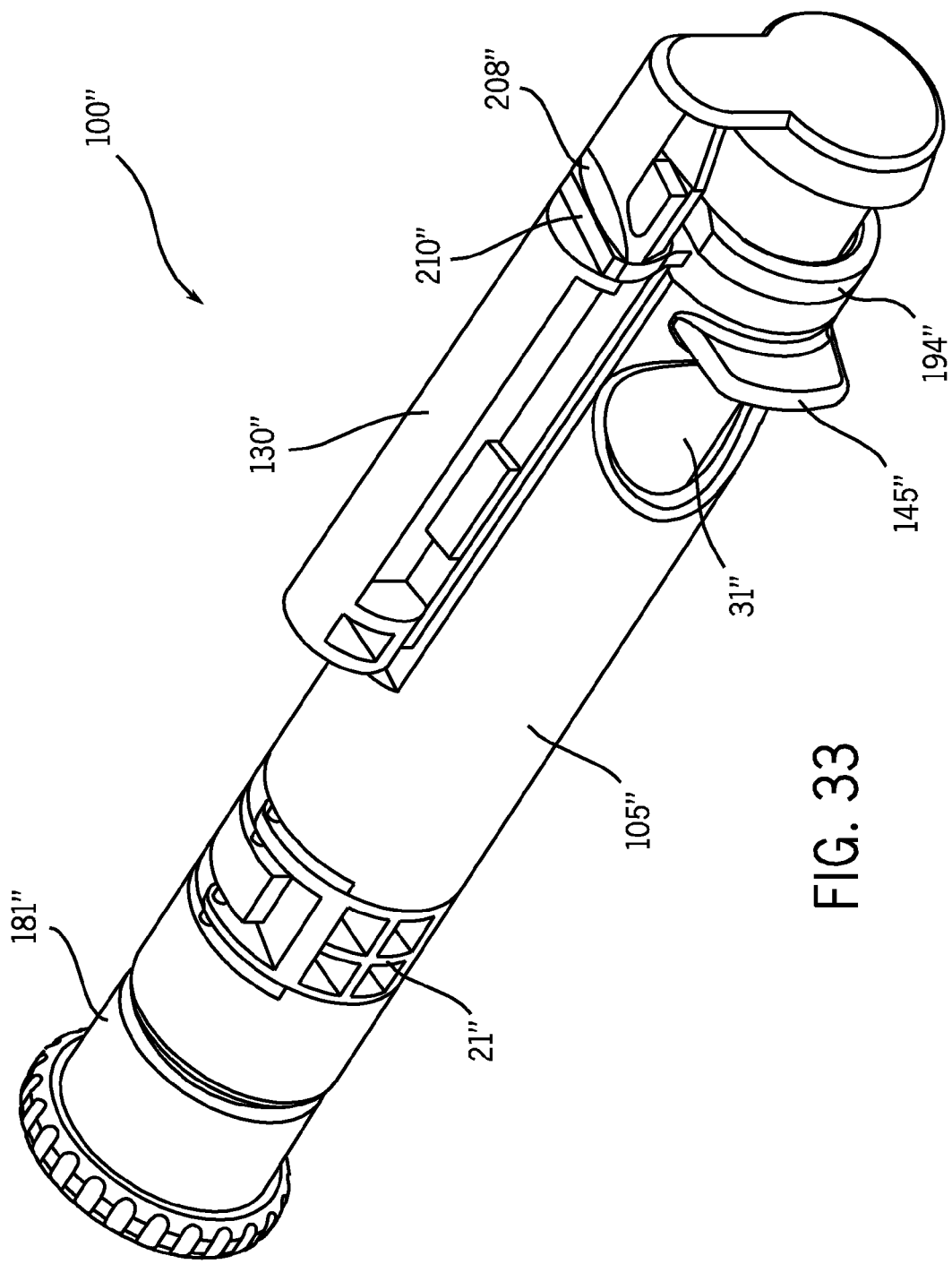
FIG. 33 is a perspective view of another embodiment of the injector system.

As shown in FIG. 33 of this embodiment, the plunger rod 130" is manufactured and mounted on the injector body 105" in a first position. In this embodiment the injector body 105" has a sidewall 110" with an outer surface 115" and an inner surface 120". In a preferred embodiment, the injector body 105" is preferably tubular in geometry. While the sidewall 110' is illustrated in the accompanying figures as being tubular or cylindrical in shape, it will be appreciated that the shape of side wall 110" can be varied for different purposes and to accept various shaped cartridges 155". The inner surface 120" of side wall 110" defines a cavity or region 125" for receiving at least a portion of cartridge 155" therein.

The injector body 105" has a proximal end portion 106" and a distal end portion 107". The injector body 105" further has a first opening 127" to the cavity 125" at the distal end portion 107" of the body 105", and a second opening 129" to the cavity 125" at the proximal end portion 106" thereof. As is shown in FIGS. 38 and 41-43, the injector body 105" also has a pair of grip openings 31" extending through the sidewall 110" and into the cavity 125". As is explained in detail herein in prior embodiments, the grip openings 31" assist the user in activating the cartridge 155" and dispensing the pharmaceutical product from the cartridge 155". The grip openings 31" also allow the finger grips 145" to have a decreased size.

Since a preferred variation of the embodiment of this injector device 100" is manufactured together in a multi-step multiple-shot molding process, the injector body 105", plunger rod 130", hub clip 21" and tamper-evident band 194" come pre-assembled. Thus, the pharmaceutical cartridge 155" is typically inserted into the cavity 125" of the body 105" through the first opening 127" at the distal end 107" of the body 105". In the inactivated position, as shown in FIG. 37, the cartridge 155" is fitted into the cavity 125" through the first opening 127", and pushed axially back toward the second opening 129". As explained herein, the proximal end portion 156" of the cartridge 155" is generally positioned adjacent the pushing surface 152" of the plunger rod 130" in the inactivated position.

In a preferred embodiment the injector body 105" is preferably made of a plastic material, and preferably a generally rigid plastic material, such as polycarbonate. Additionally, the injector body 105" is preferably clear or transparent, allowing the cartridge 155" inserted into the cavity 125" of the injector body 105" to be visible through the sidewall 110" of the injector body 105". As explained herein, in this manner a bar code (not shown) on the outer wall of the cartridge 155" can be visible through the sidewall 110" of the injector body 105" and can be scanned through the sidewall 110" when the pharmaceutical cartridge 155" is seated in the cavity 125" of the injector body 105".

As shown in FIGS. 34 and 47-50, the injector body 105" has one or more retention members 135" positioned on the outer surface 115" of the injector body 105". In this embodiment the retention members 135" are utilized to preclude axial and rotational movement of the plunger rod 130" with respect to the injector body 105" until activation of the injector device 100" is desired.

Figure 50:
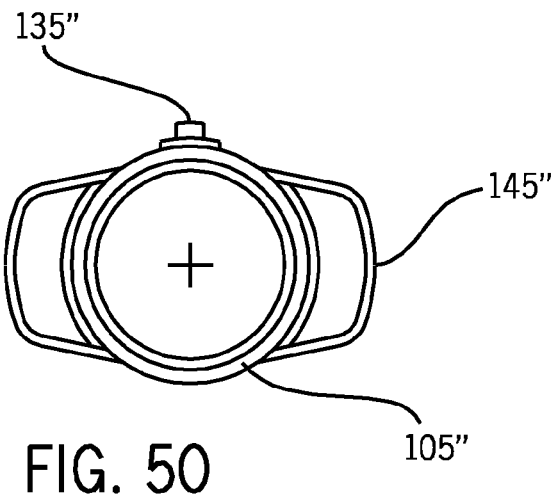
FIG. 50 is an end elevation view of the injector body of FIG. 47.

In a preferred embodiment, the retention members 135" comprise a protrusion 196", such as a tenon 196", projecting radially outwardly from the outer surface 115" of the injector body 105". In the embodiment shown, a single retention member 135" is utilized, however, it is understood that two or more retention members 135" may be utilized to fixedly retain the plunger rod 130" in position until activation. In a preferred embodiment, the retention members 135" have a dovetail-type configuration. Accordingly, as shown in FIGS. 46 and 50, the portion of the retention member 135" proximal the outer surface 115" of the injector body 105" has a narrower cross-sectional width, shown as being perpendicular to the longitudinal axis of the injector body 105", than the cross-sectional width of the portion of the retention member 135," distal the outer surface 115," of the injector body 105". This structural configuration provides the retention members 135" of this embodiment with the identified dovetail-type configuration. Such a geometry, when used in conjunction with a mating configuration on the plunger rod 130", positively precludes axial or upward (i.e., radially outward) movement of the plunger rod 130" off of the injector body 105". From the top view, as shown in FIG. 48, in one embodiment the retention member 135" has a figure eight-type shape. This assists in maintaining appropriate tolerances in retention member 135" during the manufacturing of the retention member 135", as well as assisting to maintain the appropriate removal forces for the plunger rod 130". For manufacturing purposes, a recess 198" is provided in the top surface of the injector body 105" adjacent the remember 135" to allow for the insertion of mold components in the manufacturing process.

Although this embodiment of the injector system 100" is depicted in the accompanying figures as including a single retention member 135", it will be appreciated that a greater number of retention members 135" can be used to secure the plunger rod 130" to outer surface 115" of side wall 110" of injector body 105". Similarly, the details of the construction of retention members 135" and receiving or retaining members 35" set forth herein are not intended to be limited to the identified configurations depicted in the accompanying drawings of the injector system. For example, the retention member 135" may extend a greater distance about the length of the joining surface of the plunger rod 130" and the injector body 105". One of ordinary skill in the art will recognize that various modifications can be made to the number and configuration of retention members 135" and receiving or retaining members 35" (described in detail later herein) without departing from the spirit and scope of the present invention. In short, the accompanying figures are intended to be illustrative, not limiting, with respect to the configuration and number of retention members 135" and receiving or retaining members 35".

The injector body 105" also preferably includes finger grips 145" which are similar to the finger grips 145' described in the preceding embodiment. Accordingly, the disclosure of such finger grips 145" is discussed above.

In a preferred embodiment of this injector system 100", the injector body 105" has a receiver 39" for receiving the hub clip 21". In this embodiment, however, rather than being a detached component that engages the receiver 399", the hub clip 21" is rotatedly connected or hinged (e.g., through a living hinge) directly to the injector body 105", and can rotate from a first position wherein the hub clip 21" is not within the receiver opening 39", thereby allowing the pharmaceutical cartridge 155" to be moveable longitudinally and rotationally in the cavity 125" of the injector body 105", to a second position wherein the hub clip 21" retains the hub 20" of the pharmaceutical cartridge 155" in a fixed position relative to the injector body 105". The receiver 39" preferably comprises one or more openings 41" through the sidewall 110" of the injector body 105". In a preferred embodiment the receiver 39" is located toward the distal end portion 107" of the injector body 105". The hub clip 21" and its rotational connection to the injector body 105" is described in greater detail herein.

As shown in FIGS. 45 and 47-49, to rotatedly or hingedly attach the hub clip 21" to the injector body 105", a pair of rods or hinge members 200" are provided as part of the injector body 105". The rods 200" extend longitudinally within an arcuate plane of the sidewall 110", such that the pivot point of the hub clip 21" is within the thickness of the sidewall 110" of the injector body 105". In a preferred embodiment, the rods 200" are manufactured in connection with the manufacture of the injector body 105". Further, in a preferred embodiment there are two rods 200", with a finger portion 202" of the sidewall 110" extending therebetween to reduce flexing such as if a single extended shaft was used.

Referring to FIGS. 35, 37, 38, 43 and 45, the hub clip 21" is used to fix the hub 20" associated with the pharmaceutical cartridge 155' in place in the injector body 105". As explained herein with respect to prior embodiments, the hub 20" associated with the pharmaceutical cartridge 155" is fixed in place in the injector body 105" via the hub clip 21", however, the pharmaceutical cartridge 155" is slidable with respect to the hub 20" between a first, inactivated position in which piercing member 18" is positioned outside of cartridge 155" and distally of pierceable diaphragm 50" (as shown in FIG. 37), and a second, activated position in which piercing member 18" is disposed through pierceable diaphragm 50" and in which interior lumen 165" defined by piercing member 18" is in fluid communication with the contents in the cavity 40" of cartridge 155", thereby providing a pathway for the egress of fluids from cartridge 155" through piercing member 18" in response to pressure applied when piston/plunger 52" is moved distally by the plunger rod 130". During activation the hub 20" remains fixed in place by the hub clip 21", and the cartridge 155" is moved axially distally toward the bottom wall 63" of the mounting portion 23" of the hub 20". In a preferred embodiment the hub clip 21" is preferably made of a plastic material, and preferably a generally rigid plastic material, such as High impact polystyrene.

As explained above, the injector body 105" has a receiver 39" for receiving the hub clip 21" to secure the hub clip 21" in place. In this embodiment the receiver 39" comprises an opening 41" through the sidewall 110" of the injector body 105". The receiver 39" is shown in FIGS. 47-49. When the pharmaceutical cartridge 155" and hub 20" are inserted into the cavity 125" of the injector body 105" through the first opening 127" at the distal end 107" of the injector body 105", the cartridge 155" is pushed axially back toward the second opening 129" until the proximal end portion 156" of the cartridge 155" contacts the pushing surface 152" of the pusher member 150" of the plunger rod 130". In this position the necked down portion 175" of the hub 20" will be aligned with the opening 41" in the sidewall 110" of the injector body 105".

As best shown in FIG. 45, the hub clip 21" is rotatedly or hingedly connected to the injector body 105" at the hinge members 200" thereof. In one embodiment the hub clip 21" has a projections 65" that extend through the openings 41" in the sidewall 110" of the injector body 105" to engage the hub 20". The projections 65" extend from adjacent an end of the hub clip 21" opposite the end connected to the hinge members 200". The outer surface of the hub clip 21" has a geometry similar to the shape of the exterior surface of the sidewall 110" of the injector body 105". In a preferred embodiment the width of the projection 65" is generally similar to the width of the necked-down portion 175" of the hub 20". Thus, when the clip 21" is rotated to its second or connected position shown in FIGS. 33 and 35, from its first or unconnected position shown in FIG. 45, the projections 65" preclude any axial movement of the hub 20". The hub clip 21" has a resilient tab 67" that snaps into place in one of the openings 41" in the sidewall 110" of the injector body 105" to keep the clip 21" fixed in place on the injector body 105". Resilient tab 67" and openings 41" preferably are constructed such that it is relatively difficult to move clip 21" back to its first or unconnected position after it has been moved to its second or connected position, thereby minimizing the possibility of tampering with the contents of pharmaceutical cartridge 155". Further, in order to prevent the clip 21" from being removed from the injector body 105", a label may be placed around the body 105" and the clip 21". The label (not shown) may also secure the cap 181" to the injector body 105". In such an embodiment, to remove the cap 181" from the body 105" it will be necessary to tear the label, thereby providing visual evidence of such occurrence.

As described in the embodiment above, a connection portion 170" of the hub 20" is configured to deliver the pharmaceutical product contained in pharmaceutical cartridge 155" to a patient or to another medical apparatus, e.g., a tube set configured to deliver pharmaceutical products to a patient. The connection portion 170" is described in detail above.

Also as described in the embodiment above, a first hub cap 180" is provided to mate with the connection portion 170" and cover the exposed end of the needle cannula 18". And, a short second hub cap 181" is joined to the first hub cap 180", generally via a press fit, and provides a member for the medical professional to grasp for removing the first and second hub caps 180", 181" from the hub 20" to expose the needle cannula 18". Cap members 180" and 181" can be provided in order to cover the connector 170" and cannula 18" when the injector device 100" of the present invention is not in use.

Referring now to FIGS. 51-56, one embodiment of the plunger rod 130" is shown. The plunger rod 130" has a body portion 51" with a proximal end portion 131" and a distal end portion 132". The plunger rod 130" also has one or more retaining or receiving members 35". In one embodiment, the retaining members 35" comprise a receiving cavity 35" for matingly receiving the retention members 135" extending from the injector body 105". The retaining members 35" are constructed to cooperate with retention members 135" to retain the plunger rod 130" on the injector body 105" until activation of the pharmaceutical cartridge 155". Thus, in this preferred embodiment, the retaining members 35" comprise a mating cavity or dovetail-style mortise 35" to mate with the dovetail-style configured tenons 135" extending from the injector body 105". Accordingly, the cavity 35" of the retaining members 35" has a reverse geometry to that described for the retention members 135" of this embodiment. Specifically, in one embodiment the portion of the cavity 35" proximal the entrance to the cavity 35" has a narrower cross-sectional width, shown as being perpendicular to the longitudinal axis of the plunger rod 130", than the cross-sectional width of the portion of the cavity 35" distal the entrance to the cavity 35". In this mating configuration, radial and rotational movement of the plunger rod 130" is precluded by the dovetail-style connection. Only axial or lateral movement of the plunger rod 130" can occur without fracturing the retention members 135". As is explained in detail herein, if lateral movement of the plunger rod 130" occurs, or if sufficient radial outward or rotational force is applied to the plunger rod 130" to fracture the retention member 135", the tamper-evidence band 194" will provide visual evidence of such occurrence.

For manufacturing purposes, a recess 204" is provided in the bottom surface of the plunger rod 130" adjacent the retaining cavity 35" to allow for the insertion and removal of mold components in the manufacturing process. Additionally, in a preferred embodiment the plunger rod 130" is preferably made of a plastic material, and preferably a generally rigid plastic material, such as high impact polystyrene.

In a preferred embodiment the main body portion 51" of the plunger rod 130" has a generally C-shaped cross-section, with the outer convex surface of the body 51" facing radially outward from the sidewall 110" of the injector body 105". This configuration makes it more difficult for an individual to grasp the plunger rod 130" to attempt to remove the plunger rod 130" from the injector body 105" utilizing a radial outward force.

Once the retention members 135" are captured in the retaining cavities 35" the plunger rod 130" is locked in place on the injector body 105" and the plunger rod 130" cannot be removed from the injector body 105" without fracturing the tamper-evident band 194" (as well as possible fracturing the retention members 135"). As is explained in detail herein, since the plunger rod 130" is retained to the injector body 105" by the cooperation between the retention members 135" and the receiving cavities 35", and since the tamper evident bands 194" are broken upon activation of the system 100" or upon removal of the plunger rod 130" from the injector body 105", a visual safety or tamper-evident indicator is provided to any subsequent user that the system 100' is compromised. Further, since the plunger rod 130" is fixedly attached to the injector body 105" during manufacturing, the packaging necessary to maintain the system 100" as a unit may be reduced. For example, instead of having to package or overwrap each injector body 105" and associated plunger rod 130" together with separate packaging, a plurality of injector systems 100" (with the associated plunger rod 130" fixedly attached to the injector body 105") may be mass grouped or packaged in larger quantities in a single container.

As shown in FIGS. 35 and 51-56, the proximal end portion 131" of the plunger rod 130" has a pushing member 150". In one embodiment the pushing member 150" comprises a flange extending from the main body of the plunger rod 130". The pushing member 150" includes a proximal surface 151" that is constructed for engagement with a medical professional's thumb. In use, a medical professional will grasp injector body 105" such that his/her index and middle fingers are in contact with a distal surface of finger grips 145" and such that his/her thumb is in contact with proximal surface 151" of pushing member 150". The pushing member 150" is utilized to assist the user in both activating the pharmaceutical cartridge 155" as well as dispensing the contents of the pharmaceutical cartridge 155".

The pushing member 150" also includes a cartridge pushing surface 152", which is generally opposite the proximal surface 151". The pushing surface 152" is utilized to contact the cartridge 155" to transition the cartridge 155" from the inactivated position, as shown in FIGS. 35 and 37, to the activated position (similar to that shown for the prior embodiment in FIG. 31). More specifically, the pushing surface 152" is constructed to engage the proximal end portion 156" of pharmaceutical cartridge 155" and to urge proximal end portion 156" of pharmaceutical cartridge 155" distally into the activated position as a medical professional squeezes his/her index and middle fingers towards his/her thumb.

Figure 51:
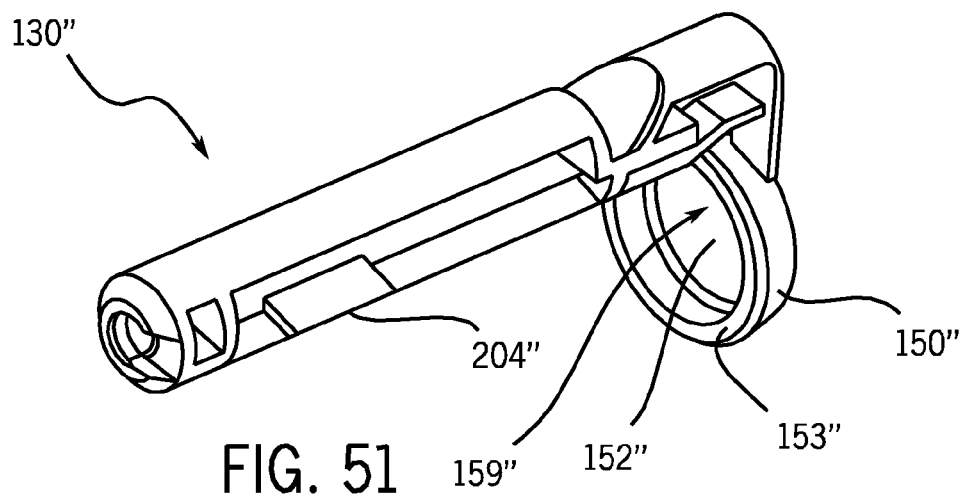
FIG. 51 is a perspective view of another embodiment of the plunger rod for use with the system of FIG. 38.
Figure 52:
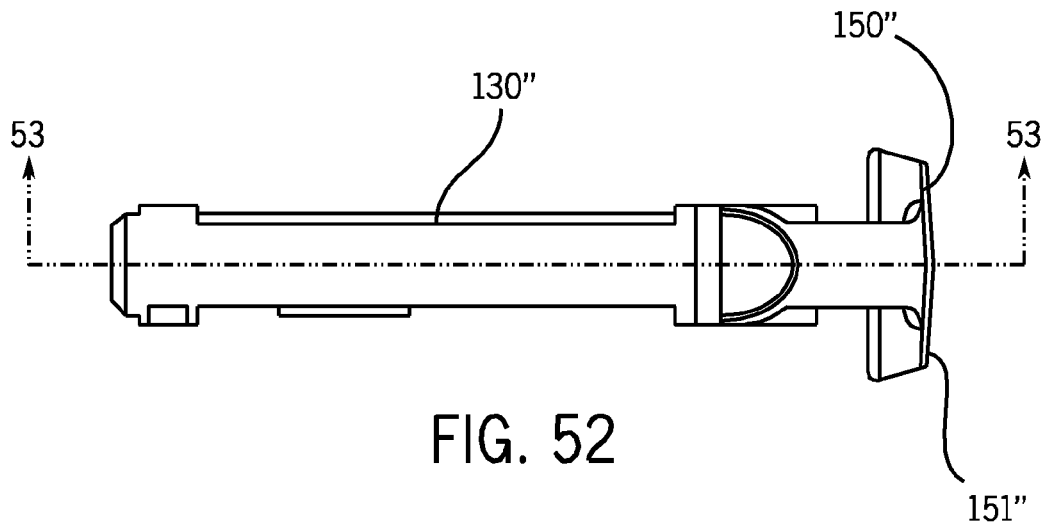
FIG. 52 is a top view of the plunger rod of FIG. 51.

In one embodiment the cartridge pushing surface 152" has a flange 153" extending axially away from the perimeter of the pushing member 150" to create a cavity 159", as shown in FIG. 51. Referring to FIG. 37, in this embodiment the pusher surface 152" and flange 153" of the plunger rod 130" are configured as a female receiver to allow the proximal end portion 156" of the cartridge 155" to be positioned within the cavity 159" of the pushing member 150" in the inactivated or standard position. The end portion 156" of the cartridge 155" thus operates as the male member and is positioned within the female cavity 159" of the pushing member 150". Since the end portion 156" of the cartridge 155" is positioned within the cavity 159", the system 100" precludes access to the contents of the pharmaceutical cartridge 155" through the proximal end portion 156", i.e., through the grommet of the pharmaceutical cartridge 155',' as a safety feature.

In one embodiment, as shown in FIGS. 51-56, the plunger rod 130" also has a connection member 190" at the distal end portion 132" of the plunger rod 130". The connection member 190" is utilized to connect the plunger rod 130" to the piston/plunger 52" in the pharmaceutical cartridge 155" as described in the preceding embodiments.

Similarly, the pharmaceutical cartridge 155" used in conjunction with the present invention can have a variety of configurations, which are described herein with respect to other embodiments. Likewise, the hub 20", which is slidably mounted on the distal end portion 157" of the pharmaceutical cartridge 155", is also described herein in prior embodiments.

Figure 34:
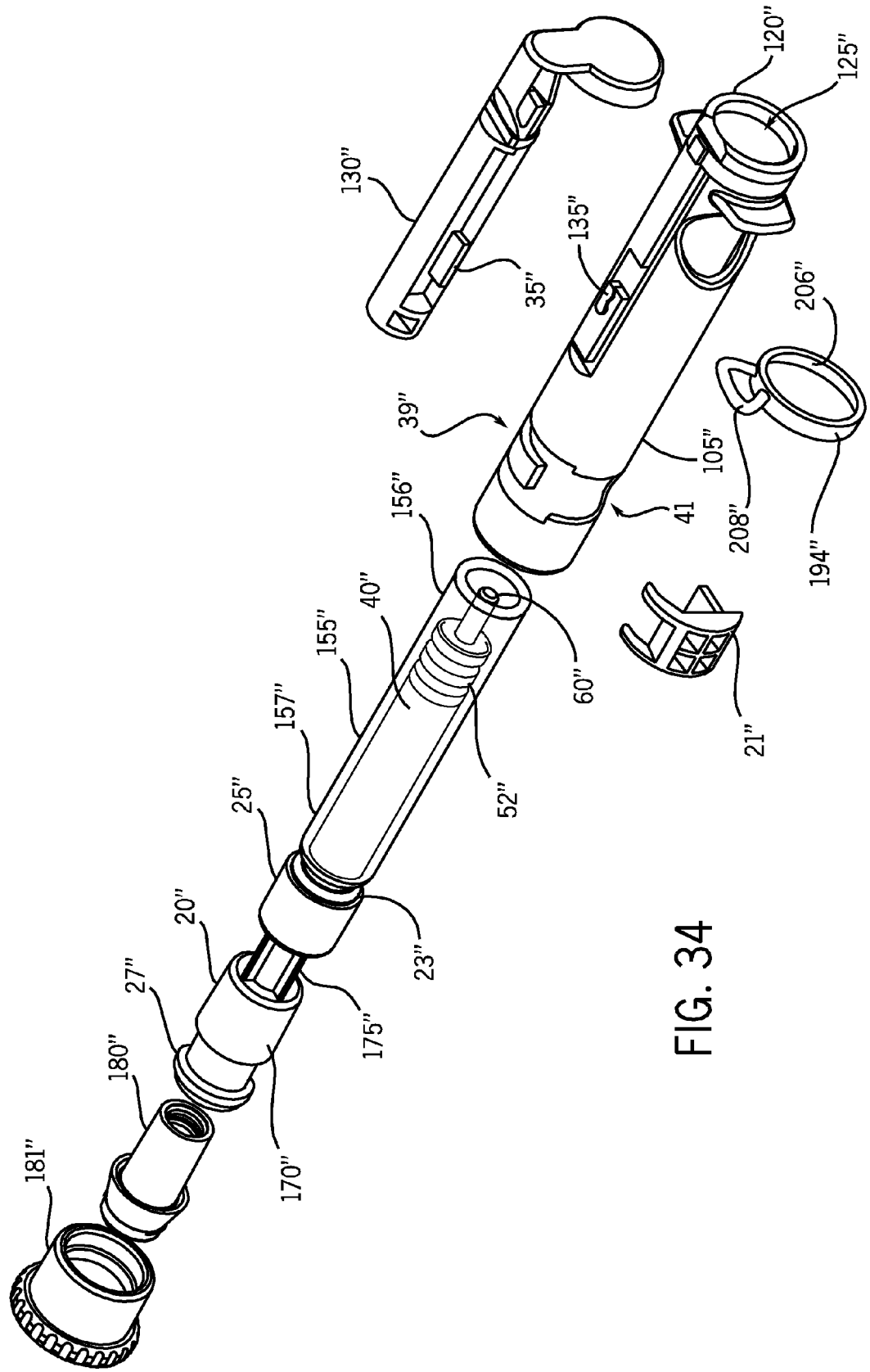
FIG. 34 is an exploded perspective view of the injector system of FIG. 33.

Referring to FIG. 34, the injector system 100" of this embodiment also has a tamper-evident band 194". In a preferred embodiment, the tamper-evident band 194" is made of a polyethylene material that flexes to a point, and then fractures. As shown in FIG. 34, in one embodiment the tamper-evident band 194" comprises a first annular portion 206" that engages the injector body 105", and a second portion 208" that engages the plunger rod 130". The second portion 208" of the tamper evident band 194" has a notch 210" that operates as a frangible region to break upon a minimal force being applied to the plunger rod 130" to activate the system 100", thereby breaking the second portion 208" into two pieces.

In one embodiment the tamper-evident band 194" will break at the notch 210" upon approximately 0.003" of movement of the plunger rod 130". Additionally, in a preferred embodiment the tamper-evident band 194" is made of a different color, such as red, to draw attention from the user as a reminder to for the user to review the band 194" for any fracture prior to usage of the system 100".

As is explained in detail herein, if lateral movement of the plunger rod 130" occurs, or if sufficient radial outward or rotational force is applied to the plunger rod 130" to fracture the retention member 135", the tamper-evidence band 194" will provide visual evidence of such occurrence. Put another way, since the plunger rod 130" is retained to the injector body 105" by the cooperation between the retention members 135" and the receiving cavities 35", and since the tamper evident bands 194" are broken upon activation of the system 100" or upon removal of the plunger rod 130" from the injector body 105", a visual safety or tamper-evident indicator is provided to any subsequent user that the system 100' has been compromised. In usage, upon lateral movement of the plunger rod 130" the band 194" will break at the notch 210" and the plunger rod 130" can be removed from the injector body 105". The tamper-evident band 194" generally remains affixed to the injector body 105" following fracture and removal of the plunger rod 130".

In a preferred embodiment the injector device 100" is manufactured in a multi-step multiple-shot molding process which creates the injector body 105", plunger rod 130", hub clip 21", and tamper-evident band 194". In one such embodiment the first step comprises the manufacture of the syringe body 105". In this step the entire syringe body 105", including the hinge rods 200", the retaining member 135" and all other components described herein, is molded in a mold utilizing a polycarbonate material. After the syringe body 105" has been molded the mold is opened, the fixture holding the syringe body 105" is rotated a certain number of degrees, and the mold is closed with the syringe body remaining in the mold cavity. In this next step the plunger rod 130" and the hinge clip 21" are molded in proper position on the syringe body 105". Specifically, the plunger rod 130" is molded on the retaining members 135" to create the receiving members 35", and the hinge clip 21" is molded over the hinge rods 200' to allow the hinge clip 21" to be rotatably connected to the syringe body 105". Preferably, the materials utilized to create the plunger rod 130" and the hinge clip 21" should be materials that will not mechanically or chemically bond with the material of the syringe body 105". In one embodiment the plunger rod 130" and hinge clip 21" are made of a high impact polystyrene so as to prevent any mechanical or chemical bonding with the polycarbonate of the syringe body 105". After the plunger rod 130" and hinge clip 21" have been molded in place on the syringe body 105", the mold is again opened and the fixture rotated once again. The mold is then closed around the syringe body 105" having the plunger rod 130" and hinge clip 21" affixed thereto. In this next step the tamper-evident band 194" is molded around the syringe body 105" and plunger rod 130". Again, in a preferred embodiment the material utilized to create the band 194" should be a material that will not mechanically or chemically bond with the materials of the syringe body 105" and the plunger rod 130". In one embodiment the band 194" is made of a polyethylene having a colorant, such as red. After the band 194" has been molded on the components of the injector system 100" the mold is opened and the finished component removed.

In order to use injector device 100", a medical professional will engage finger grips 145" with his/her index and middle fingers and will engage proximal surface 151" of plunger push surface 150" with his/her thumb. By squeezing his/her thumb and fingers together, plunger push surface 150" and finger grips 145" are moved closer to one another. Also by squeezing his/her thumb and fingers together, the pushing surface 152" applies an axial distal force on proximal end portion 156" of pharmaceutical cartridge 155". However, because the hub clip 21" precludes axial distal movement of the hub 20", the application of a distally directed axial force on proximal end portion 156" of pharmaceutical cartridge 155" causes pharmaceutical cartridge 155" to move from its first, inactivated position (see FIG. 35) toward its second, activated position. The squeezing force also causes plunger rod 130" to move axially distally relative to injector body 105" from its first, engaged position, to its second, released position in which the receiving members 35" are disengaged from the retention members 135". During this axial movement the tamper-evident band 194" is fractured at the notch 210". Additionally, the pharmaceutical cartridge 155" is transferred to its second, activated position when plunger rod 130" is manipulated to its second, released position. In the second released position the plunger rod 130" is now free from the injector body 105" and can be removed therefrom.

Next, the plunger rod 130" can be positioned such that the distal end portion 132" of the plunger rod 130" is adjacent to connection member 160" on piston/plunger 52". Where connection member 160" is a threaded member, a complementary connection member 190" having complementary threads is provided on the distal end portion 132" of plunger rod 130" such that plunger rod 130" can be threadably attached to connection member 160" on piston/plunger 52", thereby enabling a user to move piston/plunger 52" proximally and/or distally through the application of proximally and/or distally directed forces to plunger push surface 150" and/or to plunger rod 130".

After plunger rod 130" has been connected to piston/plunger 52" using complementary connection members 160", 190", a pharmaceutical product contained in pharmaceutical cartridge 155" can be delivered to a patient or transferred to another medical device by the application of an axial distally-directed force to plunger rod 130", e.g., through the application of a distally directed force to proximal surface 151" of plunger push surface 150". If desired, fluids can be aspirated into pharmaceutical cartridge at any time through the application of a proximally directed force to plunger push surface 150".

While various aspects of the invention have been discussed herein in connection with certain preferred embodiments, it will be appreciated that various modifications, permutations, additions and/or sub-combinations of these aspects and embodiments are possible. Such modifications, permutations, additions and/or sub-combinations are intended to be within the spirit and scope of the present invention as claimed in the appended claims.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein. Accordingly, while the specific embodiments have been illustrated and described, numerous modifications come to mind without significantly departing from the spirit of the invention and the scope of protection is only limited by the scope of the accompanying claims.

What is claimed is:

1. A system for delivering a pharmaceutical product from a cartridge, comprising:
    an injector body having a side wall, said side wall having a proximal end portion, a distal end portion, an inner surface and an outer surface, said inner surface of said side wall defining a cavity for receiving at least a portion of a cartridge;
    a plunger rod having a proximal end portion and a distal end portion, said plunger rod having a pushing surface for engaging a cartridge positioned within said cavity of said injector body;
    one or more retention members disposed on one of said outer surface of said injector body and an outer surface of said plunger rod, the other of said injector body and said plunger rod having one or more receiving members adapted to engage said retention members when said plunger rod is in a first position;
    said pushing surface of said plunger rod constructed to move a cartridge positioned within said cavity axially as said plunger rod is moved from said first position to a second position, whereby movement of said plunger rod from said first position to said second position releases said plunger rod from said injector body, and whereby movement of said plunger rod from said first position to said second position simultaneously activates a pharmaceutical cartridge positioned within said cavity; and,
    a tamper-evident band having a first portion secured to said injector body and a second portion secured to said plunger rod.

2. The injector system of claim 1, wherein one of said first portion and said second portion of said tamper-evident band has a frangible portion that fractures upon certain movement of said plunger rod with respect to said injector body.

3. The injector system of claim 1, wherein said tamper-evident band has a distinct color different from said injector body and said plunger rod to provide a visual indicator upon fracture to a user.

4. The injector system of claim 1, wherein said one or more retention members and said one or more receiving members are constructed to cooperatively retain said plunger rod to said injector body adjacent said outer surface of said injector body when said plunger rod is in a first position, said one or more retention members and said one or more receiving members constructed to cooperatively release said plunger rod from said injector body when said plunger rod is transitioned axially toward said distal end of said injector body to a second position.

5. The injector system of claim 1, wherein said one or more retention members are disposed on said outer surface of said injector body, and wherein said one or more receiving members are provided in said plunger rod between said proximal end and said distal end thereof.

6. The injector system of claim 5, wherein said one or more receiving members comprise a cavity having a mating configuration to said retaining members.

7. The injector system of claim 1, wherein a portion of said one or more retention members proximal said outer surface of said injector body have a narrower cross-sectional width than a cross-sectional width of a portion of said retention member distal said outer surface of said injector body to define a dovetail-type configuration.

8. The injector system of claim 1, wherein said pushing surface has an exterior flange extending transversely therefrom to define a cavity for receiving a proximal end of a cartridge, said pushing surface with said flange cooperating to preclude access to a grommet at a proximal end of a cartridge positioned within said cavity.

9. The injector system of claim 1, wherein said distal end portion of said plunger rod has a connection member constructed to attach to a connecting member associated with a piston of a pharmaceutical cartridge positioned within said cavity.

10. The injector system of claim 9, wherein said connection member of said plunger rod has threads formed thereon whereby said plunger rod can be threadably secured to a connecting member mounted on a piston associated with a cartridge positioned within said cavity.

11. The injector system of claim 1, further comprising a hinge clip hingably connected to said injector body, said hinge clip being hingably moveable from a first position wherein a majority of said hinge clip is outside of said cavity of said injector body, and a second position wherein a portion of said hinge clip is inside said cavity of said injector body to laterally retain a hub connected to a cartridge positioned within said cavity.

12. The system of claim 11, wherein said hinge clip is connected to said injector body in both said first and second positions.

13. The system of claim 11, wherein said hinge clip has projections that extend through openings in the side wall of the injector body to engage the hub to prevent axial and radial movement of the hub.

14. A system for delivering a pharmaceutical product from a cartridge, comprising:
an injector body having a side wall having a proximal end portion and a distal end portion, said side wall having an inner surface and an outer surface, said inner surface of said side wall defining a cavity for receiving at least a portion of a cartridge;
a plunger rod having a proximal end portion and a distal end portion, said plunger rod having a pushing surface for engaging a cartridge positioned within said cavity of said injector body; and,
a retention member disposed on one of said outer surface of said sidewall of said injector body and an outer surface of said plunger rod, the other of said injector body and said plunger rod having a receiving member adapted to engage said retention member, wherein cooperation of said retention member and said receiving member precludes radial and rotational movement of the plunger rod when the plunger rod is connected adjacent the sidewall of the injector body in a first position, and wherein said cooperation of said retention member and said receiving member allows axial movement of said plunger rod with respect to said injector body to a second position in which plunger rod is released from said injector body;
wherein said pushing surface of said plunger rod is constructed to move a cartridge positioned within said cavity axially as said plunger rod is moved from said first position to said second position, whereby movement of said plunger rod from said first position to said second position releases said plunger rod from said injector body, and whereby movement of said plunger rod from said first position to said second position simultaneously activates a pharmaceutical cartridge positioned within said cavity.

15. The injector system of claim 14, wherein a portion of said retention member proximal said outer surface of said injector body has a narrower cross-sectional width than a cross-sectional width of a portion of said retention member distal said outer surface of said injector body to define a dovetail-type configuration, and wherein said receiving member comprises a cavity having a mating configuration to said retaining member.

16. The injector system of claim 14, wherein said retention member extends from said injector body, and wherein said plunger rod contains said receiving member.

17. The injector system of claim 14, further comprising a tamper-evident band having a first portion secured to the injector body and a second portion secured to the plunger rod.

18. An injection system for delivering a pharmaceutical product from a cartridge, comprising:
an injector body having a side wall, said side wall having a proximal end portion, a distal end portion, an inner surface and an outer surface, said inner surface of said side wall defining a cavity for receiving at least a portion of a cartridge, said injector body being made of a first material;
a plunger rod having a proximal end portion and a distal end portion, said plunger rod releasably connected to said injector body in a first position, and said plunger rod being removable from said injector body in a second position, said plunger body being made of a second material, said plunger rod having a pushing surface for engaging a cartridge positioned within said cavity of said injector body, wherein said pushing surface of said plunger is constructed to move a cartridge positioned within said cavity axially as said plunger rod is moved from said first position to said second position, whereby movement of said plunger rod from said first position to said second position releases said plunger rod from said injector body, and whereby movement of said plunger rod from said first position to said second position simultaneously activates a pharmaceutical cartridge positioned within said cavity; and,
a tamper-evident band having a first portion secured to said injector body and a second portion secured to said plunger rod, said tamper-evident band being made of a third material, wherein said first material, said second material and said third material are different materials, and wherein said first material, said second material and said third material preclude chemical and mechanical bonding therebetween said materials.

* * * * *